United States Patent
Stephanopoulos et al.

(10) Patent No.: US 9,879,248 B2
(45) Date of Patent: Jan. 30, 2018

(54) ENGINEERED MICROBES AND METHODS FOR MICROBIAL OIL OVERPRODUCTION FROM CELLULOSIC MATERIALS

(71) Applicant: Massachusetts Institute of Technology, Cambridge, MA (US)

(72) Inventors: Gregory Stephanopoulos, Winchester, MA (US); Mitchell Tai, Seattle, WA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/817,489

(22) Filed: Aug. 4, 2015

(65) Prior Publication Data

US 2016/0186163 A1 Jun. 30, 2016

Related U.S. Application Data

(63) Continuation of application No. 13/923,607, filed on Jun. 21, 2013, now Pat. No. 9,096,876.

(60) Provisional application No. 61/663,391, filed on Jun. 22, 2012.

(51) Int. Cl.
| | |
|---|---|
| *C12P 7/64* | (2006.01) |
| *C12P 7/06* | (2006.01) |
| *C12N 9/04* | (2006.01) |
| *C12N 9/92* | (2006.01) |

(52) U.S. Cl.
CPC ............. *C12N 9/92* (2013.01); *C12N 9/0006* (2013.01); *C12P 7/649* (2013.01); *C12P 7/6463* (2013.01); *C12Y 101/0101* (2013.01); *C12Y 101/01009* (2013.01); *C12Y 101/01307* (2013.01); *C12Y 503/01005* (2013.01); *C12P 2203/00* (2013.01); *Y02E 50/13* (2013.01); *Y02E 50/17* (2013.01)

(58) Field of Classification Search
CPC .... C12P 7/649; C12P 7/6463; C12Y 10/0101; C12Y 10/01009; C12Y 10/01307; C12Y 101/01009; C12Y 503/01005; C12N 9/0006

See application file for complete search history.

(56) References Cited

U.S. PATENT DOCUMENTS

| 9,096,876 B2 | 8/2015 | Stephanopoulos et al. |
| 2012/0156717 A1 | 6/2012 | Allnutt et al. |
| 2012/0329109 A1 | 12/2012 | Chua et al. |

FOREIGN PATENT DOCUMENTS

WO WO 2010/147642 A1 12/2010

OTHER PUBLICATIONS

GENBANK Submission; NCBI, Accession No. XP_501496.1; Dujon et al.; Oct. 29, 2008.
GENBANK Submission; NCBI, Accession No. XP_502540.1; Dujon et al.; Oct. 29, 2008.
GENBANK Submission; NCBI, Accession No. XP_503864.1; Dujon et al.; Oct. 29, 2008.
GENBANK Submission; NCBI, Accession No. XP_505266.1; Dujon et al.; Oct. 29, 2008.
Barth et al., Physiology and genetics of the dimorphic fungus *Yarrowia lipolytica*. FEMS Microbiol Rev. Apr. 1997;19(4):219-37.
Beopoulos et al., Yarrowia lipolytica as a model for bio-oil production. Prog Lipid Res. Nov. 2009;48(6):375-87. doi: 10.1016/j.plipres.2009.08.005. Epub Aug. 29, 2009.
Blank et al., Metabolic-flux and network analysis in fourteen hemiascomycetous yeasts. FEMS Yeast Res. Apr. 2005;5(6-7):545-58.
Cao et al., Increasing unsaturated fatty acid contents in *Escherichia coli* by coexpression of three different genes. Appl Microbiol Biotechnol. Jun. 2010;87(1):271-80. doi: 10.1007/s00253-009-2377-x. Epub Feb. 5, 2010.
De Deken, The Crabtree effects and its relation to the petite mutation. J Gen Microbiol. Aug. 1966;44(2):157-65.
Evans et al., 1984. Induction of xylulose-5-phosphate phosphoketolase in a variety of yeasts grown on d-xylose: the key to efficient xylose metabolism. Arch. Microbiol. 139(1):48-52. Abstract only.
Flores et al., Yarrowia lipolytica mutants devoid of pyruvate carboxylase activity show an unusual growth phenotype. Eukaryot Cell. Feb. 2005;4(2):356-64.
Griffiths et al., Selection of direct transesterification as the preferred method for assay of fatty acid content of microalgae. Lipids. Nov. 2010;45(11):1053-60. doi: 10.1007/s11745-010-3468-2. Epub Sep. 5, 2010.
Jeffries, Engineering yeasts for xylose metabolism. Curr Opin Biotechnol. Jun. 2006;17(3):320-6. Epub May 18, 2006.
Jin et al., *Saccharomyces cerevisiae* engineered for xylose metabolism exhibits a respiratory response. Appl Environ Microbiol. Nov. 2004;70(11):6816-25.
Kalwy et al., Toward more efficient protein expression: keep the message simple. Mol Biotechnol. Oct. 2006;34(2):151-6. Abstract only.
Kamisaka et al., DGA1 (diacylglycerol acyltransferase gene) overexpression and leucine biosynthesis significantly increase lipid accumulation in the Deltasnf2 disruptant of *Saccharomyces cerevisiae*. Biochem J. Nov. 15, 2007;408(1):61-8.
Karhumaa et al., 2007. Comparison of the xylose reductase-xylitol dehydrogenase and the xylose isomerase pathways for xylose fermentation by recombinant *Saccharomyces cerevisiae*. Microbial Cell Factories 6(1):5.

(Continued)

*Primary Examiner* — Maryam Monshipouri
(74) *Attorney, Agent, or Firm* — Wolf, Greenfield & Sacks, P.C.

(57) ABSTRACT

The invention relates to engineering microbial cells for utilization of cellulosic materials as a carbon source, including xylose.

18 Claims, 5 Drawing Sheets

(56) References Cited

OTHER PUBLICATIONS

Karhumaa et al., Investigation of limiting metabolic steps in the utilization of xylose by recombinant *Saccharomyces cerevisiae* using metabolic engineering. Yeast. Apr. 15, 2005;22(5):359-68.

Kuyper et al., Minimal metabolic engineering of *Saccharomyces cerevisiae* for efficient anaerobic xylose fermentation: a proof of principle. FEMS Yeast Res. Mar. 2004;4(6):655-64.

Matsushika et al., Ethanol production from xylose in engineered *Saccharomyces cerevisiae* strains: current state and perspectives. Appl Microbiol Biotechnol. Aug. 2009;84(1):37-53. doi: 10.1007/s00253-009-2101-x. Epub Jul. 2, 2009. Abstract only.

Morgunov et al., 2011. Yarrowia lipolytica Yeast Possesses an Atypical Catabolite Repression. Albany 2011: The 17$^{th}$ Conversation. p. 1134-1136.

Pan et al., 2009. Isolation of the Oleaginous Yeasts from the Soil and Studies of Their Lipid-Producing Capacities. Food Technology and Biotechnology 47(2):215-220.

Papanikolaou et al., Accumulation of a cocoa-butter-like lipid by Yarrowia lipolytica cultivated on agro-industrial residues. Curr Microbiol. Feb. 2003;46(2):124-30.

Papanikolaou et al., Lipid production by Yarrowia lipolytica growing on industrial glycerol in a single-stage continuous culture. Bioresour Technol. Mar. 2002;82(1):43-9.

Papanikolaou et al., Single cell oil production by Yarrowia lipolytica growing on an industrial derivative of animal fat in batch cultures. Appl Microbiol Biotechnol. Mar. 2002;58(3):308-12. Epub Dec. 11, 2001.

Perlack et al., 2005. Biomass as Feedstock for a Bioenergy and Bioproducts Industry: The Technical Feasability of a Billion-Ton Annual Supply. Oak Ridge National Lab. USDA.

Ratledge, Biochemistry, Stoichiometry, Substrates and Economics. Single Cell Oil; 1988. Longman Scientific & Technical. p. 33-70.

Ruiz-Herrera et al., Different effectors of dimorphism in Yarrowia lipolytica. Arch Microbiol. Dec. 2002;178(6):477-83. Epub Oct. 15, 2002. Abstract only.

Salusjärvi et al., Transcription analysis of recombinant *Saccharomyces cerevisiae* reveals novel responses to xylose. Appl Biochem Biotechnol. Mar. 2006;128(3):237-61. Abstract only.

Scioli et al., 1997. The use of Yarrowia lipolytica to reduce pollution in olive mill wastewaters. Water Res. 31(10):2520-2524.

Taccari et al., 2012. Screening of yeasts for growth on crude glycerol and optimization of biomass production. Bioresource Technology 1:1. Abstract only.

Tomás-Pejó et al., Adaptation of the xylose fermenting yeast *Saccharomyces cerevisiae* F12 for improving ethanol production in different fed-batch SSF processes. J Ind Microbiol Biotechnol. Nov. 2010;37(11):1211-20. doi: 10.1007/s10295-010-0768-8. Epub Jun. 29, 2010. Abstract only.

Tsigie et al., Lipid production from Yarrowia lipolytica Po1g grown in sugarcane bagasse hydrolysate. Bioresour Technol. Oct. 2011;102(19):9216-22. doi: 10.1016/j.biortech.2011.06.047. Epub Jun. 22, 2011.

Walfridsson et al., Xylose-metabolizing *Saccharomyces cerevisiae* strains overexpressing the TKL1 and TAL1 genes encoding the pentose phosphate pathway enzymes transketolase and transaldolase. Appl Environ Microbiol. Dec. 1995;61(12):4184-90.

Young et al., A molecular transporter engineering approach to improving xylose catabolism in *Saccharomyces cerevisiae*. Metab Eng. Jul. 2012;14(4):401-11. doi: 10.1016/j.ymben.2012.03.004. Epub Mar. 18, 2012. Abstract only.

Zhao et al., Comprehensive algorithm for quantitative real-time polymerase chain reaction. J Comput Biol. Oct. 2005;12(8):1047-64.

ENGINEERED MICROBES AND METHODS FOR MICROBIAL OIL OVERPRODUCTION FROM CELLULOSIC MATERIALS

RELATED APPLICATIONS

This application is a continuation of U.S. provisional patent application Ser. No. 13/923,607, filed Jun. 21, 2013, and claims priority under 35 U.S.C. § 119(e) to U.S. provisional patent application Ser. No. 61/663,391, filed Jun. 22, 2012, the entire contents of each of which are incorporated herein by reference.

GOVERNMENT SUPPORT

This invention was made with Government support under Grant No. DE-AR0000059 awarded by the Department of Energy. The Government has certain rights in the invention.

BACKGROUND

Sustainably produced biofuels are an alternative to fossil fuels and may help to alleviate the depletion of easily accessible fossil fuel stocks, such as cellulosic biomass, while avoiding fossil fuel-associated pollution and greenhouse gas emission, thus satisfying a rising demand for affordable energy in a sustainable way. The development of methods and oil-producing organisms suitable for the efficient conversion of carbon sources to lipids is prerequisite for widespread implementation of microbial biofuel production.

SUMMARY OF CERTAIN ASPECTS OF THE INVENTION

Microbial oil production by heterotrophic organisms is a most promising path for the cost-effective production of biofuels from renewable resources provided high conversion yields can be achieved. The key to cost-effective microbial oil production from renewable feedstocks is a high carbohydrate to oil conversion yield. Additionally, the use of available and abundant cellulosic biomass feedstocks for biofuel production is currently limited by the high cost and energy associated with processing such sources. Metabolic engineering has emerged as the enabling technology applied to this end and numerous examples exist of successful pathway engineering that markedly improved the performance of microbial biocatalysts in the synthesis of chemical, pharmaceutical and fuel products.

Prior efforts at engineering microbes for oil production have focused on amplifying presumed rate-controlling steps in the fatty acid synthesis pathway, using traditional carbon sources such as glucose. Significant drawbacks of such approaches include the high cost of a glucose-based feedstock, and that increasing carbon flux into fatty acid synthesis pathways increases the level of saturated fatty acids in the cell, which activate a potent negative feedback loop of fatty acid biosynthesis.

Some aspects of this disclosure provide a strategy for microbe engineering that combines the utilization of non-traditional carbon sources, such as those obtained from cellulosic materials, including xylose, with amplification of upstream (metabolite-forming pathways, also referred to herein as "push") and downstream (product-sequestering pathways, also referred to herein as "pull") metabolic pathways. Some aspects of this invention provide that a balanced combination of push-and-pull modifications in a microbe results in large carbon flux amplifications into lipid synthesis pathways without significant departures of the concentrations of intermediate metabolites from their homeostatic physiological levels, thus avoiding feedback inhibition of lipid synthesis.

Some aspects of this disclosure provide engineered microbes, and methods of use thereof, that can utilize carbon sources from cellulosic biomass that are not typically or efficiently metabolized for lipid synthesis. In some aspects, such a carbon source in cellulosic biomass is xylose.

According to one aspect of the invention, isolated oleaginous cells are provided. The cells include a genetic modification that increases expression of: a) a xylose reductase (XYL1) gene product and a xylitol dehydrogenase (XYL2) gene product; and/or b) a xylose isomerase (XYLA) gene product. In some embodiments, the cells also include a genetic modification that increases expression of a xylulokinase (XYL3) gene product. In some embodiments, the cells also include a genetic modification that increases expression of a diacylglycerol acyltransferase (DGA) gene product, an acetyl-coA carboxylase (ACC) gene product, a stearoyl-CoA-desaturase (SCD) gene product, and/or an ATP-citrate lyase (ACL) gene product.

In some embodiments, the genetic modification includes a nucleic acid construct that increases the expression of the gene product, the nucleic acid construct comprising (a) an expression cassette comprising a nucleic acid sequence encoding the gene product under the control of a suitable homologous or heterologous promoter, and/or (b) a nucleic acid sequence that modulates the level of expression of the gene product when inserted into the genome of the cell. In certain embodiments, the promoter is an inducible or a constitutive promoter.

In some embodiments, the promoter is a TEF promoter. In some embodiments, the expression construct further comprises an intron. In certain embodiments, the intron is downstream of the transcription initiation site. In some preferred embodiments, the intron is within the nucleic acid sequence encoding the gene product.

In some embodiments, the nucleic acid construct inhibits or disrupts the natural regulation of a native gene encoding the gene product resulting in overexpression of the native gene. In certain embodiments, inhibition or disruption of the natural regulation of the native gene is mediated by deletion, disruption, mutation and/or substitution of a regulatory region, or a part of a regulatory region regulating expression of the gene.

In some embodiments, the gene product is a transcript. In other embodiments, the gene product is a protein.

In some embodiments, the nucleic acid construct is inserted into the genome of the cell.

In some embodiments, the increased expression of the gene product confers a beneficial phenotype for the conversion of a carbon source to a fatty acid, fatty acid derivative and/or triacylglycerol (TAG) to the cell. In certain embodiments, the beneficial phenotype is a modified fatty acid profile, a modified TAG profile, an increased fatty acid and/or triacylglycerol synthesis rate, an increase conversion yield, an increased triacylglycerol accumulation in the cell, and/or an increased triacylglycerol accumulation in a lipid body of the cell. Increased in this context means increased relative to cells that do not have increased expression of the gene product. In some embodiments, the synthesis rate, yield or accumulation of a fatty acid or a TAG of the cell is at least 2-fold increased as compared to unmodified cells of the same cell type. In certain embodiments, the synthesis rate, yield or accumulation of a fatty acid or a TAG of the cell is at least 5-fold increased as compared to unmodified cells of the same cell type. In some embodiments, the synthesis rate, yield or accumulation of a fatty acid or a TAG of the cell is at least 10-fold increased as compared to unmodified cells of the same cell type.

In some embodiments, the cell converts a carbon source to a fatty acid or a TAG at a conversion rate within the range of about 0.025 g/g to about 0.32 g/g (g TAG produced/g Glucose consumed). In some embodiments, the cell converts a carbon source to a fatty acid or a TAG at a conversion rate of at least about 0.11 g/g. In some embodiments, the cell converts a carbon source to a fatty acid or a TAG at a conversion rate of at least about 0.195 g/g. In some embodiments, the cell converts a carbon source to a fatty acid or a TAG at a conversion rate of at least about 0.27 g/g.

In some embodiments, the cell comprises a lipid body or vacuole.

In some embodiments, the cell is a bacterial cell, an algal cell, a fungal cell, or a yeast cell. In certain embodiments, the cell is an oleaginous yeast cell. In preferred embodiments, the cell is a *Y. lipolytica* cell.

According to another aspect of the invention, cultures are provided that include the oleaginous cells described herein. In some embodiments, the culture also includes a carbon source. In some embodiments, the carbon source comprises a fermentable sugar. In certain embodiments, the fermentable sugar is a C5 and/or a C6 sugar. In some embodiments, the carbon source includes glucose. In some embodiments, the carbon source includes xylose. In certain embodiments, the xylose is at a concentration of about 8% wt./vol. In some embodiments, the carbon source includes arabitol.

In some embodiments, the carbon source includes glycerol. In certain embodiments, the glycerol is at a concentration of about 2% wt./vol.

In some embodiments, the culture includes a carbon/nitrogen (C/N) ratio of about 100.

According to another aspect of the invention, methods are provided. The methods includes contacting a carbon source with an isolated oleaginous cell as described herein and incubating the carbon source contacted with the cell under conditions suitable for at least partial conversion of the carbon source into a fatty acid or a triacylglycerol by the cell.

In some embodiments, the carbon source comprises a fermentable sugar. In certain embodiments, the fermentable sugar is a C5 and/or a C6 sugar. In some embodiments, the carbon source includes glucose. In some embodiments, the carbon source includes xylose. In certain embodiments, the xylose is at a concentration of about 8% wt./vol. In some embodiments, the carbon source includes arabitol.

In some embodiments, the carbon source includes glycerol. In certain embodiments, the glycerol is at a concentration of about 2% wt./vol.

In some embodiments, the method includes a carbon/nitrogen (C/N) ratio of about 100.

In some embodiments, the carbon source contacted with the isolated oleaginous cell is incubated in a reactor. In some embodiments, the carbon source is contacted with the isolated oleaginous cell and incubated for conversion of the carbon source to a fatty acid or a triacylglycerol in a fed batch process. In other embodiments, the carbon source is contacted with the isolated oleaginous cell and incubated for conversion of the carbon source to a fatty acid or a triacylglycerol in a continuous process.

In some embodiments, the fatty acid or the triacylglycerol is extracted from the carbon source contacted with the isolated oleaginous cell by solvent extraction. In certain embodiments, the solvent extraction is a chloroform methanol extraction. In other embodiments, the solvent extraction is a hexane extraction.

In some embodiments, the fatty acid or the triacylglycerol is separated from the carbon source contacted with the isolated oleaginous cell and subsequently refined by transesterification.

According to another aspect of the invention, methods for increasing productivity of production of fatty acid or triacylglycerol by an oleaginous cell are provided. The methods include culturing an oleaginous cell as described herein or a culture as described herein with at least two types of carbon sources, wherein the first type of carbon source contains or is xylose, and wherein the second type of carbon source is a carbon source other than xylose. In such methods the productivity of production of fatty acid or triacylglycerol by an oleaginous cell is improved relative to culturing the cell or the culture without the second type of carbon source.

In some embodiments, the second type of carbon source contains or is a C2 carbon source, a C3 carbon source, a C5 carbon source other than xylose or a C6 carbon source.

In some embodiments, the methods also include culturing the oleaginous cell or the culture and the at least two types of carbon sources under conditions suitable for at least partial conversion of the carbon source into a fatty acid or a triacylglycerol by the cell or the culture.

In some embodiments, the xylose is at a concentration of about 8% wt./vol.

In some embodiments, the second type of carbon source includes glucose. In some embodiments, the second type of carbon source includes arabitol. In some embodiments, the second type of carbon source includes glycerol. In certain embodiments, the glycerol is at a concentration of about 2% wt./vol. In some embodiments, the second type of carbon source comprises cellulosic material.

In some embodiments, the method comprises a carbon/nitrogen (C/N) ratio of about 100.

The subject matter of this application may involve, in some cases, interrelated products, alternative solutions to a particular problem, and/or a plurality of different uses of a single system or article.

Other advantages, features, and uses of the invention will be apparent from the detailed description of certain non-limiting embodiments, the drawings, which are schematic and not intended to be drawn to scale, and the claims.

BRIEF DESCRIPTION OF THE DRAWINGS

FIG. 1A: Diagram of utilization pathways for xylose, xylitol, and D-arabitol. FIG. 1B: Shake flask experiments with control strain MTYL038 grown on these substrates demonstrate growth on D-arabitol, poor growth on xylitol, and no growth on xylose.

DETAILED DESCRIPTION OF CERTAIN EMBODIMENTS OF THE INVENTION

Figure 1A:
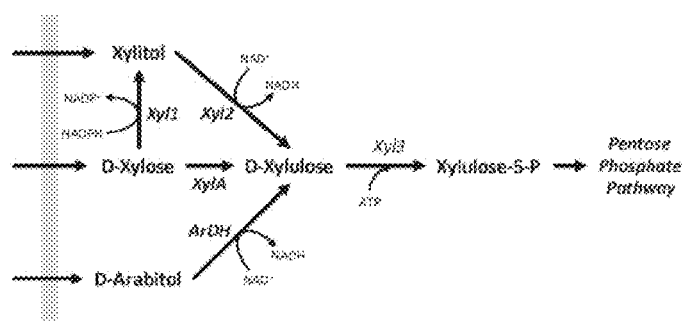
FIGS. 1A-1B. Diagnosing the functionality of endogenous xylose utilization genes.

Liquid biofuels are a promising alternative to fossil fuels that can help ease concerns about climate change and smoothen supply uncertainties (1). Biodiesel, jet oil and other oil-derived fuels in particular are necessary for aviation and heavy vehicle transport. They are presently produced exclusively from vegetable oils, which is a costly and unsustainable path (2). An attractive possibility is the nonphotosynthetic conversion of renewable carbohydrate feedstocks to oil (3). For biodiesel, a transition from vegetable oil to microbial oil production for the oil feedstock presents numerous additional advantages: adaptability to diverse feedstocks, flexibility in land requirements, efficient process cycle turnover, and ease of scale-up (4). In the search for improved feedstocks, the push towards cellulosic biofuels is a clear choice. Cellulosic biomass mitigates the need to compete with food crop production; an estimated 1.3+ billion dry tons per year of biomass is potentially available in the US alone (Perlack 2005). Additionally, cellulosic materials can be more efficiently grown and more stably produced compared to sugar crops. However cellulosic materials are not naturally consumable by most biofuel-producing organisms, and thus cellulose requires pretreatment and hydrolysis to break the material down into monomeric sugar. The resulting hydrolysate can then be used as a sugar rich feedstock. Since hydrolysis of lignocellulosic biomass results in 20-30% carbohydrates in the form of xylose, utilization of pentose sugars is one of the first steps toward efficiently using cellulosic materials.

Another factor in a cost-effective microbial technology for the conversion of carbohydrates to oils is a high carbohydrate to oil conversion yield. Metabolic engineering has emerged as the enabling technology applied to this end and numerous examples exist of successful pathway engineering that markedly improved the performance of microbial biocatalysts in the synthesis of chemical, pharmaceutical and fuel products. Prior efforts at engineering microbes with high lipid synthesis have focused on amplifying presumed rate-controlling steps in the fatty acid synthesis pathway. These efforts, however, have produced mixed results, presumably because modulating fatty acid flux gave rise to the levels of saturated fatty acids, which are potent allosteric inhibitors of fatty acid biosynthetic enzymes providing a negative feedback loop for the fatty acid biosynthesis. Certain aspects of this disclosure describe an approach that combines the introduction of xylose metabolic genes to utilize xylose as a carbon source, with the amplification of upstream, metabolite-forming pathways in the lipid synthesis pathway, with a similar increase in the flux of downstream, metabolite-consuming pathways. Combining the utilization of xylose as a carbon source with a push-and-pull strategy can achieve large flux amplifications without significant departures of the concentrations of intermediate metabolites from their homeostatic physiological levels, while growing the cells on a renewable cellulosic carbohydrate feedstock.

The oleaginous yeast *Yarrowia lipolytica* is an attractive candidate for microbial oil production, which has also demonstrated usefulness in a wide range of other industrial applications: citric acid production, protein production (e.g., proteases and lipases), and bioremediation. With a fully sequenced genome and a growing body of genetic engineering tools, engineering of *Y. lipolytica* can be achieved with relative ease. *Y. lipolytica* also has been found to be robust in culture, able to grow on a variety of substrates, and has been used for lipid production on agro-industrial residues, industrial glycerol, and industrial fats. It has excellent lipid accumulation capacity, commonly accumulating up to 36% of its dry cell weight (DCW) in lipids.

The metabolic pathways for de novo lipid synthesis in *Y. lipolytica* are beginning to be fully mapped out. Glucose entering glycolysis enters the mitochondria as pyruvate for use in the TCA cycle; however, excess acetyl-coA is transported from the mitochondria to the cytosol via the citrate shuttle. Cytosolic acetyl-CoA is then converted into malonyl-CoA by acetyl-CoA carboxylase (ACC) as the first step of fatty acid synthesis. After fatty acid synthesis, triacylglycerol (TAG) synthesis follows the Kennedy pathway, which occurs in the endoplasmic reticulum (ER) and lipid bodies. Acyl-CoA is the precursor used for acylation to the glycerol-3-phosphate backbone to form lysophosphatidic acid (LPA), which is further acylated to form phosphatidic acid (PA). PA is then dephosphorylated to form diacylglycerol (DAG) and then a final acylation occurs by diacylglycerol acyltransferase (DGA) to produce TAG.

Transport of acetyl-CoA from the mitochondria to the cytosol is carried out by the ATP-citrate lyase (ACL)-mediated cleavage of citrate via the citrate shuttle yielding Acetyl-CoA and Oxaloacetate (OAA). Acetyl-CoA carboxylase (ACC) then catalyzes the first committed step towards lipid biosynthesis, converting cytosolic acetyl-CoA into malonyl-CoA, which is the primary precursor for fatty acid elongation. Completed fatty acyl-CoA chains are then transported to the endoplasmic reticulum (ER) or lipid body membranes for the final assembly of triacylglycerol (TAG) via the Kennedy pathway. Over 80% of the storage lipids produced in *Y. lipolytica* are in the form of TAG. Cytosolic OAA is converted to malate by malic dehydrogenase and transported back into the mitochondria to complete the citrate shuttle cycle. Reducing equivalents in the form of NADPH is provided either by the pentose phosphate pathway (PPP) or by malic enzyme in the transhydrogenase cycle. In *Y. lipolytica*, high PPP flux and ineffectual malic enzyme overexpression suggest that the former is the primary source for NADPH.

Instead of utilizing glucose as a carbon source, the metabolic conversion of xylose to lipids is a favorable alternative for reasons described herein. Xylose enters the cell and can be catabolized through a redox pathway, whereby xylose reductase (XD or XYL1) converts xylose to xylitol using NADPH as a reducing equivalent. Xylitol is then converted to xylulose through the action of xylitol dehydrogenase (XDH or XYL2) using NAD+ as an electron acceptor. Xylulokinase (XK or XYL3) then phosphorylates xylulose to form xylulose-5-P. Alternatively, the xylose isomerase (XYLA) enzyme bypasses the requirement of reducing equivalents, producing xylulose directly from xylose, which is then converted to xylulose-5-P by XYL3. Xylulose-5-P can then enter central metabolism through the non-oxidative pathway of the PPP where it ultimately produces glyceraldehyde-3-phosphate (G3P) and fructose-6-phosphate (F6P). These two products can then enter the rest of central metabolism, going through glycolysis to enter the TCA cycle. Production of lipids occurs normally through the transport of mitochondrial citrate into the cytosol, where it is cleaved by ATP citrate lyase into oxaloacetate and cytosolic acetyl-coA. The acetyl-coA can then enter the fatty acid synthesis pathway through the enzymatic activity of acetyl-coA carboxylase. Acyl-CoA generated from the fatty acid synthase complex are transferred to a glycerol-3-phosphate backbone and ultimately sequestered within lipid bodies as triacylglycerol (TAG).

Intracellular lipid accumulation can occur via two methods: de novo lipid synthesis or ex novo incorporation of exogenous fatty acids and lipids. Lipid accumulation most commonly occurs when nutrient supply is exhausted in the presence of excess carbon. In culture, this state typically coincides with the onset of the stationary phase. In practice, the most commonly used limiting-nutrient is nitrogen, as it is easily controllable in media compositions. Despite these inducible conditions, lipid synthesis pathways are highly regulated in order for the organism to balance cell growth with energy storage. For example, ACC alone is regulated at multiple levels and by multiple factors.

This tight regulation was circumvented in certain cases. By eliminating peroxisomal oxidation pathways and engineering glycerol metabolism, *Y. lipolytica* was able to achieve 40%-70% lipids through ex novo lipid accumulation. Coexpression of Δ6- and Δ12-desaturase genes allowed for significant production of γ-linolenic acid (GLA) (20). However, engineering lipid biosynthesis pathways in *Y. lipolytica* is still relatively unexplored and strategies are still being developed for effective engineering of the lipid production pathways to maximize output.

Some aspects of this disclosure provide engineered microbes for the production of biofuel or biofuel precursor. The term "biofuel" refers to a fuel that is derived from a biological source, such as a living cell, microbe, fungus, or plant. The term includes, for example, fuel directly obtained from a biological source, for example, by conventional extraction, distillation, or refining methods, and fuel produced by processing a biofuel precursor obtained from a biological source, for example by chemical modification, such as transesterification procedures. Examples of biofuels that are directly obtainable are alcohols such as ethanol, propanol, and butanol, fat, and oil. Examples of biofuels that are obtained by processing of a biofuel precursor (e.g., a lipid), are biodiesel (e.g., produced by transesterification of a lipid), and green diesel/modified oil fuels (e.g., produced by hydrogenation of an oil). Biodiesel, also referred to as fatty acid methyl (or ethyl) ester, is one of the economically most important biofuels today and can be produced on an industrial scale by transesterification of lipids, in which sodium hydroxide and methanol (or ethanol) reacts with a lipid, for example, a triacylglycerol, to produce biodiesel and glycerol.

Feedstocks for industrial-scale production of biodiesel include animal fats, vegetable oils, palm oil, hemp, soy, rapeseed, flax, sunflower, and oleaginous algae. In other approaches, biomass is converted by a microbe into a biofuel precursor, for example, a lipid, that is subsequently extracted and further processed to yield a biofuel. The term "biomass" refers to material produced by growth and/or propagation of a living cell or organism, for example, a microbe. Biomass may contain cells, microbes and/or intracellular contents, for example cellular fatty acids and TAGS, as well as extracellular material. Extracellular material includes, but is not limited to, compounds secreted by a cell, for example, secreted fatty acids or TAGs. Important types of biomass for biofuel production are algal biomass and plant-derived biomass, for example, corn stover and wood fiber. In some embodiments, biomass for biofuel or biofuel precursor production may comprise plant derived sugars, for example, sugarcane or corn derived sugars.

Some aspects of this disclosure relate to the engineering and development of a microbial source of lipids, useful, for example, for economically viable, industrial-scale biodiesel production. The term "lipid" refers to fatty acids and their derivatives. Accordingly, examples of lipids include fatty acids (FA, both saturated and unsaturated); glycerides or glycerolipids, also referred to as acylglycerols (such as monoglycerides (monoacylglycerols), diglycerides (diacylglycerols), triglycerides (triacylglycerols, TAGs, or neutral fats); phosphoglycerides (glycerophospholipids); nonglycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid bodies, lipid droplets, or vacuoles.

Some aspects of this invention relate to engineered microbes for biofuel or biofuel precursor production. In some embodiments, the microbes provided herein are engineered to use 5C sugars as a carbon source, for example xylose. In some embodiments, the microbes provided herein also are engineered to optimize their lipid metabolism for lipid production. The term "lipid metabolism" refers to the molecular processes that involve the creation or degradation of lipids. Fatty acid synthesis, fatty acid oxidation, fatty acid desaturation, TAG synthesis, TAG storage and TAG degradation are examples of processes that are part of the lipid metabolism of a cell. Accordingly, the term "fatty acid metabolism" refers to all cellular or organismic processes that involve the synthesis, creation, transformation or degradation of fatty acids. Fatty acid synthesis, fatty acid oxidation, TAG synthesis, and TAG degradation are examples of processes are part of the fatty acid metabolism of a cell.

The term "triacylglycerol" (TAG, sometimes also referred to as triglyceride) refers to a molecule comprising a single molecule of glycerol covalently bound to three fatty acid molecules, aliphatic monocarboxylic acids, via ester bonds, one on each of the glycerol molecule's three hydroxyl (OH) groups. Triacylglycerols are highly concentrated stores of metabolic energy because of their reduced, anhydrous nature, and are a suitable feedstock for biodiesel production.

Many cells and organisms store metabolic energy in the form of fatty acids and fatty acid derivatives, such as TAGs. Fatty acids and their derivatives, such as TAGs, provide an ideal form to store metabolic energy. The energy contained in the C—C bonds can be efficiently released by β-oxidation, a reaction formally equivalent to the reverse of fatty acid biosynthesis, but mediated and regulated by different enzymes constituting a different molecular pathway. Microbes can derive fatty acids from external supply, endogenous turnover, and de novo synthesis. Some aspects of this invention relate to the identification of a microbe for biofuel or biofuel precursor production based on the microbe's ability to synthesize and store fatty acids or fatty acid derivatives, such as TAGs, efficiently from an externally supplied carbon source.

Natural fatty acid molecules commonly have an unbranched, aliphatic chain, or tail, of 4 to 28 carbon atoms. Fatty acids are referred to as "saturated", if all carbon atoms of the aliphatic chain are connected via a C—C single bond, or as "unsaturated", if two or more carbon atoms are connected via a C—C double bond. Unsaturated fatty acids play important roles in the regulation of membrane fluidity, cellular activity, metabolism and nuclear events governing gene transcription.

The spectrum of fatty acids in yeast consists mostly of C16 and C18 fatty acids, for example palmitic acid (C16), palmitoleic acid (C16), stearic acid (C18) and oleic acid (C18). Palmitic acid is an unbranched, saturated fatty acid, with an aliphatic chain of 16 carbon atoms (carbon atoms/unsaturated bonds: 16.0). Stearic acid is an unbranched, saturated fatty acid with an aliphatic chain of 18 carbon atoms (18.0). Palmitoleic acid is a monounsaturated fatty acid with an aliphatic chain of 16 carbon atoms (16.1). Oleic acid is a monounsaturated fatty acid with an aliphatic chain of 18 carbon atoms (18.1). Minor fatty acid species in yeast include C14 and C26 fatty acids, which play essential functions in protein modification or as components of sphingolipids and GPI anchors, respectively.

De novo synthesis of fatty acids utilizes substantial amounts of metabolites, acetyl-CoA, ATP and NADPH, and thus competes with other cellular processes that are dependent on these compounds. NADPH is required for two reduction steps in the fatty acid elongation cycle, linking fatty acid synthesis to the metabolic state of the cell and results in fatty acid synthesis being restricted to conditions of high energy load of the cells, indicated by increased ATP/AMP ratio, elevated reduction equivalents and elevated acetyl-CoA pool. Almost all subcellular organelles are involved in fatty acid metabolism, indicating that maintenance of fatty acid homeostasis requires regulation at multiple levels. Lipid synthesis steps that generate metabolites, acetyl-CoA, ATP, or NADPH for lipid biosynthesis are sometimes referred to herein as "push steps" of lipid synthesis. The amplification of a process that increases the production of a metabolites, acetyl-CoA, ATP, or NADPH for lipid synthesis in a cell, for example, by overexpressing a gene product mediating such a metabolite-producing process, is sometimes referred to herein as a "push modification."

Most organisms, including yeast, are able to synthesize fatty acids de novo from a variety of carbon sources. In an initial step, acetyl-CoA is carboxylated by the addition of $CO_2$ to malonyl-CoA, by the enzyme acetyl-CoA carboxylase (ACC; encoded by ACC1 and HFA1 in yeast). Biotin is an essential cofactor in this reaction, and is covalently attached to the ACC apoprotein, by the enzyme biotin: apoprotein ligase (encoded by BPL1/ACC2 in yeast). ACC is a trifunctional enzyme, harboring a biotin carboxyl carrier protein (BCCP) domain, a biotin-carboxylase (BC) domain, and a carboxyl-transferase (CT) domain. In most bacteria, these domains are expressed as individual polypeptides and assembled into a heteromeric complex. In contrast, eukaryotic ACC, including mitochondrial ACC variants (Hfa1 in yeast) harbor these functions on a single polypeptide. Malonyl-CoA produced by ACC serves as a two carbon donor in a cyclic series of reactions catalyzed by fatty acid synthase, FAS, and elongases.

The immediate product of de novo fatty acid synthesis are saturated fatty acids. Saturated fatty acids are known to be the precursors of unsaturated fatty acids in eukaryotes, including yeast. Unsaturated fatty acids are generally produced by desaturation of C—C single bonds in saturated fatty acids by specialized enzymes, called desaturases. The control mechanisms that govern the conversion of saturated fatty acids to unsaturated fatty acids are not well understood. In eukaryotes, unsaturated fatty acids play important roles in the regulation of membrane fluidity, cellular activity, metabolism and nuclear events that govern gene transcription. Typically, about 80% of yeast fatty acids are monounsaturated, meaning that they contain one unsaturated bond in their aliphatic chain.

Fatty acids are potent inhibitors of fatty acid synthesis and the feedback inhibition of fatty acid synthesis by fatty acids is a major obstacle in engineering microbes for oil production. Some aspects of this disclosure are based on the recognition that while push modifications of lipid synthesis are typically unable to override fatty acid-mediated feedback inhibition of lipid synthesis, a combination of a push modification (e.g., ACC1 overexpression) with a pull modification (e.g., DGA1 overexpression), can efficiently bypass the feedback inhibition, thus fully realizing the increased carbon flux to the lipid synthesis pathway, for example, in TGAs stored in a lipid body or vacuole of the cell Engineering the Capacity for 5C Sugar Utilization and Increased Lipid Synthesis in Oleaginous Microbes Some aspects of this disclosure provide strategies for engineering microbes for oil production. In some embodiments, such strategies employ genetic engineering of oleaginous microbes, for example, *Y. lipolytica*, to utilize five carbon (5C) sugars, such as xylose, as a carbon source for lipid synthesis.

Some aspects of this disclosure are based on the surprising discovery, described herein, that oleaginous microbes, such as *Y. lipolytica*, which are unable to metabolize xylose for lipid synthesis, can be engineered to be able to utilize five carbon (5C) sugars as feedstocks or in feedstocks. Some aspects of this disclosure relate to the engineering of oleaginous microbes to utilize 5C sugars, such as xylose, through the introduction of exogenous xylose metabolism genes or the amplification or modification of endogenous xylose metabolism genes. Some aspects of this disclosure relate to the discovery that an oleaginous microbe such as *Y. lipolytica* has within its genome a copy of an XYL3 gene that produces a functional gene product. Some aspects of this disclosure are related to the heterologous overexpression of xylose metabolism genes, such as XYL1 and XYL2, or XYLA, in an oleaginous microbe such as *Y. lipolytica*, which enables the microbe to utilize xylose as a sole carbon source in the production TAGs.

Some aspects of this disclosure provide strategies for additional engineering of 5C-utilizing microbes for oil production. In some embodiments, such strategies employ genetic engineering of oleaginous microbes, for example *Y. lipolytica*, to simultaneously amplify a push- and a pull-step of lipid synthesis. Significant increases of lipid production in oleaginous yeast host cells can be achieved using these strategies.

According to some aspects of this invention, modifying the lipid metabolism in a microbe in accordance with methods provided herein, for example by simultaneously overexpressing a gene product mediating a metabolite-generating (push) step and a gene product mediating a product-sequestering (pull) step of lipid synthesis, allows for the generation of a microbe optimized for use in biofuel or biofuel precursor production processes. Some aspects of this invention provide strategies and methods for engineering the fatty acid metabolism in a microbe by simultaneously amplifying a push step and a pull step of lipid biosynthesis, resulting in increased synthesis rate and accumulation of fatty acids and fatty acid derivatives in the microbe.

Some aspects of this invention provide methods that include genetic modifications resulting in the modulation of the expression and/or activity of gene products regulating the lipid metabolism of microbes for biofuel or biofuel precursor production. Such genetic modifications according to some aspects of this invention are targeted to increase carbohydrate to fatty acid and/or TAG conversion in order to optimize the modified microbe for large-scale production of lipids from a carbon source, for example, a carbohydrate source such as a 5C sugar, e.g., xylose. Some modifications provided according to some aspects of this invention, for example, overexpression, knockout, knock-down, activation and/or inhibition of specific gene products, may be effected alone or in combination, and/or in combination with other modifications known to those of skill in the art. The term "modification" refers to both genetic manipulation, for example, overexpression, knockout, knock-down, activation and/or inhibition of specific gene products, and non-genetic manipulation, for example, manipulation of the growth media, substrate, substrate pretreatment, pH, temperature, conversion process, etc.

A modification of gene expression, also referred to herein as a modulation of gene expression, can be a disruption or inhibition of the natural regulation of expression, an over-expression, an inhibition of expression, or a complete abolishment of expression of a given gene. The insertion of a heterologous promoter upstream of a native gene sequence, for example the native DGA1 or ACC1 gene sequence, or the deletion of regulatory sequences within a promoter, for example regulatory sequences that mediate the feedback inhibition of the DGA1 or ACC1 gene by saturated fatty acids, are examples of a disruption or inhibition of the natural regulation of expression. Strategies for the modulation of gene expression may include genetic alterations, for example by recombinant technologies, such as gene targeting or viral transductions, or non-genetic alterations, for example environmental alterations known to result in the up- or down-regulation of gene expression, or transient delivery of modulators, for example drugs or small RNA molecules to the target cells. Methods for genetic and non-genetic alterations of microbes are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology*, Part A, Volume 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

The term "overexpression", as used herein, refers to an increased level of expression of a given gene product in a given cell, cell type or cell state, as compared to a reference cell, for example, a wild type cell of the same cell type or a cell of the same cell type but lacking a specific modification, for example, a genetic modification. Forced, continuous expression of the DGA1 and/or ACC1 gene in *Y. lipolytica* cells exhibiting concentrations of saturated fatty acids that would inhibit DGA1 or ACC1 gene expression in wild-type cells is an example of gene overexpression.

Some aspects of this invention provide a method for the manipulation of the activity of a xylose reductase (XD or XYL1) gene product in a microbe, including for biofuel or biofuel precursor production. The XYL1 gene encodes a reductase that reduces xylose to xylitol, the initial step of metabolizing xylose as required for entry into the PPP pathway. XYL1 uses NADPH as a reducing equivalent, generating xylitol and NADP+. Xylitol is then acted upon by XYL2 as described herein. In some embodiments, the manipulation is an overexpression. In some embodiments, the manipulation is effected by contacting a microbe for biofuel or biofuel precursor production with an expression construct comprising a nucleic acid coding for a XYL1 gene product, for example, an XD protein, operably linked to a heterologous promoter, for example, a constitutive or an inducible promoter. In some embodiments, the nucleic acid coding for a XYL1 gene product comprises the coding sequence of SEQ ID NO: 1. In some embodiments, the XYL1 is *Scheffersomyces stipitis* XYL1, for example, *S. stipitis* XYL1 comprising the amino acid sequence of SEQ ID NO: 2. In some embodiments, the microbe is *Y. lipolytica*. In some embodiments, manipulation of the activity of a XYL1 gene product in a microbe is effected to confer a beneficial phenotype for large-scale carbohydrate to lipid conversion, using xylose as the carbohydrate source. XYL1 gene and gene product sequences are well known to those of skill in the art. Exemplary, representative gene and gene product sequences can be found under entry XM_001385144 in the NCBI database (www.ncbi.nlm.nih.gov).

Non-limiting examples of suitable sequences of XYL1 nucleic acid and protein sequences are provided below. Additional suitable XYL1 sequences, including sequences from other species, will be apparent to those of skill in the art, and the invention is not limited in this respect.

Xylose Reductase
XYL1 DNA (*Scheffersomyces stipitis*)
XM_001385144

(SEQ ID NO: 1)
TACAACTATACTACAATGCCTTCTATTAAGTTGAACTCTGGTTACGACAT

GCCAGCCGTCGGTTTCGGCTGTTGGAAAGTCGACGTCGACACCTGTTCTG

AACAGATCTACCGTGCTATCAAGACCGGTTACAGATTGTTCGACGGTGCC

GAAGATTACGCCAACGAAAAGTTAGTTGGTGCCGGTGTCAAGAAGGCCAT

TGACGAAGGTATCGTCAAGCGTGAAGACTTGTTCCTTACCTCCAAGTTGT

GGAACAACTACCACCACCCAGACAACGTCGAAAAGGCCTTGAACAGAACC

-continued

CTTTCTGACTTGCAAGTTGACTACGTTGACTTGTTCTTGATCCACTTCCC

AGTCACCTTCAAGTTCGTTCCATTAGAAGAAAAGTACCCACCAGGATTCT

ACTGTGGTAAGGGTGACAACTTCGACTACGAAGATGTTCCAATTTTAGAG

ACCTGGAAGGCTCTTGAAAAGTTGGTCAAGGCCGGTAAGATCAGATCTAT

CGGTGTTTCTAACTTCCCAGGTGCTTTGCTCTTGGACTTGTTGAGAGGTG

CTACCATCAAGCCATCTGTCTTGCAAGTTGAACACCACCCATACTTGCAA

CAACCAAGATTGATCGAATTCGCTCAATCCCGTGGTATTGCTGTCACCGC

TTACTCTTCGTTCGGTCCTCAATCTTTCGTTGAATTGAACCAAGGTAGAG

CTTTGAACACTTCTCCATTGTTCGAGAACGAAACTATCAAGGCTATCGCT

GCTAAGCACGGTAAGTCTCCAGCTCAAGTCTTGTTGAGATGGTCTTCCCA

AAGAGGCATTGCCATCATTCCAAAGTCCAACACTGTCCCAAGATTGTTGG

AAAACAAGGACGTCAACAGCTTCGACTTGGACGAACAAGATTTCGCTGAC

ATTGCCAAGTTGGACATCAACTTGAGATTCAACGACCCATGGGACTGGGA

CAAGATTCCTATCTTCGTCTAAGAAGGTTGCTTTATAGAGAGGAAATAAA

ACCTAATATACATTGATTGTACATTT

Xylose Reductase
XYL1 Protein (Scheffersomyces stipitis)
XP_001385181
(SEQ ID NO: 2)
MPSIKLNSGYDMPAVGFGCWKVDVDTCSEQIYRAIKTGYRLFDGAEDYAN

EKLVGAGVKKAIDEGIVKREDLFLTSKLWNNYHHPDNVEKALNRTLSDLQ

VDYVDLFLIHFPVTFKFVPLEEKYPPGFYCGKGDNFDYEDVPILETWKAL

EKLVKAGKIRSIGVSNFPGALLLDLLRGATIKPSVLQVEHHPYLQQPRLI

EFAQSRGIAVTAYSSFGPQSFVELNQGRALNTSPLFENETIKAIAAKHGK

SPAQVLLRWSSQRGIAIIPKSNTVPRLLENKDVNSFDLDEQDFADIAKLD

INLRFNDPWDWDKIPIFV

Some aspects of this invention provide a method for the manipulation of the activity of a xylitol dehydrogenase (XDH or XYL2) gene product in a microbe for biofuel or biofuel precursor production. As described herein, this manipulation may be made in combination with manipulation of XYL1. The XYL2 gene encodes a dehydrogenase that dehydrogenates xylitol to xylulose, the second step of metabolizing xylose as required for entry into the PPP. XYL2 uses NAD+ as an electron acceptor, generating xylulose and NADH. Xylulose is then acted upon by XYL3 as described herein. In some embodiments, the manipulation is an overexpression. In some embodiments, the manipulation is effected by contacting a microbe for biofuel or biofuel precursor production with an expression construct comprising a nucleic acid coding for a XYL2 gene product, for example, an XDH protein, operably linked to a heterologous promoter, for example, a constitutive or an inducible promoter. In some embodiments, the nucleic acid coding for a XYL2 gene product comprises the coding sequence of SEQ ID NO: 3. In some embodiments, the XYL2 is Scheffersomyces stipitis XYL2, for example, S. stipitis XYL2 comprising the amino acid sequence of SEQ ID NO: 4. In some embodiments, the microbe is Y. lipolytica. In some embodiments, manipulation of the activity of a XYL2 gene product in a microbe is effected to confer a beneficial phenotype for large-scale carbohydrate to lipid conversion, using xylose as the carbohydrate source. XYL2 gene and gene product sequences are well known to those of skill in the art. Exemplary, representative gene and gene product sequences can be found under entry XM_001386945 in the NCBI database (www.ncbi.nlm.nih.gov).

Non-limiting examples of suitable sequences of XYL2 nucleic acid and protein sequences are provided below. Additional suitable XYL2 sequences, including sequences from other species, will be apparent to those of skill in the art, and the invention is not limited in this respect.

Xylitol dehydrogenase
XYL2 DNA (Scheffersomyces stipitis)
XM_001386945
(SEQ ID NO: 3)
CCTCACTTTAGTTTGTTTCAATCACCCCTAATACTCTTCACACAATTAAA

ATGACTGCTAACCCTTCCTTGGTGTTGAACAAGATCGACGACATTTCGTT

CGAAACTTACGATGCCCCAGAAATCTCTGAACCTACCGATGTCCTCGTCC

AGGTCAAGAAAACCGGTATCTGTGGTTCCGACATCCACTTCTACGCCCAT

GGTAGAATCGGTAACTTCGTTTTGACCAAGCCAATGGTCTTGGGTCACGA

ATCCGCCGGTACTGTTGTCCAGGTTGGTAAGGGTGTCACCTCTCTTAAGG

TTGGTGACAACGTCGCTATCGAACCAGGTATTCCATCCAGATTCTCCGAC

GAATACAAGAGCGGTCACTACAACTTGTGTCCTCACATGGCCTTCGCCGC

TACTCCTAACTCCAAGGAAGGCGAACCAAACCCACCAGGTACCTTATGTA

AGTACTTCAAGTCGCCAGAAGACTTCTTGGTCAAGTTGCCAGACCACGTC

AGCTTGGAACTCGGTGCTCTTGTTGAGCCATTGTCTGTTGGTGTCCACGC

CTCTAAGTTGGGTTCCGTTGCTTTCGGCGACTACGTTGCCGTCTTTGGTG

CTGGTCCTGTTGGTCTTTTGGCTGCTGCTGTCGCCAAGACCTTCGGTGCT

AAGGGTGTCATCGTCGTTGACATTTTCGACAACAAGTTGAAGATGGCCAA

GGACATTGGTGCTGCTACTCACACCTTCAACTCCAAGACCGGTGGTTCTG

AAGAATTGATCAAGGCTTTCGGTGGTAACGTGCCAAACGTCGTTTTGGAA

TGTACTGGTGCTGAACCTTGTATCAAGTTGGGTGTTGACGCCATTGCCCC

AGGTGGTCGTTTCGTTCAAGTCGGTAACGCTGCTGGTCCAGTCAGCTTCC

CAATCACCGTTTTCGCCATGAAGGAATTGACTTTGTTCGGTTCTTTCAGA

TACGGATTCAACGACTACAAGACTGCTGTTGGAATCTTTGACACTAACTA

CCAAAACGGTAGAGAAAATGCTCCAATTGACTTTGAACAATTGATCACCC

ACAGATACAAGTTCAAGGACGCTATTGAAGCCTACGACTTGGTCAGAGCC

GGTAAGGGTGCTGTCAAGTGTCTCATTGACGGCCCTGAGTAAGTCAACCG

CTTGGCTGGCCCAAAGTGAACCAGAAACGAAAATGATTATCAAATAGCTT

TATAGACCTTTATCCAAATTTATGTAAACTAATAG

Xylitol Dehydrogenase
XYL2 Protein (Scheffersomyces stipitis)
XP_001386982
(SEQ ID NO: 4)
MTANPSLVLNKIDDISFETYDAPEISEPTDVLVQVKKTGICGSDIHFYAH

GRIGNFVLTKPMVLGHESAGTVVQVGKGVTSLKVGDNVAIEPGIPSRFSD

EYKSGHYNLCPHMAFAATPNSKEGEPNPPGTLCKYFKSPEDFLVKLPDHV

SLELGALVEPLSVGVHASKLGSVAFGDYVAVFGAGPVGLLAAAVAKTFGA

KGVIVVDIFDNKLKMAKDIGAATHTFNSKTGGSEELIKAFGGNVPNVVLE

-continued

CTGAEPCIKLGVDAIAPGGRFVQVGNAAGPVSFPITVFAMKELTLFGSFR

YGFNDYKTAVGIFDTNYQNGRENAPIDFEQLITHRYKFKDAIEAYDLVRA

GKGAVKCLIDGPE

Some aspects of this invention provide a method for the manipulation of the activity of a xylulokinase (XK or XYL3) gene product in a microbe for biofuel or biofuel precursor production. As described herein, this manipulation may be made in combination with manipulation of XYL1 and XYL2. The XYL3 gene encodes a kinase that uses ATP as a phosphate donor, phosphorylating xylulose to form xylulose-5-P adnADP, the final step of metabolizing xylose as required for entry into the PPP. Xylulose-5-P enters the PPP where it ultimately produces glyceraldehyde-3-phosphate (G3P) and fructose-6-phosphate (F6P). These two products can then enter the rest of central metabolism, going through glycolysis to enter the TCA cycle. Production of lipids occurs normally through pathways described herein. In some embodiments, the manipulation is an overexpression. In some embodiments, the manipulation is effected by contacting a microbe for biofuel or biofuel precursor production with an expression construct comprising a nucleic acid coding for a XYL3 gene product, for example, an XK protein, operably linked to a heterologous promoter, for example, a constitutive or an inducible promoter. In some embodiments, the nucleic acid coding for a XYL3 gene product comprises the coding sequence of SEQ ID NO: 5. In some embodiments, the XYL3 is *Y. lipolytica* XYL2, for example, *Y. lipolytica* XYL2 comprising the amino acid sequence of SEQ ID NO: 6. In some embodiments, the microbe is *Y. lipolytica*. In some embodiments, manipulation of the activity of a XYL3 gene product in a microbe is effected to confer a beneficial phenotype for large-scale carbohydrate to lipid conversion, using xylose as the carbohydrate source. XYL3 gene and gene product sequences are well known to those of skill in the art. Exemplary, representative gene and gene product sequences can be found under entry XM_505266 in the NCBI database (www.ncbi.nlm.nih.gov).

Non-limiting examples of suitable sequences of XYL3 nucleic acid and protein sequences are provided below. Additional suitable XYL3 sequences, including sequences from other species, will be apparent to those of skill in the art, and the invention is not limited in this respect.

Xylulokinase
XYL3 DNA (*Yarrowia lipolytica*)
XM_505266

(SEQ ID NO: 5)
ATGTATCTCGGACTGGATCTTTCGACTCAACAGCTCAAGGGCATCATTCT

GGACACAAAAACGCTGGACACGGTCACACAAGTCCATGTGGACTTTGAGG

ACGACTTGCCGCAGTTCAACACCGAAAAGGGCGTCTTTCACAGCTCTACA

GTGGCCGGAGAAATCAATGCTCCTGTGGCAATGTGGGGGCAGCTGTGGA

CTTGCTGATAGAGCGTCTGTCAAAGGAAATAGACCTTTCCACGATCAAGT

TTGTGTCGGGCTCGTGCCAGCAACACGGCTCTGTTTATCTCAACAGCAGC

TACAAGGAGGGCCTGGGTTCTCTGGACAAACACAAAGACTTGTCTACAGG

AGTGTCATCCTTACTGGCGCTCGAAGTCAGCCCCAATTGGCAGGATGCAA

GCACGGAGAAGGAGTGTGCGCAGTTTGAGGCTGCAGTCGGCGGTCCCGAG

CAGCTGGCTGAGATCACTGGCTCTCGAGCACATACTCGTTTCACCGGGCC

CCAGATTCTCAAGGTCAAGGAACGCAACCCCAAGGTATTCAAGGCCACGT

CACGGGTCCAGCTCATATCCAACTTTCTAGCATCTCTGTTTGCCGGCAAG

GCGTGCCCCTTTGATCTTGCTGACGCCTGTGGAATGAATCTGTGGGACAT

CCAGAATGGCCAGTGGTGCAAGAAACTCACAGATCTCATCACCGATGACA

CCCACTCGGTCGAGTCCCTCCTTGGAGACGTGGAAACAGACCCCAAGGCT

CTACTGGGCAAAATCTCGCCCTATTTCGTCTCCAAGGGCTTCTCTCCCTC

TTGTCAGGTGGCACAGTTCACAGGCGACAACCCAGGCACTATGCTGGCTC

TCCCCTTACAGGCCAATGACGTGATTGTGTCTTTGGGAACATCTACGACC

GCCCTCGTCGTAACAAACAAGTACATGCCCGACCCCGGATACCATGTGTT

CAACCACCCCATGGAGGGATACATGGGCATGCTGTGCTACTGCAACGGAG

GTCTAGCACGAGAGAAGATCCGAGACGAGCTTGGAGGCTGGGACGAGTTT

AATGAGGCGGCCGAGACCACCAACACAGTGTCTGCTGACGATGTCCATGT

TGGCATCTACTTTCCACTACGAGAAATCCTTCCTCGAGCAGGTCCCTTTG

AACGACGTTTCATCTACAACAGACAAAGTGAACAGCTTACAGAGATGGCT

TCTCCAGAGGACTCACTGGCAACCGAACACAAACCGCAGGCTCAAAATCT

CAAGGACACGTGGCCGCCACAAATGGACGCCACTGCCATCATTCAAAGCC

AGGCCCTCAGTATCAAAATGAGACTCCAACGCATGATGCATGGCGATATT

GGAAAGGTGTATTTTGTGGGAGGCGCCTCGGTCAACACTGCTATCTGCAG

CGTAATGTCTGCCATCTTAAAACCAACAAAGGGCGCTTGGAGATGTGGTC

TGGAAATGGCAAACGCTTGTGCCATTGGAAGTGCCCATCACGCCTGGCTT

TGCGACCCCAACAAGACAGGCCAGGTACAGGTTCACGAAGAAGAGGTCAA

ATACAAGAATGTGGACACAGACGTGCTACTCAAGGCGTTCAAGCTGGCCG

AAAACGCCTGCCTGGAGAAATAA

Xylulokinase
XYL3 Protein (*Yarrowia lipolytica*)
XP_505266

(SEQ ID NO: 6)
MYLGLDLSTQQLKGIILDTKTLDTVTQVHVDFEDDLPQFNTEKGVFHSST

VAGEINAPVAMWGAAVDLLIERLSKEIDLSTIKFVSGSCQQHGSVYLNSS

YKEGLGSLDKHKDLSTGVSSLLALEVSPNWQDASTEKECAQFEAAVGGPE

QLAEITGSRAHTRFTGPQILKVKERNPKVFKATSRVQLISNFLASLFAGK

ACPFDLADACGMNLWDIQNGQWCKKLTDLITDDTHSVESLLGDVETDPKA

LLGKISPYFVSKGFSPSCQVAQFTGDNPGTMLALPLQANDVIVSLGTSTT

ALVVTNKYMPDPGYHVFNHPMEGYMGMLCYCNGGLAREKIRDELGGWDEF

NEAAETTNTVSADDVHVGIYFPLREILPRAGPFERRFIYNRQSEQLTEMA

SPEDSLATEHKPQAQNLKDTWPPQMDATAIIQSQALSIKMRLQRMMHGDI

GKVYFVGGASVNTAICSVMSAILKPTKGAWRCGLEMANACAIGSAHHAWL

CDPNKTGQVQVHEEEVKYKNVDTDVLLKAFKLAENACLEK

Some aspects of this invention provide a method for the manipulation of the activity of a xylose isomerase (XYLA) gene product in a microbe for biofuel or biofuel precursor production. The XYLA gene encodes an isomerase that converts xylose directly to xylulose without the requirement of reducing equivalents, effectively eliminating one step as described herein with the redox pathway (XYL1/XYL2). Xylulose may then be acted upon by XYL3 to form xylulose-5-P, the final step of metabolizing xylose as required for entry into the PPP, as described herein. In some embodiments, the manipulation is an overexpression. In some embodiments, the manipulation is effected by contacting a microbe for biofuel or biofuel precursor production with an expression construct comprising a nucleic acid coding for a XYLA gene product, for example, a XYLA protein, operably linked to a heterologous promoter, for example, a constitutive or an inducible promoter. In some embodiments, the nucleic acid coding for a XYLA gene product comprises the coding sequence of SEQ ID NO: 7. In some embodiments, the XYLA is *Piromyces* sp. E2 XYLA, for example, *Piromyces* sp. E2 XYLA comprising the amino acid sequence of SEQ ID NO: 8. In some embodiments, the microbe is *Y. lipolytica*. In some embodiments, manipulation of the activity of a XYLA gene product in a microbe is effected to confer a beneficial phenotype for large-scale carbohydrate to lipid conversion, using xylose as the carbohydrate source. XYLA gene and gene product sequences are well known to those of skill in the art. Exemplary, representative gene and gene product sequences can be found under GenBank entries HV445113, FW568191, and HC036431 in the NCBI database (www.ncbi.nlm.nih.gov).

Non-limiting examples of suitable sequences of XYLA nucleic acid and protein sequences are provided below. Additional suitable XYLA sequences, including sequences from other species, will be apparent to those of skill in the art, and the invention is not limited in this respect.

*Piromyces* sp E2 Xylose isomerase
DNA sequence
(SEQ ID NO: 7)
ATGGCTAAAGAGTACTTCCCACAGATTCAGAAGATAAAGTTCGAGGGCAA

AGATTCTAAAAACCCTTTGGCTTTCCACTACTATGATGCAGAGAAGGAAG

TCATGGGAAAGAAAATGAAGGATTGGTTGAGATTTGCTATGGCTTGGTGG

CATACTTTGTGTGCTGAAGGTGCAGACCAGTTCGGCGGTGGCACTAAGTC

TTTTCCTTGGAATGAGGGTACTGATGCCATTGAAATCGCCAAACAAAAGG

TAGACGCTGGTTTTGAGATCATGCAGAAGTTGGGCATCCCTTATTACTGT

TTTCACGATGTCGATTTGGTGAGTGAAGGCAATAGTATAGAGGAATACGA

GTCTAACTTAAAGGCAGTCGTTGCCTATTTGAAGGAGAAGCAAAAGGAAA

CTGGTATCAAATTGTTGTGGAGTACTGCTAACGTCTTCGGCCACAAAGA

TACATGAACGGTGCTTCTACTAATCCAGACTTTGATGTAGTCGCTAGAGC

TATAGTCCAGATTAAGAATGCTATCGACGCCGGAATTGAGTTGGGAGCTG

AGAACTATGTTTTTTGGGGAGGTAGGGAAGGCTATATGTCTTTGTTGAAT

ACTGACCAGAAGAGAGAAAGAACACATGGCAACAATGTTAACTATGGC

AAGAGATTACGCAAGGAGTAAGGGCTTTAAGGGCACTTTTTTGATTGAAC

CTAAGCCTATGGAACCAACTAAACACCAATATGATGTTGACACTGAAACA

GCCATCGGTTTCTTGAAGGCCCACAACTTGGATAAAGATTTTAAGGTAAA

CATTGAGGTCAATCACGCCACCTTGGCCGGTCACACTTTCGAACATGAAT

TGGCTTGTGCTGTTGATGCTGGAATGTTGGGTTCTATTGATGCAAATAGA

GGCGATTATCAGAATGGTTGGGATACTGATCAATTTCCAATCGACCAATA

CGAATTGGTTCAAGCCTGGATGGAAATCATAAGAGGTGGTGGCTTTGTAA

CTGGTGGAACTAACTTCGATGCCAAAACAAGAAGAAACTCCACTGACTTG

GAGGATATCATTATTGCTCACGTTTCCGGTATGGATGCAATGGCCAGGGC

CTTGGAGAACGCTGCTAAGTTGTTACAAGAATCCCCCTACACTAAGATGA

AGAAAGAGAGGTACGCATCATTCGATTCTGGAATCGGCAAGGATTTTGAG

GACGGAAAGTTGACTTTAGAGCAGGTTTATGAGTACGGTAAAAAGAATGG

CGAGCCTAAACAAACCTCTGGTAAGCAGGAATTGTACGAAGCTATTGTCG

CAATGTATCAATAA

*Piromyces* sp E2
Xylose Isomerase
Protein Sequence
(SEQ ID NO: 8)
MAKEYFPQIQKIKFEGKDSKNPLAFHYYDAEKEVMGKKMKDWLRFAMAWW

HTLCAEGADQFGGGTKSFPWNEGTDAIEIAKQKVDAGFEIMQKLGIPYYC

FHDVDLVSEGNSIEEYESNLKAVVAYLKEKQKETGIKLLWSTANVFGHKR

YMNGASTNPDFDVVARAIVQIKNAIDAGIELGAENYVFWGGREGYMSLLN

TDQKREKEHMATMLTMARDYARSKGFKGTFLIEPKPMEPTKHQYDVDTET

AIGFLKAHNLDKDFKVNIEVNHATLAGHTFEHELACAVDAGMLGSIDANR

GDYQNGWDTDQFPIDQYELVQAWMEIIRGGGFVTGGTNFDAKTRRNSTDL

EDIIIAHVSGMDAMARALENAAKLLQESPYTKMKKERYASFDSGIGKDFE

DGKLTLEQVYEYGKKNGEPKQTSGKQELYEAIVAMYQ

Some aspects of this invention provide a method for the manipulation of the activity of a diacylglycerol acyltransferase 1 (DGA1) gene product in a microbe for biofuel or biofuel precursor production. The DGA1 gene encodes an acyltransferase that catalyzes the terminal step of triacylglycerol (TAG) formation, acylating diacylglycerol using acyl-CoA as an acyl donor. The result of this acyltransferase reaction are triacylglycerols, which do not exhibit the same inhibitory feedback effect on fatty acid synthesis as fatty acids themselves. TAGs are typically stored in lipid bodies or vacuoles in lipid producing cells. In some embodiments, the manipulation is an overexpression. In some embodiments, the manipulation is effected by contacting a microbe for biofuel or biofuel precursor production with an expression construct comprising a nucleic acid coding for a DGA1 gene product, for example, a DGAT2 protein, operably linked to a heterologous promoter, for example, a constitutive or an inducible promoter. In some embodiments, the nucleic acid coding for a DGA1 gene product comprises the coding sequence of SEQ ID NO: 9. In some embodiments, the DGA1 is *Y. lipolytica* DGA1, for example, *Y. lipolytica* DGA1 comprising the amino acid sequence of SEQ ID NO: 10. In some embodiments, the microbe is *Y. lipolytica*. In some embodiments, manipulation of the activity of a DGA1 gene product in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. DGA1 gene and gene product sequences are well known to those of skill in the art. Exemplary, representative gene and gene product sequences can be found under entry XM_504700 in the NCBI database (www.ncbi.nlm.nih.gov).

Non-limiting examples of suitable sequences of DGA1 nucleic acid and protein sequences are provided below.

Additional suitable DGA1 sequences, including sequences from other species, will be apparent to those of skill in the art, and the invention is not limited in this respect.

>gi|50554582|ref|XM_504700.1|Yarrowia lipolytica
YALI0E32769p (YALI0E32769g) mRNA, complete cds
(SEQ ID NO: 9)
ATGACTATCGACTCACAATACTACAAGTCGCGAGACAAAAACGACACGGC

ACCCAAAATCGCGGGAATCCGATATGCCCCGCTATCGACACCATTACTCA

ACCGATGTGAGACCTTCTCTCTGGTCTGGCACATTTTCAGCATTCCCACT

TTCCTCACAATTTTCATGCTATGCTGCGCAATTCCACTGCTCTGGCCATT

TGTGATTGCGTATGTAGTGTACGCTGTTAAAGACGACTCCCCGTCCAACG

GAGGAGTGGTCAAGCGATACTCGCCTATTTCAAGAAACTTCTTCATCTGG

AAGCTCTTTGGCCGCTACTTCCCCATAACTCTGCACAAGACGGTGGATCT

GGAGCCCACGCACACATACTACCCTCTGGACGTCCAGGAGTATCACCTGA

TTGCTGAGAGATACTGGCCGCAGAACAAGTACCTCCGAGCAATCATCTCC

ACCATCGAGTACTTTCTGCCCGCCTTCATGAAACGGTCTCTTTCTATCAA

CGAGCAGGAGCAGCCTGCCGAGCGAGATCCTCTCCTGTCTCCCGTTTCTC

CCAGCTCTCCGGGTTCTCAACCTGACAAGTGGATTAACCACGACAGCAGA

TATAGCCGTGGAGAATCATCTGGCTCCAACGGCCACGCCTCGGGCTCCGA

ACTTAACGGCAACGGCAACAATGGCACCACTAACCGACGACCTTTGTCGT

CCGCCTCTGCTGGCTCCACTGCATCTGATTCCACGCTTCTTAACGGGTCC

CTCAACTCCTACGCCAACCAGATCATTGGCGAAAACGACCCACAGCTGTC

GCCCACAAAACTCAAGCCCACTGGCAGAAAATACATCTTCGGCTACCACC

CCCACGGCATTATCGGCATGGGAGCCTTTGGTGGAATTGCCACCGAGGGA

GCTGGATGGTCCAAGCTCTTTCCGGGCATCCCTGTTTCTCTTATGACTCT

CACCAACAACTTCCGAGTGCCTCTCTACAGAGAGTACCTCATGAGTCTGG

GAGTCGCTTCTGTCTCCAAGAAGTCCTGCAAGGCCCTCCTCAAGCGAAAC

CAGTCTATCTGCATTGTCGTTGGTGGAGCACAGGAAAGTCTTCTGGCCAG

ACCCGGTGTCATGGACCTGGTGCTACTCAAGCGAAAGGGTTTTGTTCGAC

TTGGTATGGAGGTCGGAAATGTCGCCCTTGTTCCCATCATGGCCTTTGGT

GAGAACGACCTCTATGACCAGGTTAGCAACGACAAGTCGTCCAAGCTGTA

CCGATTCCAGCAGTTTGTCAAGAACTTCCTTGGATTCACCCTTCCTTTGA

TGCATGCCCGAGGCGTCTTCAACTACGATGTCGGTCTTGTCCCCTACAGG

CGACCCGTCAACATTGTGGTTGGTTCCCCCATTGACTTGCCTTATCTCCC

ACACCCCACCGACGAAGAAGTGTCCGAATACCACGACCGATACATCGCCG

AGCTGCAGCGAATCTACAACGAGCACAAGGATGAATATTTCATCGATTGG

ACCGAGGAGGGCAAAGGAGCCCCAGAGTTCCGAATGATTGAGTAA

>gi|50554583|ref|XP_504700.1|YALI0E32769p
[Yarrowia lipolytica]
(SEQ ID NO: 10)
MTIDSQYYKSRDKNDTAPKIAGIRYAPLSTPLLNRCETFSLVWHIFSIPT

FLTIFMLCCAIPLLWPFVIAYVVYAVKDDSPSNGGVVKRYSPISRNFFIW

KLFGRYFPITLHKTVDLEPTHTYYPLDVQEYHLIAERYWPQNKYLRAIIS

TIEYFLPAFMKRSLSINEQEQPAERDPLLSPVSPSSPGSQPDKWINHDSR

YSRGESSGSNGHASGSELNGNGNNGTTNRRPLSSASAGSTASDSTLLNGS

LNSYANQIIGENDPQLSPTKLKPTGRKYIFGYHPHGIIGMGAFGGIATEG

AGWSKLFPGIPVSLMTLTNNFRVPLYREYLMSLGVASVSKKSCKALLKRN

QSICIVVGGAQESLLARPGVMDLVLLKRKGFVRLGMEVGNVALVPIMAFG

ENDLYDQVSNDKSSKLYRFQQFVKNFLGFTLPLMHARGVFNYDVGLVPYR

RPVNIVVGSPIDLPYLPHPTDEEVSEYHDRYIAELQRIYNEHKDEYFIDW

TEEGKGAPEFRMIE

Some aspects of this invention provide a method for the manipulation of an acetyl-CoA carboxylase (ACC) gene product in a microbe for biofuel or biofuel precursor production, for example, in *Y. lipolytica*. ACC gene products mediate the conversion of acetyl-CoA, the main C2-precursor in fatty acid synthesis, to malonyl-CoA, which is considered the first committed step in fatty acid synthesis and has been suggested to also be the rate-limiting step in fatty acid synthesis (see Cao Y, Yang J, Xian M, Xu X, Liu W. Increasing unsaturated fatty acid contents in *Escherichia coli* by coexpression of three different genes. Appl Microbiol Biotechnol. 2010). In some embodiments, ACC activity manipulation is ACC overexpression. In some embodiments, the manipulation is effected by contacting a microbe for biofuel or biofuel precursor production with an expression construct comprising a nucleic acid coding for an ACC gene product, for example, an ACC1 protein, operably linked to a heterologous promoter, for example, a constitutive or an inducible promoter. In some embodiments, the nucleic acid coding for an ACC gene product comprises the coding sequence of SEQ ID NO: 11. In some embodiments, the ACC gene product is an ACC1 protein comprising the amino acid sequence of SEQ ID NO: 12. In some embodiments, ACC overexpression in a microbe increases fatty acid synthesis rate and/or confers a beneficial phenotype for large-scale carbohydrate to biofuel or biofuel precursor conversion, for example increased lipid synthesis rate, increased carbohydrate to lipid conversion efficiency, increased lipid storage and, increased growth rate, increased tolerance to concentrations of a substance, e.g. a carbon source, a biofuel or biofuel precursor, or a toxic substance. ACC gene and gene product sequences are well known to those of skill in the art. Exemplary, representative gene and gene product sequences can be found under the entry for GeneIDs: 855750 and 2909424, or under the entry NC_006069 in the NCBI database (www.ncbi.nlm.nih.gov).

Non-limiting examples of suitable sequences of ACC nucleic acid and protein sequences are provided below. Additional suitable ACC sequences, including sequences from other species, will be apparent to those of skill in the art, and the invention is not limited in this respect.

ACC encoding nucleic acid sequence:
(SEQ ID NO: 11)
ATGCGACTGCAATTGAGGACACTAACACGTCGGTTTTTCAGGTGAGTAAA

CGACGGTGGCCGTGGCCACGACAGCCGAGGCGTCACGATGGGCCAGACGA

GCACATTCTCGCCGCCACAACCTCGCCAGCACAAGAAACTAACCCAGTAT

GGCTTCAGGATCTTCAACGCCAGATGTGGCTCCCTTGGTGGACCCCAACA

TTCACAAAGGTCTCGCCTCTCATTTCTTTGGACTCAATTCTGTCCACACA

GCCAAGCCCTCAAAAGTCAAGGAGTTTGTGGCTTCTCACGGAGGTCATAC

```
AGTTATCAACAAGGTGAGTATTTGACGTTTAGACTGTATAACAGGCGGCC
GCAGTGCAACAACGACCAAAAAGGGTCGAAAAAGGGTCGAAAACGGACAC
AAAAGCTGGAAAACAAGAGTGTAATACATTCTTACACGTCCAATTGTTAG
ACAAACACGGCTGTTCGGTCCCAAAACCACCAGTATCACCTATTTTCCAC
TTGTGTCTCGGATCTGATCATAATCTGATCTCAAGATGAAATTTACGCCA
CCGACATGATATTGTGATTTTCGGATTCTCCAGACCGAGCAGATTCCAGC
AATACCACCACTTGCCCACCTTCAGCGGCCTCTCGGCGCGATTCGCCACT
TTCCCCAACGAGTGTTACTAACCCAGGTCCTCATCGCTAACAACGGTATT
GCCGCAGTAAAGGAGATCCGTTCAGTACGAAAATGGGCCTACGAGACCTT
TGGCGACGAGCGAGCAATCTCGTTCACCGTCATGGCCACCCCCGAAGATC
TCGCTGCCAACGCCGACTACATTAGAATGGCCGATCAGTACGTCGAGGTG
CCCGAGGAACCAACAACAACAACTACGCCAACGTCGAGCTGATTGTCGA
CGTGGCTGAGCGATTCGGCGTCGATGCCGTGTGGGCCGGATGGGGCCATG
CCAGTGAAAATCCCCTGCTCCCCGAGTCGCTAGCGGCCTCTCCCCGCAAG
ATTGTCTTCATCGGCCCTCCCGGAGCTGCCATGAGATCTCTGGGAGACAA
AATTTCTTCTACCATTGTGGCCCAGCACGCAAAGGTCCCGTGTATCCCGT
GGTCTGGAACCGGAGTGGACGAGGTTGTGGTTGACAAGAGCACCAACCTC
GTGTCCGTGTCCGAGGAGGTGTACACCAAGGGCTGCACCACCGGTCCCAA
GCAGGGTCTGGAGAAGGCTAAGCAGATTGGATTCCCCGTGATGATCAAGG
CTTCCGAGGGAGGAGGAGGAAAGGGTATTCGAAAGGTTGAGCGAGAGGAG
GACTTCGAGGCTGCTTACCACCAGGTCGAGGGAGAGATCCCCGGCTCGCC
CATCTTCATTATGCAGCTTGCAGGCAATGCCCGGCATTTGGAGGTGCAGC
TTCTGGCTGATCAGTACGGCAACAATATTTCACTGTTTGGTCGAGATTGT
TCGGTTCAGCGACGGCATCAAAAGATTATTGAGGAGGCTCCTGTGACTGT
GGCTGGCCAGCAGACCTTCACTGCCATGGAGAAGGCTGCCGTGCGACTCG
GTAAGCTTGTCGGATATGTCTCTGCAGGTACCGTTGAATATCTGTATTCC
CATGAGGACGACAAGTTCTACTTCTTGGAGCTGAATCCTCGTCTTCAGGT
CGAACATCCTACCACCGAGATGGTCACCGGTGTCAACCTGCCCGCTGCCC
AGCTTCAGATCGCCATGGGTATCCCCCTCGATCGAATCAAGGACATTCGT
CTCTTTTACGGTGTTAACCCTCACACCACCACTCCAATTGATTTCGACTT
CTCGGGCGAGGATGCTGATAAGACACAGCGACGTCCCGTCCCCGAGGTC
ACACCACTGCTTGCCGAATCACATCCGAGGACCCTGGAGAGGGTTTCAAG
CCCTCCGGAGGTACTATGCACGAGCTCAACTTCCGATCCTCGTCAACGT
GTGGGGTTACTTCTCCGTTGGTAACCAGGGAGGTATCCATTCGTTCTCGG
ATTCGCAGTTTGGTCACATCTTCGCCTTCGGTGAGAACCGAAGTGCGTCT
CGAAAGCACATGGTTGTTGCTTTGAAGGAACTATCTATTCGAGGTGACTT
CCGAACCACCGTCGAGTACCTCATCAAGCTGCTGGAGACACCGGACTTCG
AGGACAACACCATCACCACCGGCTGGCTGGATGAGCTTATCTCCAACAAG
CTGACTGCCGAGCGACCCGACTCGTTCCTCGCTGTTGTTTGTGGTGCTGC
TACCAAGGCCCATCGAGCTTCCGAGGACTCTATTGCCACCTACATGGCTT
```

```
CGCTAGAGAAGGGCCAGGTCCCTGCTCGAGACATTCTCAAGACCCTTTTC
CCCGTTGACTTCATCTACGAGGGCCAGCGGTACAAGTTCACCGCCACCCG
GTCGTCTGAGGACTCTTACACGCTGTTCATCAACGGTTCTCGATGCGACA
TTGGAGTTAGACCTCTTTCTGACGGTGGTATTCTGTGTCTTGTAGGTGGG
AGATCCCACAATGTCTACTGGAAGGAGGAGGTTGGAGCCACGCGACTGTC
TGTTGACTCCAAGACCTGCCTTCTCGAGGTGGAGAACGACCCCACTCAGC
TTCGATCTCCCTCTCCCGGTAAGCTGGTTAAGTTCCTGGTCGAGAACGGC
GACCACGTGCGAGCCAACCAGCCCTATGCCGAGATTGAGGTCATGAAGAT
GTACATGACTCTCACTGCTCAGGAGGACGGTATTGTCCAGCTGATGAAGC
AGCCCGGTTCCACCATCGAGGCTGGCGACATCCTCGGTATCTTGGCCCTT
GATGATCCTTCCAAGGTCAAGCATGCCAAGCCCTTTGAGGGCCAGCTTCC
CGAGCTTGGACCCCCCACTCTCAGCGGTAACAAGCCTCATCAGCGATACG
AGCACTGCCAGAACGTGCTCCATAACATTCTGCTTGGTTTCGATAACCAG
GTGGTGATGAAGTCCACTCTTCAGGAGATGGTTGGTCTGCTCCGAAACCC
TGAGCTTCCTTATCTCCAGTGGGCTCATCAGGTGTCTTCTCTGCACACCC
GAATGAGCGCCAAGCTGGATGCTACTCTTGCTGGTCTCATTGACAAGGCC
AAGCAGCGAGGTGGCGAGTTTCCTGCCAAGCAGCTTCTGCGAGCCCTTGA
GAAGGAGGCGAGCTCTGGCGAGGTCGATGCGCTCTTCCAGCAAACTCTTG
CTCCTCTGTTTGACCTTGCTCGAGAGTACCAGGACGGTCTTGCTATCCAC
GAGCTTCAGGTTGCTGCAGGCCTTCTGCAGGCCTACTACGACTCTGAGGC
CCGGTTCTGCGGACCCAACGTACGTGACGAGGATGTCATTCTCAAGCTTC
GAGAGGAGAACCGAGATTCTCTTCGAAAGGTTGTGATGGCCCAGCTGTCT
CATTCTCGAGTCGGAGCCAAGAACAACCTTGTGCTGGCCCTTCTCGATGA
ATACAAGGTGGCCGACCAGGCTGGCACCGACTCTCCTGCCTCCAACGTGC
ACGTTGCAAAGTACTTGCGACCTGTGCTGCAAAGATTGTGGAGCTGGAA
TCTCGAGCTTCTGCCAAGGTATCTCTGAAAGCCCGAGAGATTCTCATCCA
GTGCGCTCTGCCCTCTCTAAAGGAGCGAACTGACCAGCTTGAGCACATTC
TGCGATCTTCTGTCGTCGAGTCTCGATACGGAGAGGTTGGTCTGGAGCAC
CGAACTCCCCGAGCCGATATTCTCAAGGAGGTTGTCGACTCCAAGTACAT
TGTCTTTGATGTGCTTGCCCAGTTCTTTGCCCACGATGATCCCTGGATCG
TCCTTGCTGCCCTGGAGCTGTACATCCGACGAGCTTGCAAGGCCTACTCC
ATCCTGGACATCAACTACCACCAGGACTCGGACCTGCCTCCCGTCATCTC
GTGGCGATTTAGACTGCCTACCATGTCGTCTGCTTTGTACAACTCAGTAG
TGTCTTCTGGCTCCAAAACCCCCACTTCCCCCTCGGTGTCTCGAGCTGAT
TCCGTCTCCGACTTTTCGTACACCGTTGAGCGAGACTCTGCTCCCGCTCG
AACCGGAGCGATTGTTGCCGTGCCTCATCTGGATGATCTGGAGGATGCTC
TGACTCGTGTTCTGGAGAACCTGCCCAAACGGGGCGCTGGTCTTGCCATC
TCTGTTGGTGCTAGCAACAAGAGTGCCGCTGCTTCTGCTCGTGACGCTGC
TGCTGCTGCCGCTTCATCCGTTGACACTGGCCTGTCCAACATTTGCAACG
TTATGATTGGTCGGGTTGATGAGTCTGATGACGACGACACTCTGATTGCC
CGAATCTCCCAGGTCATTGAGGACTTTAAGGAGGACTTTGAGGCCTGTTC
```

-continued

```
TCTGCGACGAATCACCTTCTCCTTCGGCAACTCCCGAGGTACTTATCCCA
AGTATTTCACGTTCCGAGGCCCCGCATACGAGGAGGACCCCACTATCCGA
CACATTGAGCCTGCTCTGGCCTTCCAGCTGGAGCTCGCCCGTCTGTCCAA
CTTCGACATCAAGCCTGTCCACACCGACAACCGAAACATCCACGTGTACG
AGGCTACTGGCAAGAACGCTGCTTCCGACAAGCGGTTCTTCACCCGAGGT
ATCGTACGACCTGGTCGTCTTCGAGAGAACATCCCCACCTCGGAGTATCT
CATTTCCGAGGCTGACCGGCTCATGAGCGATATTTTGGACGCTCTAGAGG
TGATTGGAACCACCAACTCGGATCTCAACCACATTTTCATCAACTTCTCA
GCCGTCTTTGCTCTGAAGCCCGAGGAGGTTGAAGCTGCCTTTGGCGGTTT
CCTGGAGCGATTTGGCCGACGTCTGTGGCGACTTCGAGTCACCGGTGCCG
AGATCCGAATGATGGTATCCGACCCCGAAACTGGCTCTGCTTTCCCTCTG
CGAGCAATGATCAACAACGTCTCTGGTTACGTTGTGCAGTCTGAGCTGTA
CGCTGAGGCCAAGAACGACAAGGGCCAGTGGATTTTCAAGTCTCTGGGCA
AGCCCGGCTCCATGCACATGCGGTCTATCAACACTCCCTACCCCACCAAG
GAGTGGCTGCAGCCCAAGCGGTACAAGGCCCATCTGATGGGTACCACCTA
CTGCTATGACTTCCCCGAGCTGTTCCGACAGTCCATTGAGTCGGACTGGA
AGAAGTATGACGGCAAGGCTCCCGACGATCTCATGACTTGCAACGAGCTG
ATTCTCGATGAGGACTCTGGCGAGCTGCAGGAGGTGAACCGAGAGCCCGG
CGCCAACAACGTCGGTATGGTTGCGTGGAAGTTTGAGGCCAAGACCCCCG
AGTACCCTCGAGGCCGATCTTTCATCGTGGTGGCCAACGATATCACCTTC
CAGATTGGTTCGTTTGGCCCTGCTGAGGACCAGTTCTTCTTCAAGGTGAC
GGAGCTGGCTCGAAAGCTCGGTATTCCTCGAATCTATCTGTCTGCCAACT
CTGGTGCTCGAATCGGCATTGCTGACGAGCTCGTTGGCAAGTACAAGGTT
GCGTGGAACGACGAGACTGACCCCTCCAAGGGCTTCAAGTACCTTTACTT
CACCCCTGAGTCTCTTGCCACCCTCAAGCCCGACACTGTTGTCACCACTG
AGATTGAGGAGGAGGGTCCCAACGGCGTGGAGAAGCGTCATGTGATCGAC
TACATTGTCGGAGAGAAGGACGGTCTCGGAGTCGAGTGTCTGCGGGGCTC
TGGTCTCATTGCAGGCGCCACTTCTCGAGCCTACAAGGATATCTTCACTC
TCACTCTTGTCACCTGTCGATCCGTTGGTATCGGTGCTTACCTTGTTCGT
CTTGGTCAACGAGCCATCCAGATTGAGGGCCAGCCCATCATTCTCACTGG
TGCCCCCGCCATCAACAAGCTGCTTGGTCGAGAGGTCTACTCTTCCAACT
TGCAGCTTGGTGGTACTCAGATCATGTACAACAACGGTGTGTCTCATCTG
ACTGCCCGAGATGATCTCAACGGTGTCCACAAGATCATGCAGTGGCTGTC
ATACATCCTGCTTCTCGAGGTCTTCCAGTGCCTGTTCTCCCTCACAAGA
CCGATGTGTGGGATCGAGACGTGACGTTCCAGCCTGTCCGAGGCGAGCAG
TACGATGTTAGATGGCTTATTTCTGGCCGAACTCTCGAGGATGGTGCTTT
CGAGTCTGGTCTCTTTGACAAGGACTCTTTCCAGGAGACTCTGTCTGGCT
GGGCCAAGGGTGTTGTTGTTGGTCGAGCTCGTCTTGGCGGCATTCCCTTC
GGTGTCATTGGTGTCGAGACTGCGACCGTCGACAATACTACCCCTGCCGA
TCCCGCCAACCCGGACTCTATTGAGATGAGCACCTCTGAAGCCGGCCAGG
TTTGGTACCCCAACTCGGCCTTCAAGACCTCTCAGGCCATCAACGACTTC
AACCATGGTGAGGCGCTTCCTCTCATGATTCTTGCTAACTGGCGAGGCTT
TTCTGGTGGTCAGCGAGACATGTACAATGAGGTTCTCAAGTACGGATCTT
TCATTGTTGATGCTCTGGTTGACTACAAGCAGCCCATCATGGTGTACATC
CCTCCCACCGGTGAGCTGCGAGGTGGTTCTTGGGTTGTGGTTGACCCCAC
CATCAACTCGGACATGATGGAGATGTACGCTGACGTCGAGTCTCGAGGTG
GTGTGCTGGAGCCCGAGGGAATGGTCGGTATCAAGTACCGACGAGACAAG
CTACTGGACACCATGGCTCGTCTGGATCCCGAGTACTCCTCTCTCAAGAA
GCAGCTTGAGGAGTCTCCCGATTCTGAGGAGCTCAAGGTCAAGCTCAGCG
TGCGAGAGAAGTCTCTCATGCCCATCTACCAGCAGATCTCCGTGCAGTTT
GCCGACTTGCATGACCGAGCTGGCCGAATGGAGGCCAAGGGTGTCATTCG
TGAGGCTCTTGTGTGGAAGGATGCTCGTCGATTCTTCTTCTGGCGAATCC
GACGACGATTAGTCGAGGAGTACCTCATTACCAAGATCAATAGCATTCTG
CCCTCTTGCACTCGGCTTGAGTGTCTGGCTCGAATCAAGTCGTGGAAGCC
TGCCACTCTTGATCAGGGCTCTGACCGGGGTGTTGCCGAGTGGTTTGACG
AGAACTCTGATGCCGTCTCTGCTCGACTCAGCGAGCTCAAGAAGGACGCT
TCTGCCCAGTCGTTTGCTTCTCAACTGAGAAAGGACCGACAGGGTACTCT
CCAGGGCATGAAGCAGGCTCTCGCTTCTCTTTCTGAGGCTGAGCGGGCTG
AGCTGCTCAAGGGGTTGTGA
```

>gi|50548503|ref|XP_501721.1|YALI0C11407p
[Yarrowia lipolytica]
(SEQ ID NO: 12)

MRLQLRTLTRRFFSMASGSSTPDVAPLVDPNIHKGLASHFFGLNSVHTAK
PSKVKEFVASHGGHTVINKVLIANNGIAAVKEIRSVRKWAYETFGDERAI
SFTVMATPEDLAANADYIRMADQYVEVPGGTNNNNYANVELIVDVAERFG
VDAVWAGWGHASENPLLPESLAASPRKIVFIGPPGAAMRSLGDKISSTIV
AQHAKVPCIPWSGTGVDEVVVDKSTNLVSVSEEVYTKGCTTGPKQGLEKA
KQIGFPVMIKASEGGGGKGIRKVEREEDFEAAYHQVEGEIPGSPIFIMQL
AGNARHLEVQLLADQYGNNISLFGRDCSVQRRHQKIIEEAPVTVAGQQTF
TAMEKAAVRLGKLVGYVSAGTVEYLYSHEDDKFYFLELNPRLQVEHPTTE
MVTGVNLPAAQLQIAMGIPLDRIKDIRLFYGVNPHTTTPIDFDFSGEDAD
KTQRRPVPRGHTTACRITSEDPGEGFKPSGGTMHELNFRSSSNVWGYFSV
GNQGGIHSFSDSQFGHIFAFGENRSASRKHMVVALKELSIRGDFRTTVEY
LIKLLETPDFEDNTITTGWLDELISNKLTAERPDSFLAVVCGAATKAHRA
SEDSIATYMASLEKGQVPARDILKTLFPVDFIYEGQRYKFTATRSSEDSY
TLFINGSRCDIGVRPLSDGGILCLVGGRSHNVYWKEEVGATRLSVDSKTC
LLEVENDPTQLRSPSPGKLVKFLVENGDHVRANQPYAEIEVMKMYMTLTA
QEDGIVQLMKQPGSTIEAGDILGILALDDPSKVKHAKPFEGQLPELGPPT
LSGNKPHQRYEHCQNVLHNILLGFDNQVVMKSTLQEMVGLLRNPELPYLQ
WAHQVSSLHTRMSAKLDATLAGLIDKAKQRGGEFPAKQLLRALEKEASSG
EVDALFQQTLAPLFDLAREYQDGLAIHELQVAAGLLQAYYDSEARFCGPN
VRDEDVILKLREENRDSLRKVVMAQLSHSRVGAKNNLVLALLDEYKVADQ

-continued

```
AGTDSPASNVHVAKYLRPVLRKIVELESRASAKVSLKAREILIQCALPSL

KERTDQLEHILRSSVVESRYGEVGLEHRTPRADILKEVVDSKYIVFDVLA

QFFAHDDPWIVLAALELYIRRACKAYSILDINYHQDSDLPPVISWRFRLP

TMSSALYNSVVSSGSKTPTSPSVSRADSVSDFSYTVERDSAPARTGAIVA

VPHLDDLEDALTRVLENLPKRGAGLAISVGASNKSAAASARDAAAAASS

VDTGLSNICNVMIGRVDESDDDDTLIARISQVIEDFKEDFEACSLRRITF

SFGNSRGTYPKYFTFRGPAYEEDPTIRHIEPALAFQLELARLSNFDIKPV

HTDNRNIHVYEATGKNAASDKRFFTRGIVRPGRLRENIPTSEYLISEADR

LMSDILDALEVIGTTNSDLNHIFINFSAVFALKPEEVEAAFGGFLERFGR

RLWRLRVTGAEIRMMVSDPETGSAFPLRAMINNVSGYVVQSELYAEAKND

KGQWIFKSLGKPGSMHMRSINTPYPTKEWLQPKRYKAHLMGTTYCYDFPE

LFRQSIESDWKKYDGKAPDDLMTCNELILDEDSGELQEVNREPGANNVGM

VAWKFEAKTPEYPRGRSFIVVANDITFQIGSFGPAEDQFFFKVTELARKL

GIPRIYLSANSGARIGIADELVGKYKVAWNDETDPSKGFKYLYFTPESLA

TLKPDTVVTTEIEEEGPNGVEKRHVIDYIVGEKDGLGVECLRGSGLIAGA

TSRAYKDIFTLTLVTCRSVGIGAYLVRLGQRAIQIEGQPIILTGAPAINK

LLGREVYSSNLQLGGTQIMYNNGVSHLTARDDLNGVHKIMQWLSYIPASR

GLPVPVLPHKTDVWDRDVTFQPVRGEQYDVRWLISGRTLEDGAFESGLFD

KDSFQETLSGWAKGVVVGRARLGGIPFGVIGVETATVDNTTPADPANPDS

IEMSTSEAGQVWYPNSAFKTSQAINDFNHGEALPLMILANWRGFSGGQRD

MYNEVLKYGSFIVDALVDYKQPIMVYIPPTGELRGGSWVVVDPTINSDMM

EMYADVESRGGVLEPEGMVGIKYRRDKLLDTMARLDPEYSSLKKQLEESP

DSEELKVKLSVREKSLMPIYQQISVQFADLHDRAGRMEAKGVIREALVWK

DARRFFFWRIRRRLVEEYLITKINSILPSCTRLECLARIKSWKPATLDQG

SDRGVAEWFDENSDAVSARLSELKKDASAQSFASQLRKDRQGTLQGMKQA

LASLSEAERAELLKGL.
```

Some aspects of this invention provide a method for the manipulation of the activity of a stearoyl-CoA-desaturase (SCD) in a microbe for biofuel or biofuel precursor production. SCD is a Δ9 desaturase that inserts a double bond between C9 and C10 of stearic acid coupled to CoA, a key step in the generation of desaturated fatty acids and their derivatives, as described in more detail elsewhere herein. In some embodiments, the manipulation is an overexpression. In some embodiments, the manipulation is effected by contacting a microbe for biofuel or biofuel precursor production with an expression construct comprising a nucleic acid coding for a SCD gene product, for example, a SCD protein, operably linked to a heterologous promoter, for example, a constitutive or an inducible promoter. In some embodiments, the nucleic acid coding for an SCD gene product comprises the coding sequence of SEQ ID NO: 13. In some embodiments, the SCD is *Y. lipolytica* SCD, for example, *Y. lipolytica* SCD comprising the amino acid sequence of SEQ ID NO: 14. In some embodiments, the microbe is *Y. lipolytica*. In some embodiments, manipulation of the activity of a SCD in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. Stearoyl-CoA Desaturase gene and gene product sequences are well known to those of skill in the art. Exemplary, representative gene and gene product sequences can be found under the entry for GeneID: 852825 in the NCBI database (www.ncbi.nlm.nih.gov).

Non-limiting examples of suitable sequences of SCD nucleic acid and protein sequences are provided below. Additional suitable SCD sequences, including sequences from other species, will be apparent to those of skill in the art, and the invention is not limited in this respect.

```
>gi|50548052|ref|XM_501496.1| Yarrowia lipolytica
YALI0C05951p (YALI0C05951g) mRNA, complete cds
                                       (SEQ ID NO: 13)
ATGGTGAAAAACGTGGACCAAGTGGATCTCTCGCAGGTCGACACCATTGC

CTCCGGCCGAGATGTCAACTACAAGGTCAAGTACACCTCCGGCGTTAAGA

TGAGCCAGGGCGCCTACGACGACAAGGGCCGCCACATTTCCGAGCAGCCC

TTCACCTGGGCCAACTGGCACCAGCACATCAACTGGCTCAACTTCATTCT

GGTGATTGCGCTGCCTCTGTCGTCCTTTGCTGCCGCTCCCTTCGTCTCCT

TCAACTGGAAGACCGCCGCGTTTGCTGTCGGCTATTACATGTGCACCGGT

CTCGGTATCACCGCCGGCTACCACCGAATGTGGGCCCATCGAGCCTACAA

GGCCGCTCTGCCCGTTCGAATCATCCTTGCTCTGTTTGGAGGAGGAGCTG

TCGAGGGCTCCATCCGATGGTGGGCCTCGTCTCACCGAGTCCACCACCGA

TGGACCGACTCCAACAAGGACCCTTACGACGCCCGAAAGGGATTCTGGTT

CTCCCACTTTGGCTGGATGCTGCTTGTGCCCAACCCCAAGAACAAGGGCC

GAACTGACATTTCTGACCTCAACAACGACTGGGTTGTCCGACTCCAGCAC

AAGTACTACGTTTACGTTCTCGTCTTCATGGCCATTGTTCTGCCCACCCT

CGTCTGTGGCTTTGGCTGGGGCGACTGGAAGGGAGGTCTTGTCTACGCCG

GTATCATGCGATACACCTTTGTGCAGCAGGTGACTTTCTGTGTCAACTCC

CTTGCCCACTGGATTGGAGAGCAGCCCTTCGACGACCGACGAACTCCCCG

AGACCACGCTCTTACCGCCCTGGTCACCTTTGGAGAGGGCTACCACAACT

TCCACCACGAGTTCCCCTCGGACTACCGAAACGCCCTCATCTGGTACCAG

TACGACCCCACCAAGTGGCTCATCTGGACCCTCAAGCAGGTTGGTCTCGC

CTGGGACCTCCAGACCTTCTCCCAGAACGCCATCGAGCAGGGTCTCGTGC

AGCAGCGACAGAAGAAGCTGGACAAGTGGCGAAACAACCTCAACTGGGGT

ATCCCCATTGAGCAGCTGCCTGTCATTGAGTTTGAGGAGTTCCAAGAGCA

GGCCAAGACCCGAGATCTGGTTCTCATTTCTGGCATTGTCCACGACGTGT

CTGCCTTTGTCGAGCACCACCCTGGTGGAAAGGCCCTCATTATGAGCGCC

GTCGGCAAGGACGGTACCGCTGTCTTCAACGGAGGTGTCTACCGACACTC

CAACGCTGGCCACAACCTGCTTGCCACCATGCGAGTTTCGGTCATTCGAG

GCGGCATGGAGGTTGAGGTGTGGAAGACTGCCCAGAACGAAAAGAAGGAC

CAGAACATTGTCTCCGATGAGAGTGGAAACCGAATCCACCGAGCTGGTCT

CCAGGCCACCCGGGTCGAGAACCCCGGTATGTCTGGCATGGCTGCTTAG
```

-continued

\>gi|50548053|ref|XP_501496.1|YALI0C05951p
[*Yarrowia lipolytica*]

(SEQ ID NO: 14)

MVKNVDQVDLSQVDTIASGRDVNYKVKYTSGVKMSQGAYDDKGRHISEQP

FTWANWHQHINWLNFILVIALPLSSFAAAPFVSFNWKTAAFAVGYYMCTG

LGITAGYHRMWAHRAYKAALPVRIILALFGGGAVEGSIRWWASSHRVHHR

WTDSNKDPYDARKGFWFSHFGWMLLVPNPKNKGRTDISDLNNDWVVRLQH

KYYVYVLVFMAIVLPTLVCGFGWGDWKGGLVYAGIMRYTFVQQVTFCVNS

LAHWIGEQPFDDRRTPRDHALTALVTFGEGYHNFHHEFPSDYRNALIWYQ

YDPTKWLIWTLKQVGLAWDLQTFSQNAIEQGLVQQRQKKLDKWRNNLNWG

IPIEQLPVIEFEEFQEQAKTRDLVLISGIVHDVSAFVEHHPGGKALIMSA

VGKDGTAVFNGGVYRHSNAGHNLLATMRVSVIRGGMEVEVWKTAQNEKKD

QNIVSDESGNRIHRAGLQATRVENPGMSGMAA

Some aspects of this invention provide a method for the manipulation of the activity of an ATP-citrate lyase (ACL) in a microbe for biofuel or biofuel precursor production. ACL provides cytosolic acetyl-CoA by cleaving citrate which is shuttled out of the mitochondria as a product of the TCA cycle. Cleaving citrate into oxaloacetate and acetyl-CoA, ACL gene products provide an acetyl-CoA substrate for ACC, which then mediates the conversion of acetyl-CoA, the main C2-precursor in fatty acid synthesis, to malonyl-CoA, which is considered the first committed step in fatty acid synthesis, as described in more detail elsewhere herein. In some embodiments, an ACL gene product is a protein composed of two subunits encoded by separate genes. In some embodiments, an ACL gene product is composed of two subunits encoded by the same gene. In some embodiments, the manipulation is an overexpression. In some embodiments, the manipulation is effected by contacting a microbe for biofuel or biofuel precursor production with an expression construct comprising a nucleic acid coding for an ACL gene product, for example, an ACL protein, operably linked to a heterologous promoter, for example, a constitutive or an inducible promoter. In some embodiments, the nucleic acid coding for an ACL gene product comprises the coding sequences of SEQ ID NO: 15 and SEQ ID NO: 17. In some embodiments, the ACL is *Y. lipolytica* ACL, for example, *Y. lipolytica* ACL comprising the amino acid sequences of SEQ ID NO: 16 and SEQ ID NO: 18. In some embodiments, the microbe is *Y. lipolytica*. In some embodiments, manipulation of the activity of a ACL in a microbe is effected to confer a beneficial phenotype for large-scale carbohydrate to lipid conversion, for example increased lipid synthesis rate, increased carbohydrate to lipid conversion efficiency, increased lipid storage and, increased growth rate, increased tolerance to elevated concentrations of a carbon source or a lipid product. ATP-citrate lyase gene and gene product sequences are well known to those of skill in the art. Exemplary, representative gene and gene product sequences can be found under the entry for GeneID: 2912101 and 2910381 in the NCBI database (www.ncbi.nlm.nih.gov).

Non-limiting examples of suitable sequences of ACL nucleic acid and protein sequences are provided below. Additional suitable ACL sequences, including sequences from other species, will be apparent to those of skill in the art, and the invention is not limited in this respect.

ATP Citrate Lyase (*Yarrowia lipolytica*) subunit 1,
ACL1 DNA
YALI0E34793g
XM_504787

(SEQ ID NO: 15)
ATGTCTGCCAACGAGAACATCTCCCGATTCGACGCCCCTGTGGGCAAGGA

GCACCCCGCCTACGAGCTCTTCCATAACCACACACGATCTTTCGTCTATG

GTCTCCAGCCTCGAGCCTGCCAGGGTATGCTGGACTTCGACTTCATCTGT

AAGCGAGAGAACCCCTCCGTGGCCGGTGTCATCTATCCCTTCGGCGGCCA

GTTCGTCACCAAGATGTACTGGGGCACCAAGGAGACTCTTCTCCCTGTCT

ACCAGCAGGTCGAGAAGGCCGCTGCCAAGCACCCCGAGGTCGATGTCGTG

GTCAACTTTGCCTCCTCTCGATCCGTCTACTCCTCTACCATGGAGCTGCT

CGAGTACCCCCAGTTCCGAACCATCGCCATTATTGCCGAGGGTGTCCCCG

AGCGACGAGCCCGAGAGATCCTCCACAAGGCCCAGAAGAAGGGTGTGACC

ATCATTGGTCCCGCTACCGTCGGAGGTATCAAGCCCGGTTGCTTCAAGGT

TGGAAACACCGGAGGTATGATGGACAACATTGTCGCCTCCAAGCTCTACC

GACCCGGCTCCGTTGCCTACGTCTCCAAGTCCGGAGGAATGTCCAACGAG

CTGAACAACATTATCTCTCACACCACCGACGGTGTCTACGAGGGTATTGC

TATTGGTGGTGACCGATACCCTGGTACTACCTTCATTGACCATATCCTGC

GATACGAGGCCGACCCCAAGTGTAAGATCATCGTCCTCCTTGGTGAGGTT

GGTGGTGTTGAGGAGTACCGAGTCATCGAGGCTGTTAAGAACGGCCAGAT

CAAGAAGCCCATCGTCGCTTGGGCCATTGGTACTTGTGCCTCCATGTTCA

AGACTGAGGTTCAGTTCGGCCACGCCGGCTCCATGGCCAACTCCGACCTG

GAGACTGCCAAGGCTAAGAACGCCGCCATGAAGTCTGCTGGCTTCTACGT

CCCCGATACCTTCGAGGACATGCCCGAGGTCCTTGCCGAGCTCTACGAGA

AGATGGTCGCCAAGGGCGAGCTGTCTCGAATCTCTGAGCCTGAGGTCCCC

AAGATCCCCATTGACTACTCTTGGGCCCAGGAGCTTGGTCTTATCCGAAA

GCCCGCTGCTTTCATCTCCACTATTTCCGATGACCGAGGCCAGGAGCTTC

TGTACGCTGGCATGCCCATTTCCGAGGTTTTCAAGGAGGACATTGGTATC

GGCGGTGTCATGTCTCTGCTGTGGTTCCGACGACGACTCCCCGACTACGC

CTCCAAGTTTCTTGAGATGGTTCTCATGCTTACTGCTGACCACGGTCCCG

CCGTATCCGGTGCCATGAACACCATTATCACCACCCGAGCTGGTAAGGAT

CTCATTTCTTCCCTGGTTGCTGGTCTCCTGACCATTGGTACCCGATTCGG

AGGTGCTCTTGACGGTGCTGCCACCGAGTTCACCACTGCCTACGACAAGG

GTCTGTCCCCCCGACAGTTCGTTGATACCATGCGAAAGCAGAACAAGCTG

ATTCCTGGTATTGGCCATCGAGTCAAGTCTCGAAACAACCCCGATTTCCG

AGTCGAGCTTGTCAAGGACTTTGTTAAGAAGAACTTCCCCTCCACCCAGC

TGCTCGACTACGCCCTTGCTGTCGAGGAGGTCACCACCTCCAAGAAGGAC

AACCTGATTCTGAACGTTGACGGTGCTATTGCTGTTTCTTTTGTCGATCT

CATGCGATCTTGCGGTGCCTTTACTGTGGAGGAGACTGAGGACTACCTCA

AGAACGGTGTTCTCAACGGTCTGTTCGTTCTCGGTCGATCCATTGGTCTC

```
ATTGCCCACCATCTCGATCAGAAGCGACTCAAGACCGGTCTGTACCGACA

TCCTTGGGACGATATCACCTACCTGGTTGGCCAGGAGGCTATCCAGAAGA

AGCGAGTCGAGATCAGCGCCGGCGACGTTTCCAAGGCCAAGACTCGATCA

TAG
```

ATP Citrate Lyase (Yarrowia lipolytica) subunit 1,
ACL1 Protein
YALI0E34793p
XP_504787

(SEQ ID NO: 16)
```
MSANENISRFDAPVGKEHPAYELFHNHTRSFVYGLQPRACQGMLDFDFIC

KRENPSVAGVIYPFGGQFVTKMYWGTKETLLPVYQQVEKAAAKHPEVDVV

VNFASSRSVYSSTMELLEYPQFRTIAIIAEGVPERRAREILHKAQKKGVT

IIGPATVGGIKPGCFKVGNTGGMMDNIVASKLYRPGSVAYVSKSGGMSNE

LNNIISHTTDGVYEGIAIGGDRYPGTTFIDHILRYEADPKCKIIVLLGEV

GGVEEYRVIEAVKNGQIKKPIVAWAIGTCASMFKTEVQFGHAGSMANSDL

ETAKAKNAAMKSAGFYVPDTFEDMPEVLAELYEKMVAKGELSRISEPEVP

KIPIDYSWAQELGLIRKPAAFISTISDDRGQELLYAGMPISEVFKEDIGI

GGVMSLLWFRRRLPDYASKFLEMVLMLTADHGPAVSGAMNTIITTRAGKD

LISSLVAGLLTIGTRFGGALDGAATEFTTAYDKGLSPRQFVDTMRKQNKL

IPGIGHRVKSRNNPDFRVELVKDFVKKNFPSTQLLDYALAVEEVTTSKKD

NLILNVDGAIAVSFVDLMRSCGAFTVEETEDYLKNGVLNGLFVLGRSIGL

IAHHLDQKRLKTGLYRHPWDDITYLVGQEAIQKKRVEISAGDVSKAKTRS
```

ATP Citrate lyase (Yarrowia lipolytica) subunit 2,
ACL2 DNA
YALI0D24431g
XM_503231

(SEQ ID NO: 17)
```
ATGTCAGCGAAATCCATTCACGAGGCCGACGGCAAGGCCCTGCTCGCACA

CTTTCTGTCCAAGGCGCCCGTGTGGGCCGAGCAGCAGCCCATCAACACGT

TTGAAATGGGCACACCCAAGCTGGCGTCTCTGACGTTCGAGGACGGCGTG

GCCCCCGAGCAGATCTTCGCCGCCGCTGAAAAGACCTACCCCTGGCTGCT

GGAGTCCGGCGCCAAGTTTGTGGCCAAGCCCGACCAGCTCATCAAGCGAC

GAGGCAAGGCCGGCCTGCTGGTACTCAACAAGTCGTGGGAGGAGTGCAAG

CCCTGGATCGCCGAGCGGGCCGCCAAGCCCATCAACGTGGAGGGCATTGA

CGGAGTGCTGCGAACGTTCCTGGTCGAGCCCTTTGTGCCCCACGACCAGA

AGCACGAGTACTACATCAACATCCACTCCGTGCGAGAGGGCGACTGGATC

CTCTTCTACCACGAGGGAGGAGTCGACGTCGGCGACGTGGACGCCAAGGC

CGCCAAGATCCTCATCCCCGTTGACATTGAGAACGAGTACCCCTCCAACG

CCACGCTCACCAAGGAGCTGCTGGCACACGTGCCCGAGGACCAGCACCAG

ACCCTGCTCGACTTCATCAACCGGCTCTACGCCGTCTACGTCGATCTGCA

GTTTACGTATCTGGAGATCAACCCCCTGGTCGTGATCCCCACCGCCCAGG

GCGTCGAGGTCCACTACCTGGATCTTGCCGGCAAGCTCGACCAGACCGCA

GAGTTTGAGTGCGGCCCCAAGTGGGCTGCTGCGCGGTCCCCGCCGCTCT

GGGCCAGGTCGTCACCATTGACGCCGGCTCCACCAAGGTGTCCATCGACG

CCGGCCCCGCCATGGTCTTCCCCGCTCCTTTCGGTCGAGAGCTGTCCAAG

GAGGAGGCGTACATTGCGGAGCTCGATTCCAAGACCGGAGCTTCTCTGAA
```

```
GCTGACTGTTCTCAATGCCAAGGGCCGAATCTGGACCCTTGTGGCTGGTG

GAGGAGCCTCCGTCGTCTACGCCGACGCCATTGCGTCTGCCGGCTTTGCT

GACGAGCTCGCCAACTACGGCGAGTACTCTGGCGCTCCCAACGAGACCCA

GACCTACGAGTACGCCAAAACCGTACTGGATCTCATGACCCGGGGCGACG

CTCACCCCGAGGGCAAGGTACTGTTCATTGGCGGAGGAATCGCCAACTTC

ACCCAGGTTGGATCCACCTTCAAGGGCATCATCCGGGCCTTCCGGGACTA

CCAGTCTTCTCTGCACAACCACAAGGTGAAGATTTACGTGCGACGAGGCG

GTCCCAACTGGCAGGAGGGTCTGCGGTTGATCAAGTCGGCTGGCGACGAG

CTGAATCTGCCCATGGAGATTTACGGCCCCGACATGCACGTGTCGGGTAT

TGTTCCTTTGGCTCTGCTTGGAAAGCGGCCCAAGAATGTCAAGCCTTTTG

GCACCGGACCTTCTACTGAGGCTTCCACTCCTCTCGGAGTTTAA
```

ATP Citrate lyase (Yarrowia lipolytica) subunit 2,
ACL2 Protein
YALI0D24431p
XP_503231

(SEQ ID NO: 18)
```
MSAKSIHEADGKALLAHFLSKAPVWAEQQPINTFEMGTPKLASLTFEDGV

APEQIFAAAEKTYPWLLESGAKFVAKPDQLIKRRGKAGLLVLNKSWEECK

PWIAERAAKPINVEGIDGVLRTFLVEPFVPHDQKHEYYINIHSVREGDWI

LFYHEGGVDVGDVDAKAAKILIPVDIENEYPSNATLTKELLAHVPEDQHQ

TLLDFINRLYAVYVDLQFTYLEINPLVVIPTAQGVEVHYLDLAGKLDQTA

EFECGPKWAAARSPAALGQVVTIDAGSTKVSIDAGPAMVFPAPFGRELSK

EEAYIAELDSKTGASLKLTVLNAKGRIWTLVAGGGASVVYADAIASAGFA

DELANYGEYSGAPNETQTYEYAKTVLDLMTRGDAHPEGKVLFIGGGIANF

TQVGSTFKGIIRAFRDYQSSLHNHKVKIYVRRGGPNWQEGLRLIKSAGDE

LNLPMEIYGPDMHVSGIVPLALLGKRPKNVKPFGTGPSTEASTPLGV
```

Some aspects of this invention provide oleaginous microbes for oil production comprising any of the modifications described herein, for example, in combination with modification of XYL1/XYL2 (and optionally XYL3) or XYLA: a DGA1 modification as described herein, an ACC1 modification as described herein, and/or an SCD modification as described herein. In some embodiments, a modified oleaginous microbe is provided that comprises a push modification as described herein and a pull modification as described herein. In some embodiments, the push modification comprises overexpression of an ACC1 gene product. In some embodiments, the pull modification comprises overexpression of a DGA1 and/or an SCD gene product.

Some aspects of this invention provide nucleic acids coding for a gene product conferring a required and/or desired phenotype for biofuel or biofuel precursor production to a microbe, for example, *Y. lipolytica*. In some embodiments, the nucleic acid encodes an XYL1 gene product, for example, an XYL1 protein. In some embodiments, the nucleic acid encodes an XYL2 gene product, for example, an XYL2 protein. In some embodiments, the nucleic acid encodes an XYL3 gene product, for example, an XYL3 protein. In some embodiments, the nucleic acid encodes an XYLA gene product, for example, an XYLA protein. In some embodiments, the nucleic acid is a nucleic acid derived from *Y. lipolytica*. In some embodiments, the nucleic acid encodes a DGA1 gene product, for example, a DGA1 protein. In some embodiments, the nucleic acid encodes an ACC1 gene product, for example, an ACC1 protein. In some embodiments, the nucleic acid encodes a desaturase, for example a Δ9 desaturase. In some embodiments, the nucleic acid encodes *Y. lipolytica* Δ9 desaturase (SCD). In some embodiments, a nucleic acid is provided that encodes a combination of gene products, for example in multiple cistrons, comprising a gene product the overexpression of which represents a push modification of lipid biosynthesis (e.g., an ACC1 gene product), and a gene product the overexpression of which represents a pull modification of lipid biosynthesis (e.g., a DGA1 and/or SCD gene product).

The term "nucleic acid" refers to a molecule comprising multiple linked nucleotides. "Nucleic acid" and "nucleic acid molecule" are used interchangeably and refer to oligoribonucleotides as well as oligodeoxyribonucleotides. The terms also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) and yeast artificial chromosomes (YACs) can also be used in accordance with some aspects of this invention.

Some aspects of this invention relate to the use of nucleic acid derivatives. The use of certain nucleic acid derivatives may increase the stability of the nucleic acids of the invention by preventing their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages. Nucleic acid derivatives according to some aspects of this invention may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives according to some aspects of this invention may contain substitutions or modifications in the sugars and/or bases. For example, some nucleic acid derivatives may include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine.

In some embodiments, a nucleic acid may comprise a peptide nucleic acid (PNA), a locked nucleic acid (LNA), DNA, RNA, or a co-nucleic acids of the above such as DNA-LNA co-nucleic acid.

As used herein the term "isolated nucleic acid molecule" refers to a nucleic acid that is not in its natural environment, for example a nucleic acid that has been (i) extracted and/or purified from a cell or microbe, for example, a bacteria or yeast, by methods known in the art, for example, by alkaline lysis of the host cell and subsequent purification of the nucleic acid, for example, by a silica adsorption procedure; (ii) amplified in vitro, for example, by polymerase chain reaction (PCR); (iii) recombinantly produced by cloning, for example, a nucleic acid cloned into an expression vector; (iv) fragmented and size separated, for example, by enzymatic digest in vitro or by shearing and subsequent gel separation; or (v) synthesized by, for example, chemical synthesis. In some embodiments, the term "isolated nucleic acid molecule" refers to (vi) an nucleic acid that is chemically markedly different from any naturally occurring nucleic acid. In some embodiments, an isolated nucleic acid can readily be manipulated by recombinant DNA techniques well known in the art. Accordingly, a nucleic acid cloned into a vector, or a nucleic acid delivered to a host cell and integrated into the host genome is considered isolated but a nucleic acid in its native state in its natural host, for example, in the genome of the host, is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein.

Some aspects of this invention relate to nucleic acids encoding a gene product conferring a required or desirable phenotype to a microbe for biofuel or biofuel precursor production which are linked to a promoter or other transcription activating element. In some embodiments, the nucleic acid encoding the gene product and linked to a promoter is comprised in an expression vector or expression construct. As used herein, the terms "expression vector" or "expression construct" refer to a nucleic acid construct, generated recombinantly or synthetically, with a series of specified nucleic acid elements that permit transcription of a particular nucleic acid in a host microbe, for example, an oleaginous yeast. In some embodiments, the expression vector may be part of a plasmid, virus, or nucleic acid fragment. In some embodiments, the expression vector includes the coding nucleic acid to be transcribed operably linked to a promoter. A promoter is a nucleic acid element that facilitates transcription of a nucleic acid to be transcribed. A promoter is typically located on the same strand and upstream (or 5') of the nucleic acid sequence the transcription of which it controls. In some embodiments, the expression vector includes the coding nucleic acid to be transcribed operably linked to a heterologous promoter. A heterologous promoter is a promoter not naturally operably linked to a given nucleic acid sequence. For example, the DGA1 gene in *Y. lipolytica* is naturally operably linked to the *Y. lipolytica* DGA1 gene promoter. Any promoter other than the wildtype *Y. lipolytica* DGA1 gene promoter operably linked to the DGA1 gene, or parts thereof, for example in an expression construct, would, therefore, be a heterologous promoter in this context. For example, a TEF1 promoter linked to a nucleic acid encoding a DGA1 gene product is a heterologous promoter in the DGA1 context.

In some embodiments, the expression vector includes a coding nucleic acid, for example, a nucleic acid encoding a XYL1 and XYL2 (and optionally XYL3) gene product, or a XYLA gene product, and optionally a DGA1, ACC1, and/or SCD gene product, operably linked to a constitutive promoter. The term "constitutive promoter" refers to a promoter that allows for continual transcription of its associated gene. In some embodiments, the expression vector includes a coding nucleic acid, for example, a nucleic acid encoding a XYL1 and XYL2 (and optionally XYL3) gene product, or a XYLA gene product, and optionally a DGA1, ACC1, and/or SCD gene product, operably linked to an inducible promoter. The term "inducible promoter", interchangeably used herein with the term "conditional promoter", refers to a promoter that allows for transcription of its associated gene only in the presence or absence of biotic or abiotic factors. Drug-inducible promoters, for example tetracycline/doxycycline inducible promoters, tamoxifen-inducible promoters, as well as promoters that depend on a recombination event in order to be active, for example the cre-mediated recombination of loxP sites, are examples of inducible promoters that are well known in the art.

Some aspects of this disclosure relate to the surprising discovery that overexpression of a given gene product from a heterologous promoter in oleaginous microbes can be significantly enhanced by including an intron in the respective expression construct. Some aspects of this disclosure provide an intron-enhanced constitutive promoter for gene overexpression in oleaginous microbes and expression constructs and vectors comprising this intron-enhanced promoter. In some embodiments, an intron-enhanced TEF promoter is provided, that comprises a TEF promoter sequence, a transcription start site, an intronic sequence downstream of the transcription start site, and a coding nucleic acid sequence, for example, a nucleic acid sequence encoding a XYL1 and XYL2 (and optionally XYL3) gene product, or a XYLA gene product, and optionally a DGA1, ACC1 and/or SCD gene product. In some embodiments, the intron is positioned downstream of the translation start site, yet within the open reading frame of the gene sequence, e.g., after the start codon, but before the termination site of the nucleic acid sequence encoding the gene product. In some embodiments, the intron is positioned immediately downstream of the translation start site, e.g., an ATG start codon, yet upstream of the remainder of the coding sequence. For illustration purposes, a non-limiting, exemplary structure of an intron-enhanced expression construct is provided as follows:

5'-TEF promoter-transcription start site-intron-XYL1 coding sequence-3'. Another non-limiting, exemplary structure of an intron-enhanced expression construct is provided as follows:

5'-TEF promoter-transcription start site-start codon-intron-XYL1 coding sequence-stop codon-3'. Expression constructs for XYL2, XYL3, XYLA, DGA1, ACC1 and SCD gene products would have the XYL1 coding sequence substituted by an XYL2, XYL3, XYLA, DGA1, ACC or SCD coding sequence, respectively.

Suitable TEF promoter sequences as well as suitable intron sequences will be apparent to those of skill in the art. Some intron-less TEF promoter sequences are disclosed, for example, in U.S. Pat. No. 6,265,185. Some exemplary, representative sequences are provided below. However, it will be understood that the invention is not limited in this respect.

Exemplary TEF Promoter Sequence:

(SEQ ID NO: 19)
agagaccgggttggcggcgcatttgtgtcccaaaaaacagccccaattgc cccaattgaccccaaattgacccagtagcgggcccaaccccggcgagagc cccttctccccacatatcaaacctccccggttcccacacttgccgtta agggcgtagggtactgcagtctggaatctacgcttgttcagactttgtac tagtttctttgtctggccatccgggtaacccatgccggacgcaaaataga ctactgaaaattttttgctttgtggttgggactttagccaagggtataa aagaccaccgtccccgaattacctttcctcttcttttctctctctccttg tcaactcacacccgaaatcgttaagcatttccttctgagtataagaatca ttcaaa Exemplary Intron Sequence:

(SEQ ID NO: 20)
gtgagtttcagaggcagcagcaattgccacgggctttgagcacacggccg ggtgtggtcccattcccatcgacacaagacgccacgtcatccgaccagca cttttttgcagtactaaccgcag Exemplary TEF promoter-intron sequence comprising a start codon (ATG) between the promoter and the intron sequences:

(SEQ ID NO: 21)
agagaccgggttggcggcgcatttgtgtcccaaaaaacagccccaattgc cccaattgaccccaaattgacccagtagcgggcccaaccccggcgagagc cccttctccccacatatcaaacctccccggttcccacacttgccgtta agggcgtagggtactgcagtctggaatctacgcttgttcagactttgtac tagtttctttgtctggccatccgggtaacccatgccggacgcaaaataga ctactgaaaattttttgctttgtggttgggactttagccaagggtataa aagaccaccgtccccgaattacctttcctcttcttttctctctctccttg tcaactcaca<u>cccgaaatcgttaagcatttccttctgagtataagaatca</u>

<u>ttcaaaATGgtgagtttcagaggcagcagcaattgccacgggctttgagc</u>

<u>acacggccgggtgtggtcccattcccatcgacacaagacgccacgtcatc</u>

<u>cgaccagcacttttttgcagtactaaccgcag</u>

Methods to deliver expression vectors or expression constructs into microbes, for example, into yeast cells, are well known to those of skill in the art. Nucleic acids, including expression vectors, can be delivered to prokaryotic and eukaryotic microbes by various methods well known to those of skill in the relevant biological arts. Methods for the delivery of nucleic acids to a microbe in accordance to some aspects of this invention, include, but are not limited to, different chemical, electrochemical and biological approaches, for example, heat shock transformation, electroporation, transfection, for example liposome-mediated transfection, DEAE-Dextran-mediated transfection or calcium phosphate transfection. In some embodiments, a nucleic acid construct, for example an expression construct comprising a combination of XYL1, XYL2, XYL3, XYLA, DGA1, ACC1, and/or SCD encoding nucleic acid sequences, is introduced into the host microbe using a vehicle, or vector, for transferring genetic material. Vectors for transferring genetic material to microbes are well known to those of skill in the art and include, for example, plasmids, artificial chromosomes, and viral vectors. Methods for the construction of nucleic acid constructs, including expression constructs comprising constitutive or inducible heterologous promoters, knockout and knockdown constructs, as well as methods and vectors for the delivery of a nucleic acid or nucleic acid construct to a microbe are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); Christine Guthrie and Gerald R. Fink, *Guide to Yeast Genetics and Molecular and Cell Biology, Part C, Volume* 351, Academic Press; 1st edition (Jul. 9, 2002); Gregory N. Stephanopoulos, Aristos A. Aristidou and Jens Nielsen, *Metabolic Engineering: Principles and Methodologies*, Academic Press; 1 edition (Oct. 16, 1998); and Christina Smolke, *The Metabolic Pathway Engineering Handbook: Fundamentals*, CRC Press; 1 edition (Jul. 28, 2009), all of which are incorporated by reference herein.

In some embodiments, the native promoter of a gene encoding a gene product conferring a required or desirable phenotype to a microbe, for example, the native XYL1, XYL2, XYL3, XYLA, DGA1, ACC1, or SCD promoter, is modified in the microbe to alter the regulation of its transcriptional activity. In some embodiment, the modified promoter exhibits an increased transcriptional activity as compared to its unmodified counterpart. The term "modified promoter", as used herein, refers to a promoter the nucleotide sequence of which has been artificially altered. Nucleotide deletion(s), insertion(s) or mutation(s), alone or in combination, are examples of such artificial alterations. Artificial promoter alterations can be effected in a targeted fashion, for example by homologous recombination approaches, such as gene targeting, knockout, knock in, site-directed mutagenesis, or artificial zinc finger nuclease-mediated strategies. Alternatively, such alterations may be effected by a random or quasi-random event, such as irradiation or non-targeted nucleotide integration and subsequent selection. Promoter modifications, in general, are fashioned in order to modulate the transcriptional activation properties of the respective promoter. For example, the disruption or deletion of a regulatory element mediating the repression of a XYL1, XYL2, XYL3, XYLA, DGA1, ACC1, or SCD promoter in response to elevated intracellular fatty acid levels would lead to continued transcriptional activation of the respective gene even under conditions of elevated intracellular fatty acid levels. Similarly, the insertion of a constitutively active transcriptional activator element into a conditional promoter region may effect overexpression of the respective gene under normally inhibitive conditions. Methods for the targeted disruption of a native promoter, for example, a native XYL1, XYL2, XYL3, XYLA, DGA1, ACC1, or SCD promoter, in a microbe, for example, for targeted disruption resulting in an increased transcription rate, are well known to those of skill in the art.

Some aspects of this invention relate to engineering of a microbe, for example, *Y. lipolytica*, to exhibit a required and/or desirable phenotype for large-scale production of a biofuel or biofuel precursor. Some aspects of this invention relate to the metabolic engineering of the lipid synthesis pathway in order to yield a microbe optimized for biofuel production. Some aspects of this invention relate to metabolic engineering that comprises a combination of genetic modifications modulating the expression of genes regulating carbon flux into a lipid synthesis pathway in order to yield a microbe optimized for biofuel production. In some embodiments, the combination of genetic modifications includes a push modification and a pull modification. In some embodiments, the push modification comprises a genetic modification that increases the level of metabolites, acetyl-CoA, ATP, or NADPH for lipid synthesis in a cell, for example, overexpression of an ACC1 gene product. In some embodiments, the pull modification is a genetic modification that decreases the level of a product or intermediary of lipid synthesis that exhibits a feedback inhibitory function, for example, a fatty acid. In some embodiments, the pull modification comprises overexpression of a DGA1 and/or an SCD gene product.

Engineered Microbes for Biofuel Production

Some aspects of this invention relate to a microbe engineered and/or optimized for large-scale biofuel or biofuel precursor production. In some embodiments, an engineered microbe is provided that has been manipulated by a method or using a nucleic acid or protein provided by some aspects of this invention, for example, an expression construct or a combination of expression constructs as provided herein, resulting in the overexpression of a gene product or a combination of gene products mediating the metabolism of a 5C sugar such as xylose, such as XYL1 and XYL2, and optionally XYL3, or XYLA. In some embodiments, an engineered microbe is provided that has been manipulated by a method or using a nucleic acid or protein provided by some aspects of this invention, for example, an expression construct or a combination of expression constructs as provided herein, resulting in the overexpression of a combination of a gene product mediating a push process of lipid synthesis (e.g., an ACC1 product), and a gene product mediating a pull process of lipid synthesis (e.g., a DGA1 and/or SCD gene product). In some embodiments, an engineered microbe is provided, that overexpresses a push-and-pull combination of gene products that, according to some aspects of this invention, confers a required and/or desirable phenotype for biofuel or biofuel precursor production to the microbe. In some embodiments, a microbe comprising an increased XYL1, XYL2, XYL3, XYLA, DGA1, ACC1, SCD, or ACL gene product activity is provided. In some embodiments, the microbe exhibits an increased fatty acid synthesis rate, an increased TAG storage, and/or an additional required or desirable trait.

In some embodiments, the engineered microbe is an oleaginous yeast, for example, *Y. lipolytica*. In some embodiments, an engineered yeast provided by this invention exhibits one or more highly desirable and unexpected phenotypic characteristics, for example: increased carbon to oil conversion rate or efficiency, increased lipid accumulation in a lipid body.

In some embodiments, the engineered microbe, for example, the engineered yeast, provided by aspects of this invention exhibits a carbon to oil conversion rate within the range of about 0.02 g/g (g oil, lipid, or TAG produced/g Glucose consumed) to about 0.3 g/g. In some embodiments, the engineered microbe, for example, the engineered yeast, provided by aspects of this invention exhibits a carbon to oil conversion of about 0.010 g/g (g TAG produced/g Glucose consumed), about 0.02 g/g, about 0.025 g/g, about 0.03 g/g, about 0.04 g/g, about 0.05 g/g, about 0.06 g/g, about 0.07 g/g, about 0.075 g/g, about 0.08 g/g, about 0.09 g/g, about 0.1 g/g, about 0.11 g/g, about 0.12 g/g, about 0.13 g/g, about 0.14 g/g, about 0.15 g/g, about 0.16 g/g, about 0.17 g/g, about 0.18 g/g, about 0.19 g/g, about 0.2 g/g, about 0.21 g/g, about 0.22 g/g, about 0.23 g/g, about 0.24 g/g, about 0.25 g/g, about 0.26 g/g, about 0.27 g/g, about 0.28 g/g, about 0.29 g/g, about 0.3 g/g, about 0.31 g/g, about 0.32 g/g, or approaching theoretical values. In some embodiments, the engineered microbe, for example, the engineered yeast, provided by aspects of this invention exhibits a carbon to oil conversion rate of at least about 0.010 g/g (g TAG produced/g Glucose consumed), at least about 0.02 g/g, at least about 0.025 g/g, at least about 0.03 g/g, at least about 0.04 g/g, at least about 0.05 g/g, at least about 0.06 g/g, at least about 0.07 g/g, at least about 0.075 g/g, at least about 0.08 g/g, at least about 0.09 g/g, at least about 0.1 g/g, at least about 0.11 g/g, at least about 0.12 g/g, at least about 0.13 g/g, at least about 0.14 g/g, at least about 0.15 g/g, at least about 0.16 g/g, at least about 0.17 g/g, at least about 0.18 g/g, at least about 0.19 g/g, at least about 0.2 g/g, at least about 0.21 g/g, at least about 0.22 g/g, at least about 0.23 g/g, at least about 0.24 g/g, at least about 0.25 g/g, at least about 0.26 g/g, at least about 0.27 g/g, at least about 0.28 g/g, at least about 0.29 g/g, at least about 0.3 g/g, at least about 0.31 g/g, at least about 0.32 g/g, or approaching theoretical values.

Some aspects of this invention provide engineered microbes for oil production that can use a variety of carbon sources, including, but not limited to fermentable sugars, for example, C5 sugars, such as xylose; C6 sugars, such as glucose; organic acids, e.g., acetic acid, and/or their salts, e.g., acetate; polyol compounds, such as glycerol; and sugar alcohols, such as arabitol.

Microbial Cultures for Biofuel Production

Some aspects of this invention relate to cultures of genetically modified microbes provided herein. In some embodiments, the culture comprises a genetically modified microbe provided herein and a medium, for example, a liquid medium. In some embodiments, the culture comprises a genetically modified microbe provided herein and a carbon source, for example, a fermentable carbohydrate source, or an organic acid or salt thereof. In some embodiments, the culture comprises a genetically modified microbe provided herein and a salt and/or buffer establishing conditions of salinity, osmolarity, and pH, that are amenable to survival, growth, and/or carbohydrate to biofuel or biofuel precursor conversion by the microbe. In some embodiments, the culture comprises an additional component, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a drug inducing or inhibiting transcription from a conditional or inducible promoter, for example doxicycline, tetracycline, tamoxifen, IPTG, hormones, or metal ions.

While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); and Christine Guthrie and Gerald R. Fink, *Guide to Yeast Genetics and Molecular and Cell Biology, Part C, Volume* 351, Academic Press; 1st edition (Jul. 9, 2002), all of which are incorporated by reference herein. For oil production, the cultures of engineered microbes described herein are cultured under conditions suitable for oil accumulation, as known in the art.

In some embodiments, the genetically modified microbe exhibits a growth advantage over wild type microbes of the same kind and/or over other microbes, for example, microbes commonly found to contaminate microbial cultures for carbon source to biofuel or biofuel precursor conversion. In some embodiments, the growth and/or proliferation advantage of an engineered microbe provided by aspects of this invention translates into the possibility of using non-sterile culturing and fermentation conditions for biofuel or biofuel precursor production, because the problem of culture overgrowth by contaminating microbes is mitigated or completely abolished. In some embodiments, an engineered microbe provided by aspects of this invention is cultured under non-sterile conditions for biofuel or biofuel precursor production. For example, in some embodiments, non-sterilized feedstock, non-sterilized culture media, non-sterilized supplements, or a non-sterilized bioreactor (e.g. an open reactor under non-sterile conditions) is used for biofuel or biofuel precursor production.

A variety of different microbes can be genetically modified according to some aspects of this invention and used for industrial-scale biofuel or biofuel precursor production, for example, microbes from various sources of yeast, such as oleaginous yeast, bacteria, algae and fungi. Non-limiting examples of suitable yeast cells are cells from *Yarrowia lipolytica, Hansenula polymorpha, Pichia pastoris, Saccharomyces cerevisiae, S. bayanus, S. K. lactis, Waltomyces lipofer. Mortierella alpine, Mortierella isabellina, Hansenula polymorpha., Mucor rouxii, Trichosporon cutaneu, Rhodotorula glutinis Saccharomyces diastasicus, Schwanniomyces occidentalis, S. cerevisiae, Pichia stipitis*, and *Schizosaccharomyces pombe*. Non-limiting examples of suitable bacteria are *Bacillus subtilis, Salmonella, Escherichia coli, Vibrio cholerae, Streptomyces, Pseudomonas fluorescens, Pseudomonas putida, Pseudomonas* sp, *Rhodococcus* sp, *Streptomyces* sp, and *Alcaligenes* sp. Non-limiting examples of suitable fungal cells can, for example, be cultured from species such as *Aspergillus shirousamii, Aspergillus niger* and *Trichoderma reesei*. Non-limiting examples of suitable algal cells are cells from *Neochloris oleoabundans, Scenedesmus obliquus, Nannochloropsis* sp., *Dunaliella tertiolecta, Chlorella vulgaris, Chlorella emersonii,* and *Spirulina maxima*.

Methods for Biofuel Production/Feedstock/Bioreactors

Some aspects of this invention provide methods for the production of biofuel or biofuel precursors using genetically modified microbes provided herein. In some embodiments, methods for biofuel or biofuel precursor production on an industrial scale are provided.

A variety of carbon sources can be converted into a biofuel or biofuel precursor using a method and/or a genetically modified microbe provided herein. In some embodiments, the carbon source comprises a carbohydrate. Sugars, starches, and fibers are non-limiting examples of carbohydrate sources suitable for conversion methods provided herein. According to some aspects of this invention, a carbohydrate source may comprise a refined and/or unrefined sugar, starch, and/or fiber, or a combination of any of these. Non-limiting examples of sugars are fermentable sugars, such as, xylose, glucose, fructose, sucrose and lactose. Non-limiting examples of starches are amylase and amylopectin. Non-limiting examples of fibers are plant fibers, such as cellulose, hemicellulose and wood fibers. Some aspects of this invention relate to the use of industrial byproducts, intermediates, or waste products, for example raw plant extracts, molasses, stover, or sewage as a carbon source. In some embodiments, the carbon source is derived from algae. In some embodiments, algal biomass is produced specifically for use as a carbon source in microbe-mediated biofuel or biofuel precursor production.

In some embodiments, methods for the production of biofuel or biofuel precursor are provided that include the use of a cheap, abundant, and readily available carbon source feedstock as the carbon source. In some embodiments, cellulose or hemicellulose is used as the carbon source. In some embodiments, the cellulose or hemicellulose is derived from industrial by- or waste products. In some embodiments, the cellulose or hemicellulose is derived directly from plant or algal biomass. Plant or algal biomass is one of the most abundant feedstocks and comprises a significant amount of non-fermentable sugars and fibers, for example, cellulose and hemi-cellulose. In some embodiments, biomass feedstock is pretreated to convert a non-fermentable sugar or fiber into a fermentable sugar, thus making them available for microbe growth and microbe-mediated biofuel or biofuel precursor production. In some embodiments, the pretreatment of biomass feedstock includes depolymerizing cellulose and/or hemicellulose components to monomeric sugars using a pretreatment method known to those of skill in the art, for example, a dilute acid or ammonia fiber expansion (AFEX) method (see, e.g., Yang B, Wyman C E. *Dilute acid and autohydrolysis pretreatment*. Methods Mol Biol. 2009; 581:103-14; Balan V, Bals B, Chundawat S P, Marshall D, Dale B E, *Lignocellulosic biomass pretreatment using AFEX Methods* Mol Biol. 2009; 581:61-77). Other methods for depolymerization of biomass polymers to monomeric sugars are well known to those of skill in the art and are contemplated to be used in some embodiments of this invention.

In some embodiments, a biomass feedstock containing non-fermentable sugars is pretreated using a dilute acid method to depolymerize a non-fermentable sugar to a monomeric, fermentable sugar. In some embodiments, biomass is treated with dilute sulphuric acid at moderately mild temperatures for a defined period of time. For example, in some embodiments, the biomass is treated with about 0.5%, about 1%, about 2%, about 3%, about 4%, about 5%, or about 6% sulphuric acid. In some embodiments, the biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C.

In some embodiments, the resulting hydrolysate contains insoluble lignin and solubilized cellulosic and hemicellulosic polymers. The latter products can be further treated to generate hexose and pentose sugars such as glucose and xylose monomers by methods well known to those of skill in the art, for example, by treatment with cellulase or other hydrolyzing enzymes. In some embodiments, the pretreatment of non-fermentable sugars with dilute acid results in the generation of by-products that include toxic compounds which inhibit growth, decrease viability, and/or inhibit biofuel or biofuel precursor production of microbes not engineered according to aspects of this invention. In some embodiments, the pre-treated feedstock is washed, supplemented with media supporting microbial growth and biofuel or biofuel precursor production, and/or over-limed for detoxification.

In some embodiments, a biomass feedstock containing non-fermentable sugars is pretreated using an AFEX method to depolymerize a non-fermentable sugar to a monomeric, fermentable sugar. In some embodiments, biomass is treated with liquid ammonia at high temperature and pressure for a defined period of time. In some embodiments, biomass is treated for about 10 minutes, about 20 minutes, about 30 minutes, about 40 minutes, about 50 minutes, about 60 minutes, about 70 minutes, about 80 minutes, about 90 minutes, or longer. In some embodiments, biomass is treated at about 30° C., at about 37° C., at about 40° C., at about 50° C., at about 60° C., at about 70° C., at about 80° C., at about 90° C., at about 100° C., at about 110° C., at about 120° C., at about 130° C., at about 140° C., at about 150° C., at about 175° C., at about 200° C., or at above about 200° C. In some embodiments, the AFEX pretreatment results in the conversion of crystalline cellulose contained in the feedstock into an amorphous, fermentable form. In some embodiments, the AFEX pre-treated biomass feedstock does not contain significant amounts of toxic byproducts that inhibit microbial growth and/or biofuel or biofuel precursor production, and is used without prior detoxification for microbial biofuel or biofuel precursor production.

In some embodiments, biomass feedstock, with or without pre-treatment, is treated with an enzyme that hydrolyzes or depolymerizes sugar polymers, for example, with a cellulase or hemicellulase enzyme. In some embodiments, the feedstock is contacted with the enzyme in a liquid phase and incubated at a temperature allowing for the enzyme to catalyze a depolymerization or hydrolyzation reaction for a time sufficient to hydrolyze or depolymerize a significant amount of the non-fermentable sugar or fiber in the biomass feedstock. In some embodiments, the liquid phase of the feedstock contacted with the enzyme, which contains the soluble, fermentable sugar fraction, is separated from the solid phase, including non-fermentable sugars and fibers, after incubation for hydrolyzation and depolymerization, for example, by centrifugation. In some embodiments, the liquid fraction of the feedstock is subsequently contacted with a microbe, for example, a microbe provided by aspects of this invention, for conversion to biofuel or biofuel precursor. In some embodiments, enzymatic conversion of non-fermentable sugars or fiber occurs in a consolidated bioprocess, for example, at the same time and/or in the same reactor as microbial conversion of the produced fermentable sugars to biofuel or biofuel precursor. In some embodiments, the enzymatic conversion is performed first, and the feedstock contacted with enzyme is subsequently contacted with the microbe for biofuel or biofuel precursor production. In some embodiments, enzymatic and microbial conversion are performed at the same time and in the same reactor.

In some embodiments, an engineered microbe as provided herein, for example, a *Yarrowia lipolytica* overexpressing a XYL1, XYL2, XYL3, XYLA, DGA1, ACC1, SCD, or ACL gene product, is grown on glycerol. In some embodiments, the genetically modified microbes are intermittently contacted with glycerol. In some embodiments, the microbes are continuously or semi-continuously contacted with glycerol. In some embodiments, the microbes are contacted with glycerol at a concentration of about 0.5%, about 1%, about 2%, about 3%, about 4%, or about 5% vol/vol. Contacting the engineered microbes provided herein with glycerol provides metabolites for the production of TAGs, as well as reducing moieties for the production of fatty acids from carbohydrates. In some embodiments, glycerol spiking or use is performed in biofuel or biofuel precursor production methods in combination with any other carbon source described herein.

In some embodiments, fermentation processes for large-scale microbe-mediated carbohydrate to lipid conversion may be carried out in bioreactors. As used herein, the terms "bioreactor" and "fermentor," which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate a product, for example a biofuel or biofuel precursor, for example a fatty acid and/or TAG, on a commercial or quasi-commercial scale. Large scale bioreactors typically have volumes in the range of liters, hundreds of liters, thousands of liters, or more.

A bioreactor in accordance with aspects of this invention may comprise a microbe or a microbe culture. In some embodiments, a bioreactor may comprise a spore and/or any kind of dormant cell type of any isolated microbe provided by aspects of this invention, for example, in a dry state. In some embodiments, addition of a suitable carbohydrate source to such bioreactors may lead to activation of the dormant cell, for example to germination of a yeast spore, and subsequent conversion of the carbohydrate source, at least in part, to a biofuel or biofuel precursor.

Some bioreactors according to aspects of this invention may include cell culture systems where microbes are in contact with moving liquids and/or gas bubbles. Microbes or microbe cultures in accordance with aspects of this invention may be grown in suspension or attached to solid phase carriers. Non-limiting examples of carrier systems include microcarriers (e.g., polymer spheres, microbeads, and microdisks that can be porous or nonporous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

Industrial-scale carbohydrate to lipid conversion processes in accordance with aspects of this invention may be operated in continuous, semi-continuous or non-continuous modes. Non-limiting examples of operation modes in accordance with this invention are batch, fed batch, extended batch, repetitive batch, draw/fill, rotating-wall, spinning flask, and/or perfusion mode of operation.

In some embodiments, bioreactors may be used that allow continuous or semi-continuous replenishment of the substrate stock, for example a carbohydrate source and/or continuous or semi-continuous separation of the product, for example a secreted lipid, an organic phase comprising a lipid, and/or cells exhibiting a desired lipid content, from the reactor.

Non-limiting examples of bioreactors in accordance with this invention are: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multiwell plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

Bioreactors and fermentors according to aspects of this invention may, optionally, comprise a sensor and/or a control system to measure and/or adjust reaction parameters. Non-limiting examples of reaction parameters are: biological parameters, for example growth rate, cell size, cell number, cell density, cell type, or cell state, chemical parameters, for example pH, redox-potential, concentration of reaction substrate and/or product, concentration of dissolved gases, such as oxygen concentration and CO2 concentration, nutrient concentrations, metabolite concentrations, glucose concentration, glutamine concentration, pyruvate concentration, apatite concentration, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products, physical/mechanical parameters, for example density, conductivity, degree of agitation, pressure, and flow rate, shear stress, shear rate, viscosity, color, turbidity, light absorption, mixing rate, conversion rate, as well as thermodynamic parameters, such as temperature, light intensity/quality etc.

Sensors able to measure parameters as described herein are well known to those of skill in the relevant mechanical and electronic arts. Control systems able to adjust the parameters in a bioreactor based on the inputs from a sensor as described herein are well known to those of skill in the art of bioreactor engineering.

The type of carbon source to be employed for conversion to a biofuel or biofuel precursor according to aspects of this invention depends on the specific microbe employed. Some microbes provided by aspects of this invention may be able to efficiently convert a specific carbohydrate source, while a different carbohydrate source may not be processed by the same microbe at high efficiency or at all. According to aspects of this invention, the modified oleaginous yeast *Y. lipolytica*, for example, can efficiently convert sugars, such as xylose, glucose, fructose, sucrose, and/or lactose, and carbohydrate sources high in sugars, for example molasses, other carbon sources such as glycerol and arabitol, and plant fibers into fatty acids and their derivatives.

In some embodiments, a biofuel or biofuel precursor, for example, a fatty acid or a triacylglycerol, generated from a carbon source feedstock is secreted, at least partially, by a microbe provided by aspects of this invention, for example, an oleaginous yeast, such as a *Y. lipolytica* cell. In some embodiments, a microbe provided by aspects of this invention is contacted with a carbohydrate source in an aqueous solution in a bioreactor, and secreted biofuel or biofuel precursor forms an organic phase that can be separated from the aqueous phase. The term organic phase, as used herein, refers to a liquid phase comprising a non-polar, organic compound, for example a fatty acid, TAG, and/or other non-polar lipid. And organic phase in accordance to this invention might further contain a microbe, a carbohydrate, or other compound found in other phases found in a respective bioreactor. Methods useful for industrial scale phase separation are well known to those of ordinary skill in the art. In some embodiments, the organic phase is continuously or semi-continuously siphoned off. In some embodiments, a bioreactor is employed, comprising a separator, which continuously or semi-continuously extracts the organic phase.

In some embodiments, a biofuel or biofuel precursor is accumulated in cells according to aspects of this invention. In some embodiments, cells that have accumulated a desirable amount of biofuel or biofuel precursor, are separated continuously or semi-continuously from a bioreactor, for example, by centrifugation, sedimentation, or filtration. Cell separation can further be effected, for example, based on a change in physical cell characteristics, such as cell size or density, by methods well known to those skilled in the art. The accumulated biofuel or biofuel precursor can subsequently be extracted from the respective cells using standard methods of extraction well known to those skilled in the art, for example, solvent hexane extraction. In some embodiments, microbial cells are collected and extracted with 3 times the collected cell volume of hexane. In some embodiments, the extracted biofuel or biofuel precursor are further refined. In some embodiments, a biofuel precursor, for example a triacylglycerol is converted to a biofuel, for example, biodiesel, using a method well known to those of skill in the art, for example, a transesterification procedure.

The function and advantage of these and other embodiments of the present invention will be more fully understood from the examples below. The following examples are intended to illustrate the benefits of the present invention, but do not exemplify the full scope of the invention. Accordingly, it will be understood that the example section is not meant to limit the scope of the invention.

EXAMPLES

Example 1

Engineering Xylose Utilization in the Oleaginous Yeast *Yarrowia lipolytica* for Biofuel Production Introduction In the search for improved feedstocks, the push towards cellulosic biofuels is a clear choice. Cellulosic biomass mitigates the need to compete with food crop production; an estimated 1.3+ billion dry tons per year of biomass is potentially available in the US alone (Perlack 2005). Additionally, cellulosic materials can be more efficiently grown and more stably produced compared to sugar crops. However cellulosic materials are not naturally consumable by most biofuel-producing organisms, and thus cellulose requires pretreatment and hydrolysis to break the material down into monomeric sugar. The resulting hydrolysate can then be used as a sugar rich feedstock.

Since hydrolysis of lignocellulosic biomass results in 20-30% carbohydrates in the form of xylose, utilization of pentose sugars is one of the first steps toward efficiently using cellulosic materials. *Saccharomyces cerevisiae*, the most productive of ethanologenic organisms, cannot ferment xylose; it lacks the ability to convert xylose into xylulose, which can then enter the pentose phosphate pathway (PPP). Transferring the xylose reductase (XR or XYL1) and xylitol dehydrogenase (XDH or XYL2) enzymes from *Scheffersomyces stipitis* (formerly *Pichia stipitis*) has been shown to enable growth of the yeast on xylose for production of ethanol (Jeffries 2006). The addition of xylulokinase (XK or XYL3) can also be used to further improve utilization, although *S. cerevisiae* already carries an endogenous version of this gene. A secondary pathway, using xylose isomerase (XYLA), can be used to convert xylose into xylulose. Compared to the XR/XDH redox pathway, which uses NADPH and NAD+ cofactors for shuttling of reducing equivalents, the isomerase pathway requires no cofactors. Nonetheless the redox pathway is much more prevalent in nature, and likewise in literature (Jeffries 2006; Matsushika et al. 2009).

Instead of ethanol production, it may also be advantageous to produce yeast oil for biodiesel from cellulosic feedstocks. As a robust lipid producing organism, *Yarrowia lipolytica* appears to be an attractive platform for the production of cellulosic biodiesel. By leveraging the knowledge and resources developed for xylose metabolic engineering in *S. cerevisiae*, xylose utilization in *Y. lipolytica* enables robust production of yeast oils from cellulosic materials. Because theoretical yields of lipid production from xylose are very similar to that of glucose (0.34 g/g compared to 0.32 g/g), the consumption of xylose represents an attractive and worthwhile opportunity in a developing cellulosic biodiesel microbial bioprocess (Ratledge 1988). Furthermore, *Y. lipolytica* has a very high relative PPP flux (Blank et al. 2005), a phenotype advantageous for growth on xylose since all flux must pass through the PPP. Upregulation of the PPP pathway is a commonly engineered aspect in xylose utilizing *S. cerevisiae* strains (Walfridsson et al. 1995).

For the metabolic conversion of xylose to lipids, xylose enters the cell and can be catabolized either through the redox (XR/XDH) pathway or the isomerase (XYLA) pathway, producing xylulose. It can then enter central metabolism through the non-oxidative pathway of the PPP where it ultimately produces glyceraldehyde-3-phosphate (G3P) and fructose-6-phosphate (F6P). These two products can then enter the rest of central metabolism, going through glycolysis to enter the TCA cycle. Production of lipids occurs normally through the transport of mitochondrial citrate into the cytosol, where it is cleaved by ATP citrate lyase into oxaloacetate and cytosolic acetyl-coA. The acetyl-coA can then enter the fatty acid synthesis pathway through the enzymatic activity of acetyl-coA carboxylase. Acyl-coA generated from the fatty acid synthase complex are transferred to a glycerol-3-phosphate backbone and ultimately sequestered within lipid bodies as triacylglycerol (TAG).

Here we describe the analysis of *Y. lipolytica* for its natural xylose utilization and the metabolic engineering of the organism enabling utilization of xylose for the production of lipids. By incorporation of XR/XDH genes we are able to enable growth on xylose as sole carbon source, and open up opportunities for the production of lipids from cofermentations. Next we study the performance of our engineered strain through the use of cofermentations to analyze for catabolite repression and response, and evaluate the performance of the strain in a scaled-up 2-L bioreactor glycerol-xylose cofermentation with respect to lipid production. Finally we perform transcription analysis to observe the respiratory responses of the organism during cofermentation.

Methods

Yeast Strains, Growth, and Culture Conditions

The *Y. lipolytica* strains used in this study were derived from the wild-type *Y. lipolytica* W29 strain (ATCC20460). The auxotrophic Po1g (Leu-) used in all transformations was obtained from Yeastern Biotech Company (Taipei, Taiwan). All strains used in this study are listed in Table 1. Constructed plasmids were linearized with SacII and chromosomally integrated into Po1g according to the one-step lithium acetate transformation method described by Chen et al. (Chen et al., 1997). MTYL transformants were named after the numbering of their corresponding integrated plasmids. Transformants were plated on selective media and verified by PCR of prepared genomic DNA. Verified transformants were then stored as frozen glycerol stocks at −80° C. and on selective YNB plates at 4° C.

Media and growth conditions for *Escherichia coli* have been previously described by Sambrook et al. (Sambrook and Russell 2001), and those for *Y. lipolytica* have been described by Barth and Gaillardin (Barth and Gaillardin 1997). Rich medium (YPD) was prepared with 20 g/L Bacto peptone (Difco Laboratories, Detroit, Mich.), 10 g/L yeast extract (Difco), 20 g/L glucose (Sigma-Aldrich, St. Louis, Mo.). YNB medium was made with 1.7 g/L yeast nitrogen base (without amino acids) (Difco), 0.69 g/L CSM-Leu (MP Biomedicals, Solon, Ohio), and 20 g/L glucose. Selective YNB plates contained 1.7 g/L yeast nitrogen base (without amino acids), 0.69 g/L CSM-Leu, 20 g/L glucose, and 15 g/L Bacto agar (Difco).

Shake flask experiments were carried out using the following medium: 1.7 g/L yeast nitrogen base (without amino acids), 1.5 g/L yeast extract, and 50 g/L glucose. From frozen stocks, precultures were inoculated into YNB medium (5 mL in Falcon tube, 200 rpm, 28° C., 24 hr). Overnight cultures grown in YPD were centrifuged, washed, and reinoculated into 50 mL of media in 250 mL Erlenmeyer shake flask (200 rpm, 28° C.). OD, biomass and sugar content were taken periodically and analyzed.

For adaptation of strains on xylose, verified transformants were inoculated into shake flasks containing minimal media and 20 g/L xylose. The cultures were incubated at 30° C. for at least 10 days, waiting for growth to occur, before reinoculation into fresh media. This process was repeated until the final OD of the culture reached at least 20, indicating adaptation to xylose. The culture was then stored as frozen stock in 15% glycerol at −80° C. for subsequent use.

Bioreactor scale fermentation was carried out in a 2-liter baffled stirred-tank bioreactor. The medium used contained 1.7 g/L yeast nitrogen base (without amino acids and ammonium sulfate), 2 g/L ammonium sulfate, 1 g/L yeast extract, and 90 g/L glucose. From a selective plate, an initial preculture was inoculated into YPD medium (40 mL in 250 mL Erlenmeyer flask, 200 rpm, 28° C., 24 hr). Exponentially growing cells from the overnight preculture were transferred into the bioreactor to an optical density (A600) of 0.1 in the 2-L reactor (2.5 vvm aeration, pH 6.8, 28° C., 250 rpm agitation). Time point samples were stored at −20° C. for subsequent lipid analysis. Sugar organic acid content was determined by HPLC. Biomass was determined by determined gravimetrically from samples washed and dried at 60° C. for two nights. Lipid content was analyzed by direct transesterification.

Plasmid Construction

Standard molecular genetic techniques were used throughout this study (Sambrook and Russell 2001). Restriction enzymes and Phusion High-Fidelity DNA polymerase used in cloning were obtained from New England Biolabs (Ipswich, Mass.). Genomic DNA from yeast transformants was prepared using Yeastar Genomic DNA kit (Zymo Research, Irvine, Calif.). All constructed plasmids were verified by sequencing. PCR products and DNA fragments were purified with PCR Purification Kit or QIAEX II kit (Qiagen, Valencia, Calif.). Plasmids used are described in Table 1. Primers used are described in Table 2.

Plasmid pMT041 was constructed by amplifying the xylose reductase gene (XYL1; Accession Number: XM_001385144) from *S. stipitis* genomic DNA (ATCC 58376) using the primers MT243 and MT244 and inserting it between the PmlI and BamHI sites of pINA1269. Plasmid pMT044 was constructed by amplifying the xylitol dehydrogenase gene (XYL2; Accession Number: XM_001386945) using the primers MT233 and MT234 and inserting it between the PmlI and BamHI sites of pINA1269. XYL1 and XYL2 are both genes originally from the xylose utilizing yeast, *S. stipitis*.

Plasmid pMT059 was constructed by amplifying the XYL1 gene from pMT041 using the primers MT281 and MT282. The amplicon was then inserted into the TEFin expression plasmid, pMT015 between the sites SnaBI and KpnI.

For the expression of multiple genes on a single plasmid, the promoter-gene-terminator cassette can be amplified from a parent vector using primers MT220 and MT265. The cassette can then be inserted into the receiving vector between the restriction sites NruI and AseI, resulting in a tandem gene construct. The AseI restriction site was selected to facilitate selection, as it resides within the ampicillin resistance marker of the plasmid. Because NruI is a blunt end restriction site, insertion of the amplicon does not increase the total number of NruI sites that helps facilitate progressive insertions. Plasmid pMT081 was constructed by amplifying the XYL2 cassette from pMT044 and inserting it into the plasmid pMT059, containing XYL1. Plasmid pMT085 was constructed by amplifying the DGA cassette from pMT053 and inserting it into the plasmid pMT081, which contains XYL12.

RNA Isolation and Transcript Quantification

Shake flask cultures grown for 42 hrs were collected and centrifuged for 5 min at 10,000 g. Each pellet was resuspended in 1.0 ml of Trizol reagent (Invitrogen) and 100 µL of acid-washed glass beads were added (Sigma-Aldrich). Tubes were vortexed for 15 min at 4° C. for cell lysis to occur. The tubes were then centrifuged for 10 min at 12,000 g at 4° C. and the supernatant was collected in a fresh 2-mL tube. 200 µL chloroform was then added and tubes were shaken by hand for 10 seconds. The tubes were again centrifuged for 10 min at 12,000 g at 4° C. 400 µL of the upper aqueous phase was transferred to a new tube, and an equal volume of phenol-chloroform-isoamyl alcohol (pH 4.7) (Ambion, Austin, Tex.) was added. Tubes were again shaken by hand for 10 seconds and centrifuged for 10 min at 12,000 g at 4° C. 250 µL of the upper phase was transferred to a new tube with an equal volume of cold ethanol and ⅒th volume sodium acetate (pH 5.2). Tubes were chilled at −20° C. for thirty minutes to promote precipitation. Tubes were then centrifuged for 5 min at 12,000 g, washed twice with 70% ethanol, dried in a 60° C. oven and finally resuspended in RNAse free water. RNA quantity was analyzed using a NanoDrop ND-1000 spectrophotometer (NanoDrop Technologies, Wilmington, Del.) and samples were stored in −80° C. freezer. qRT-PCR analyses were carried out using iScript One-step RT-PCR Kit with SYBR Green (Bio-Rad, Hercules, Calif.) using the Bio-Rad iCycler iQ Real-Time PCR Detection System. Fluorescence results were analyzed using Real-time PCR Miner and relative quantification and statistical analysis was determined with REST 2009 (Qiagen) using actin as the reference gene and MTYL038 as the reference strain (Zhao and Fernald 2005). Samples were analyzed in quadruplicate.

TABLE 1

Strains and plasmids used in this study

| Strains (host strain) | Genotype or plasmid | Source |
|---|---|---|
| *E. coli* | | |
| DH5α | fhuA2 Δ(argF-lacZ)U169 phoA glnV44 Φ80 Δ(lacZ)M15 gyrA96 recA1 relA1 endA1 thi-1 hsdR17 | Invitrogen |
| pINA1269 | JMP62-LEU | Yeastern |
| pMT015 | pINA1269 php4d::TEFin | This Example |
| pMT041 | hp4d-XYL1 | This Example |
| pMT044 | hp4d-XYL2 | This Example |
| pMT053 | YTEFin-DGA1 | This Example |
| pMT059 | TEFin-XYL1 | This Example |
| pMT081 | TEFin-XYL1 + hp4d-XYL2 | This Example |
| pMT085 | TEFin-XYL1 + hp4d-XYL2 + TEFin-DGA | This Example |
| *Y. lipolytica* | | |
| Po1g | MATa, leu2-270, ura3-302::URA3, xpr2-332, axp-2 | Yeastern |
| MTYL038 | MATa, leu2-270, ura3-302::URA3, xpr2-332, axp-2 TEF-LacZ-LEU2 | This Example |
| MTYL053 | MATa, leu2-270, ura3-302::URA3, xpr2-332, axp-2 TEFin-DGA1-LEU2 | This Example |
| MTYL081 | MATa, leu2-270, ura3-302::URA3, xpr2-332, axp-2 TEFin-LacZ-LEU2 | This Example |
| MTYL085 | MATa, leu2-270, ura3-302::URA3, xpr2-332, axp-2 hp4d-ACC1-LEU2 | This Example |

TABLE 2

Primers used in this study.

| Primer | Description | SEQ ID NO | Sequence |
|---|---|---|---|
| PCR | | | |
| MT233 | XYL2 | 22 | AATGACTGCTAACCCTTCCTTGGTGT |
| MT234 | XYL2 | 23 | CTGGTCTAGGTGGTACCTTACTCAGGGCCGTCAATGAGAC |
| MT243 | XYL1 | 24 | AATGCCTTCTATTAAGTTGAACTCTGGTTAC |
| MT244 | XYL1 | 25 | CTAGGTCTTACTGGTACCTTAGACGAAGATAGGAATCTTGTCCCA |
| MT281 | XYL1 | 26 | TAACCGCAGCATCATCACCATCACCACCCTTCTATTAAGTTGAACTCTGGTTACGAC |
| MT282 | XYL1 | 27 | CTTACAGGTACCTTAGACGAAGATAGGAATCTTGTCCCAG |
| RT-PCR | | | |
| MTR001 | Actin | 28 | TCCAGGCCGTCCTCTCCC |
| MTR002 | Actin | 29 | GGCCAGCCATATCGAGTCGCA |
| MTR017 | ylXYL1 | 30 | AAGGAGTGGGCTGGATGGA |
| MTR018 | ylXYL1 | 31 | GGTCTCTCGGGTAGGGATCTTG |
| MTR019 | ylXYL2 | 32 | ATGGAGGAATCGGCGACTT |
| MTR020 | ylXYL2 | 33 | ACCACCTCTCCGGCACTTT |
| MTR031 | DGA | 34 | AACGGAGGAGTGGTCAAGCGA |
| MTR032 | DGA | 35 | TTATGGGGAAGTAGCGGCCAA |
| MTR051 | psXYL2 | 36 | CTCCAAGTTGGGTTCCGTTGC |
| MTR052 | psXYL2 | 37 | GCGACAGCAGCAGCCAAAAGA |
| MTR053 | psXYL1 | 38 | AGGCTATCGCTGCTAAGCACGG |
| MTR054 | psXYL1 | 39 | TTTGGAATGATGGCAATGCCTC |
| MTR055 | ylXYL3 | 40 | CAGCTCAAGGGCATCATTCTGG |
| MTR056 | ylXYL3 | 41 | TGCGGCAAGTCGTCCTCAAA |
| MTR060 | IDH1 | 42 | CTTCGAACCGCCTACCTGGCTA |
| MTR061 | IDH1 | 43 | TGGGCTGGAACATGGTTCGA |
| MTR064 | ACO1 | 44 | CACCGCTTTCGCCATTGCT |
| MTR065 | ACO1 | 45 | GGGCTCCTTGAGCTTGAACTCC |
| MTR066 | PDB1 | 46 | CTGTGGTGTCGTCAACGACTCC |
| MTR067 | PDB1 | 47 | GCTCAATGGCGTAAGGAGTGG |
| MTR072 | ICL | 48 | TACTCTCCCGAGGACATTGCC |
| MTR073 | ICL | 49 | CAGCTTGAAGAGCTTGTCAGCC |

Relevant restriction sites are in bold.

Direct Transesterification

For routine lipid quantification to determine relative lipid accumulation, a method for direct transesterification of cell biomass was used, adapted from the two-step base-then-acid-catalyzed direct transesterification method developed by Griffiths et al. (Griffiths et al. 2010). A normalized quantity of cell culture was centrifuged and the media supernatant was removed. Samples were then stored in −20° C. freezer or directly transesterified. The cell was then resuspended with the addition of 100 μL of hexane containing 10 mg/mL methyl tridecanoate internal standard. 500 μL 0.5 N sodium methoxide, prepared by the addition of sodium hydroxide to methanol, was then added to the sample. The sample was then vortexed for 1 hour at room temperature. Next 40 µL of sulfuric acid was carefully added to the sample, followed by the addition of 500 µL of neat hexane. The sample was again vortexed at room temperature for another 30 minutes. 300 µL of the upper hexane layer was then transferred into a glass vial and run using the GC-FID, under standard operating conditions. Total lipid content was calculated as the sum of total fatty acid content for the five primary FAMEs identified.

Results & Discussion

Elucidating Endogenous Functionality of the Xylose Utilization Pathway in *Y. lipolytica*

Within the literature, there are conflicting reports about the ability for *Y. lipolytica* to naturally consume xylose. In most reports, growth on xylose has not been observed (Pan et al. 2009; Ruiz-Herrera and Sentandreu 2002). However, there are reports of *Y. lipolytica* positively growing on xylose: strain Po1g was found to consume xylose in a cane hydrolysate fermentation (Tsigie et al. 2011), and two strains of *Y. lipolytica* were grown on xylose to measure xylulose-5-phosphate phosphoketolase activity (Evans and Ratledge 1984). Beyond these incidences, there is otherwise very little reported evidence of using *Y. lipolytica* for growth on xylose, despite the volume of research of using the organism grow on other alternative and residual substrate sources (Papanikolaou et al. 2002; Papanikolaou et al. 2003; Scioli and Vollaro 1997). Table 3 lists putative XR/XDH/XK genes within the genome of *Y. lipolytica* from a BLAST comparison to known functional pathway genes. While the amino acid identity is only 40-52%, the expect value indicates significant likelihood of similarity, and *Y. lipolytica* often manages only 40-60% amino acid identity with orthologous genes from *S. cerevisiae*, due to distal phylogeny. Nonetheless, the low homology calls into question the potential functional characteristics of these genes, which further adds to the controversy.

TABLE 3

BLAST results for endogenous xylose utilization pathway in *Y. lipolytica*. Amino acid identity is indicated in comparison with the parent sequence (organism indicated in parentheses). Expect value is the statistical false-positive rate.

| Function | Accession Number | Identity | Expect Value |
| --- | --- | --- | --- |
| Xylose reductase (XR) | YALI0D07634p | 49% (*S. stipitis*) | 3e-80 |
| Xylitol dehydrogenase (XDH) | YALI0E12463p | 52% (*S. stipitis*) | 1e-96 |
| Xylulokinase (XK) | YALI0F10923p | 40% (*S. cerevisiae*) | 1e-96 |

Figure 1B:
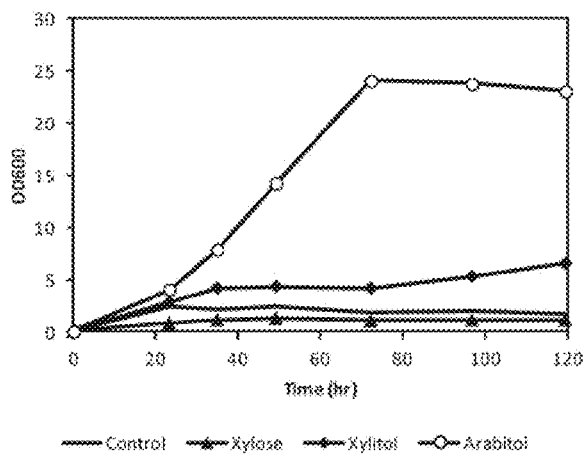

To test the ability for *Y. lipolytica* to utilize its endogenous putative XYL123 pathway in laboratory conditions, control strain MTYL038 was grown in minimal media on three different substrates: xylose, xylitol, arabitol. As seen in FIG. 1A, these three substrates can be used to diagnose the functionality of the three XYL123 genes. For example, growth on xylitol will demonstrate that XYL2 and XYL3 are functional, while growth on arabitol demonstrates that XYL3 is functional. FIG. 1B depicts the growth curves of MTYL038 on the various substrates, with a shake flask with no carbon substrate as the control. While it was found that the strain did not grow on xylose, it was found to grow weakly on xylitol and quite robustly on arabitol. This suggests that while XYL1, and most likely XYL2, are not naturally expressed or functional in *Y. lipolytica* in the presence of their respective substrates, XYL3 is expressed and the organism can grow utilizing this pathway as its primary catabolic pathway.

Expression of XYL12 Enables Growth on Xylose

With the knowledge that the endogenous xylulokinase is functional in *Y. lipolytica*, the remaining elements of the xylose utilization pathway were integrated to enable growth on xylose. The XYL1 and XYL2 genes from *S. stipitis* cloned into *Y. lipolytica* expression cassettes. XYL1 was cloned under the control of the stronger TEFin promoter, while the XYL2 gene was cloned under the control of hp4d. The XYL2 expression cassette was inserted into the XYL1 plasmid, creating plasmid pMT081, expressing both XYL1 and XYL2. Transformation of this plasmid into background strain Po1g yielded the strain MTYL081.

Figure 2A:
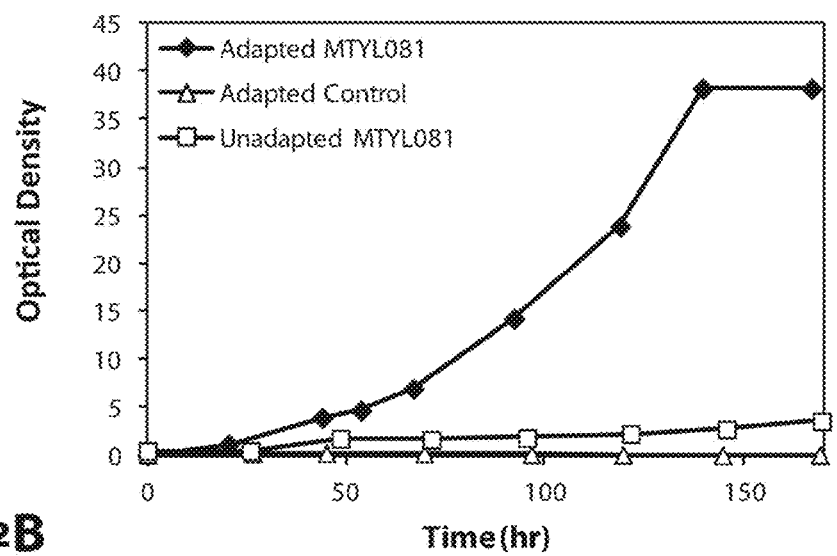
FIG. 2A: Growth of adapted *Y. lipolytica* strain MTYL081 on xylose as sole carbon source in minimal media shake flask, compared to unadapted MTYL081 and control strain MTYL038 that underwent the adaptation protocol.

Numerous experiments working with *S. cerevisiae* and the xylose utilization pathway have discovered that it is often necessary to include periods of adaptation—where serial dilution in xylose media is performed—for development of stable xylose utilization (Jeffries 2006; Kuyper et al. 2004; Tomás-Pejó et al. 2010). This was similarly found to be the case in *Y. lipolytica*—the verified transformant MTYL081 initially did not grow on xylose. It was grown in minimal xylose media in a shake flask for 10 days before reinoculating in fresh media. This serial dilution was repeated until there was an observed increase in maximum OD to above 15. FIG. 2A shows the growth curve on the third serial dilution compared to the original unadapted strain and a control strain that underwent serial dilution in xylose media. Lack of growth from the latter two strains shows that adaptation is necessary for xylose utilization and adaptation does not occur in strains lacking the heterologous XYL12 genes. Adapted growth was found to be steady and roughly exponential, with the maximum OD of 38 being reached after 130 hours. The doubling time is roughly 25 hrs, which is significantly lower than rates typically observed on glucose but comparable to that on arabitol (see FIG. 1B).

Figure 2B:
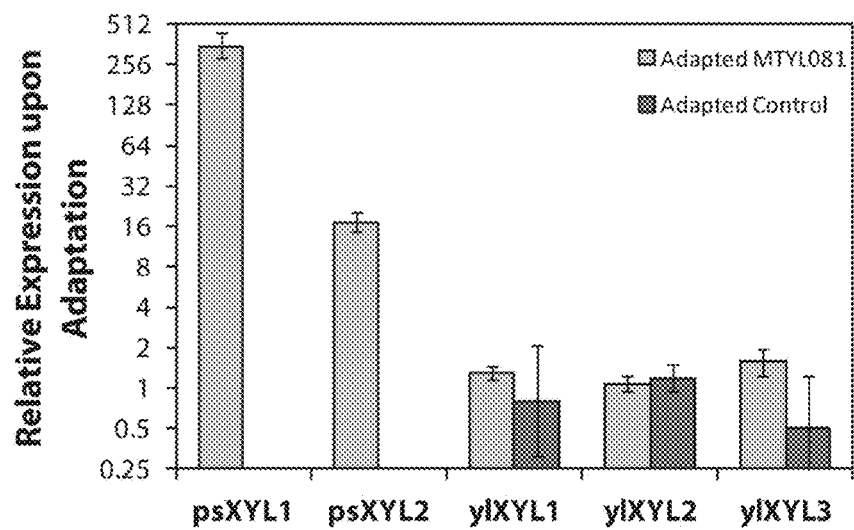
FIG. 2B: Transcriptional comparison of the xylose utilization pathway of an adapted *Y. lipolytica* strain and an unadapted strain. psXYL1 and psXYL2 are heterologously expressed from *S. stipitis*, while ylXYL1, ylXYL2, ylXYL3 are the endogenous putative xylose utilization pathway.

To explore the underlying adaptations that improved the xylose-utilizing phenotype, RT-PCR was performed comparing the expression of heterologously expressed XYL12 and endogenous XYL123 genes in the adapted and unadapted strains. FIG. 2B shows the relative change in transcription level of the genes after adaptation. The heterologously expressed XYL1 was overexpressed 300-fold compared to the unadapted strain, while XYL2 was upregulated 17-fold. Within the adapted strain, XYL1 was expressed 6-fold greater than XYL2, which is in agreement with the expression expected from the promoters used. Endogenous XYL123 was not significantly upregulated both in adapted MTYL081 and the control strain that underwent serial dilution, indicating that the observed adaptation to xylose was not an activation of the putative native xylose pathway. The strong upregulation of XYL1 and XYL2 has been similarly observed in metabolic engineering of *S. cerevisiae*, as the utilization pathway, being both heterologously expressed and potentially the rate-limiting step, requires strong overexpression for sufficient growth (Karhumaa et al. 2005; Karhumaa et al. 2007). This seems to likewise be the case in *Y. lipolytica*, as the two XYL12 steps achieve very strong overexpression and yet still only achieve a relatively low growth rate. However, it may also be that with the adapted XYL12 expression, new rate-limiting steps appear to hinder specific growth on xylose, such as PPP activity or pentose transport (Karhumaa et al. 2005).

The normal combined activity of XYL1 and XYL2 consumes one NADPH and generates one NADH. Without suitable means to regenerate NADPH from NADH, this can lead to cofactor imbalances and has been seen as a significant challenge in metabolic engineering of *S. cerevisiae* (Matsushika et al. 2009). However, with a potential cofactor imbalance, one would expect early cessation of growth and large accumulation of xylitol due to complete depletion on NADPH. In our shake flask cultures we observed only <0.5 g/L xylitol formation after consumption of 32 g/L of xylose, while the maximum OD was very higher compared to what is typically observed in shake flasks, suggesting that cofactor balance may not be an issue in this situation. While this does not remove the possibility of rate-limiting steps in the exchange of NADPH to NADH, thus slowing but not stopping growth, in the presence of oxygen, mitochondrial function actively controls and maintains the NADPH/NADH equilibrium and exchange fluxes (Singh and Mishra 1995).

Cofermentation of Two Substrates for Improved Productivity

While metabolic engineering allowed growth on xylose in *Y. lipolytica*, growth was dramatically slower than on glucose. Possible factors contributing to the limited growth and productivity are the lack of dedicated pentose transporters, low PPP flux, and inability for the cell to identify xylose as a fermentable sugar (Jeffries 2006; Jin et al. 2004; Matsushika et al. 2009). To improve productivities with the limited specific growth on xylose, experiments were performed using two-substrate cofermentations. Cellulosic materials typically consist of a blend of both hexose and pentose sugars, and rarely consist of pure pentose (Lee et al. 2007). Furthermore, substrates like glycerol are a byproduct of biodiesel production, and may be recycled back into the process. First it was necessary to characterize and determine which cofermentation combinations are ideal for lipid production. Xylose was combined with a helper substrate—glucose, glycerol, or arabitol—and grown in shake flasks to determine growth characteristics and observe catabolite repression effects in the cofermentation system. Catabolite repression is the preferential uptake of one substrate through the repression of the utilization pathway of secondary substrates, and can be seen in a wide range of cofermentations in *Y. lipolytica* (Morgunov and Kamzolova 2011). The strain MTYL085 was used, which contains the XYL12 pathway as well as DGA overexpression. DGA overexpression is capable of improving lipid accumulation and was found to be a strong contributor to engineered lipid overproduction (Kamisaka et al. 2007). By combining both the xylose utilization pathway and elements for lipid overproduction, we may be able to direct flux from xylose towards lipids for a cellulosic biodiesel platform.

Figure 3A:
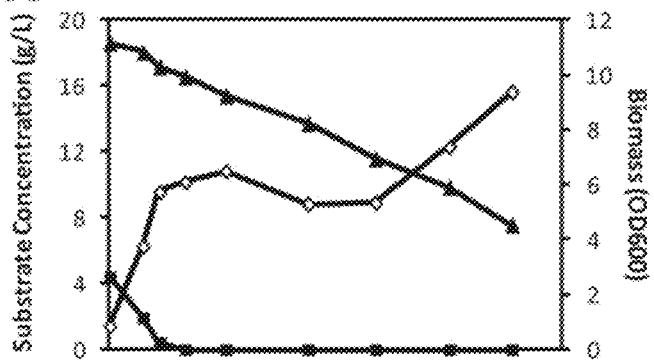
FIGS. 3A-3C. Cofermentation of xylose with glucose (FIG. 3A), glycerol (FIG. 3B), or D-arabitol (FIG. 3C). Cultures were grown on 20 g/L xylose and 4 g/L of the secondary substrate.
Figure 3B:
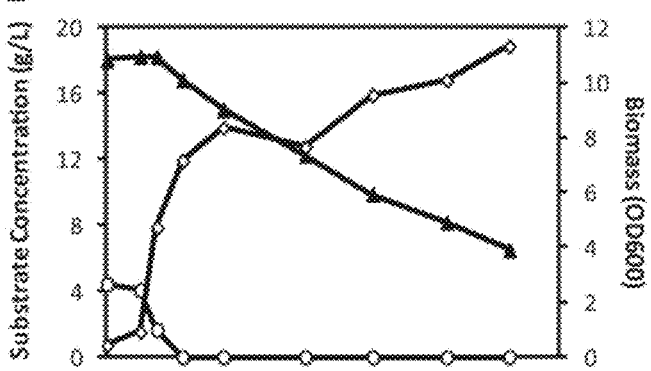
Figure 3C:
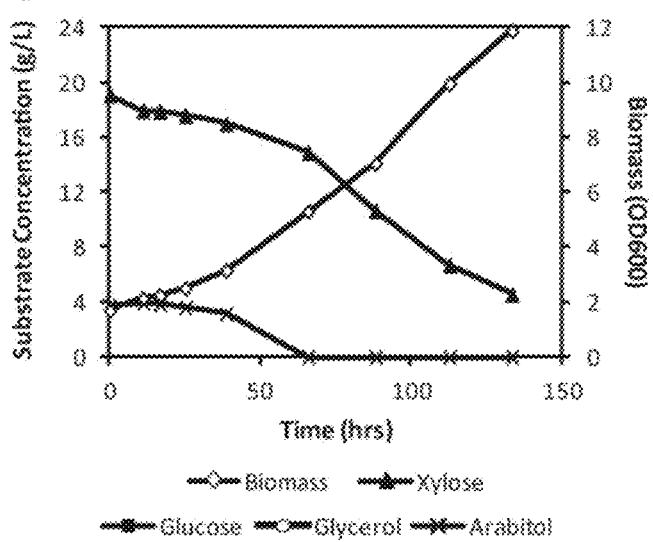

FIGS. 3A-3C depict the growth characteristics and depletion of both substrates for the three cofermentation combinations. For glycerol (FIG. 3B), diauxic shift is clearly observed, with glycerol being consumed rapidly before any xylose is depleted. For glucose (FIG. 3A), diauxic shift was less observable, as it is possible that at very low concentrations of glucose, catabolite repression is weak (Morgunov and Kamzolova 2011). At higher glucose concentrations, diauxic shift was clearly observable (data not shown). While all three cultures began with 4 g/L of the helper substrate, glycerol was converted into the most biomass after it was completely depleted, achieving an OD of 8 within 24 hrs. Glycerol has been known to be a highly preferred substrate for *Y. lipolytica*, and unlike *S. cerevisiae*, there is no loss in specific growth rate when growing on glycerol compared to glucose (Taccari et al. 2012). It is also Crabtree-negative, an effect that eschews the respiration-dependent nature of glycerol metabolism found in *S. cerevisiae* (De Deken 1966). As a result, MTYL085 is able to consume slightly more xylose by the end of the culture. The evidence of diauxic shift also indicates that while the xylose uptake rate may be constant when grown solely on xylose, other factors must be at play in repressing the utilization, most conspicuously pentose transport. There is a growing body of evidence that pentose transport is a key rate-limiting step in xylose utilization and may also be a strong contributing factor towards diauxic shift (Young et al. 2012).

The cofermentation of xylose and arabitol exhibits a much different response (FIG. 3C). Since arabitol shares the same catabolic route for all but the initial pathway, it is likely the arabitol response will be most similar to the xylose growth phenotype. Furthermore, xylose depletion begins well before arabitol is consumed, exhibiting simultaneous utilization of both substrates. The smooth growth profile in this case is in contrast to the two-phase growth seen in glucose or glycerol—a product of diauxic growth. Nonetheless the overall growth rate and productivity is significantly lower than glucose or glycerol. Additionally, arabitol is not a common substrate in cellulosic material and would thus be a prohibitive cost to supplement as a feedstock.

Lipid Production in Xylose and Glycerol Cofermentation

Figure 4:
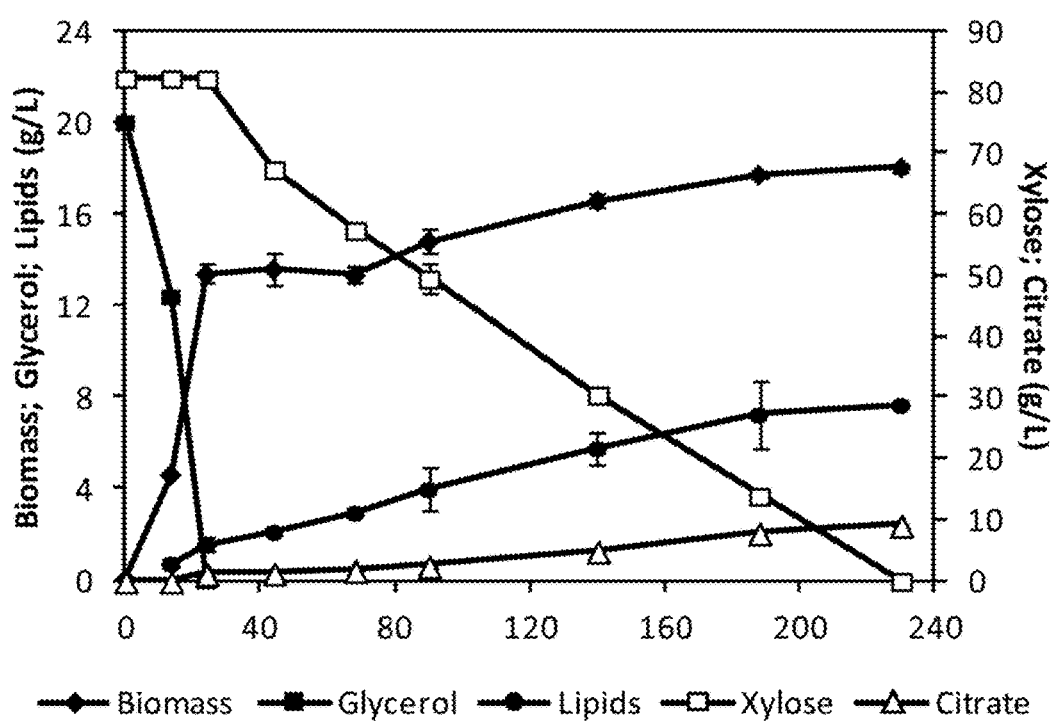
FIG. 4. 2-L bioreactor fermentation of strain MTYL081 on glycerol and xylose. C/N ratio was adjusted to 100, with 20 g/L of glycerol and 80 g/L of xylose. Samples were taken in triplicate.

Because glycerol showed the greatest promise for increased productivity, a scale-up cofermentation was performed using glycerol and xylose as substrates. A 2-L bioreactor was initially charged with 20 g/L glycerol and 80 g/L xylose. The C/N ratio of the reactor was adjusted to be 100, which results nitrogen-limited conditions favorable for lipid accumulation. The results of the fermentation are found in FIG. 4. Over the course of 230 hrs, all the carbon substrate was consumed, with glycerol being depleted within the first 24 hrs. Diauxic shift can clearly be observed, as no xylose is consumed until after all the glycerol has been depleted. The 20 g/L of glycerol was able to generate 13 g/L of biomass. Lipid accumulation steadily occurred between 70 and 230 hours, with a majority of the biomass generated on xylose being accounted as lipids. The culture finally achieved a biomass concentration of 18 g/L with 7.64 g/L lipids, or 42% of total biomass. The overall productivity was 0.033 g lipids/L/hr. Strain MTYL085 was able to convert xylose into lipids at quantities similar to other *Y. lipolytica* fermentations (Beopoulos et al. 2009; Papanikolaou and Aggelis 2002). The yield of lipid production, however, was very low. Of the 80 g/L of xylose consumed, only 6.08 g/L of lipids was generated, for a yield of 0.074 g lipids/g xylose. This is only 21.7% of the theoretical yield. This low yield may be due to overrespiration of the carbon substrate, as high aeration on a foreign substrate may lead to strong flux through the TCA cycle. Furthermore, 9.13 g/L citrate was also generated, which actually accounts for a significant yield from the 100 g/L of carbon substrate initially charged. It is possible that the C/N ratio was too high, as extreme C/N ratios in *Y. lipolytica* fermentations can tend to produce citrate instead of lipids, likely due to limited ability to generate sufficient ATP for fatty acid synthesis (Beopoulos et al. 2009). Despite these low yields, the vast majority (80%) of the lipids were produced after glycerol depletion and during the xylose-only phase, indicating successful conversion of xylose-to-lipids using *Y. lipolytica*, a first step in developing a cellulosic biodiesel platform.

Transcriptional Expression Affected by Secondary Substrate

Figure 5:
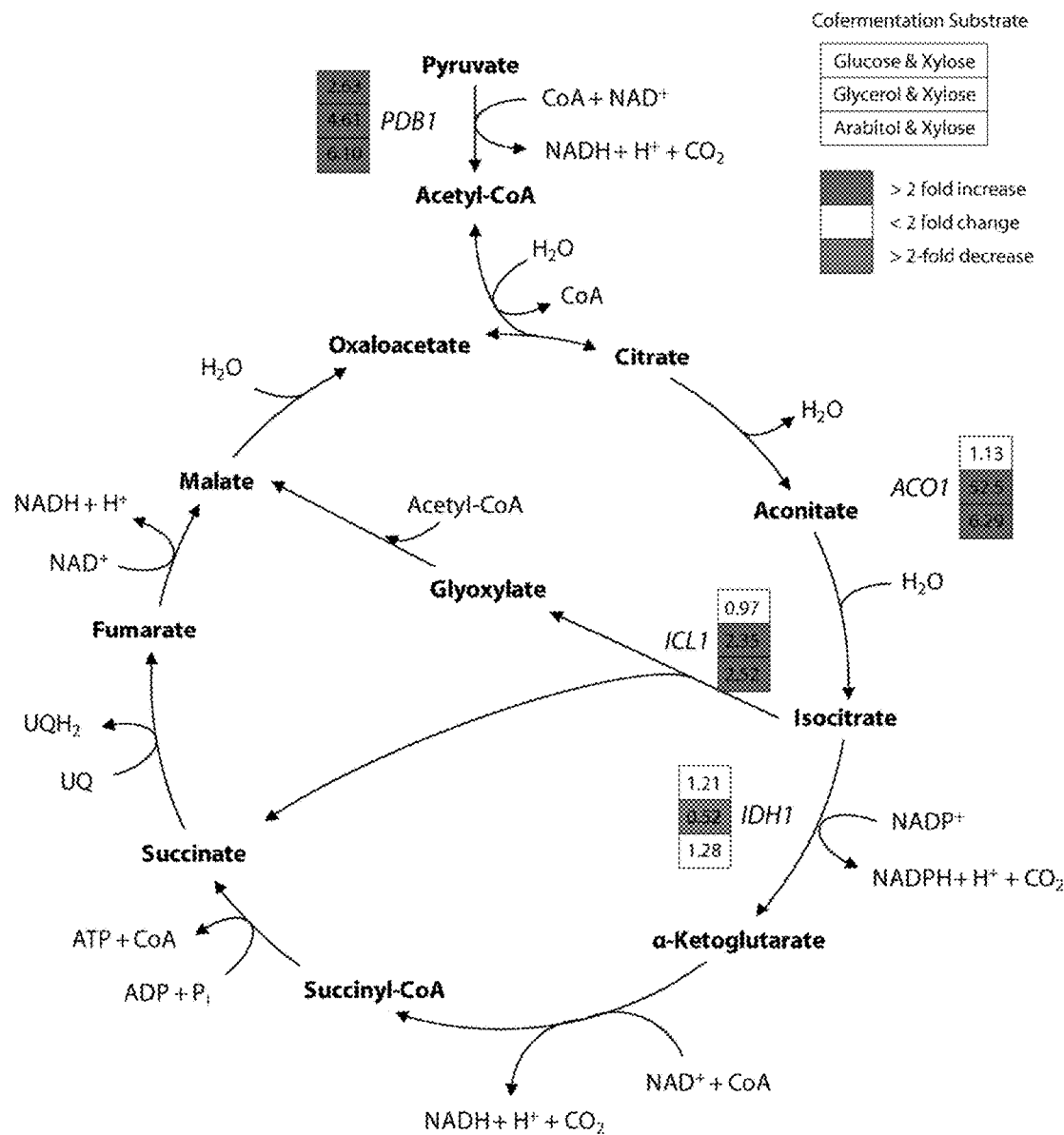
FIG. 5. Comparison of mRNA levels of genes responsible for energy production during xylose cofermentation with a secondary substrate: glucose, glycerol, arabitol. The comparison is between two time points during the cofermentation: when primarily the secondary substrate is being consumed vs. when the secondary substrate is depleted and only xylose is being consumed. Transcript levels that did not change significantly are shown in white boxes. Transcript levels that increased more than two-fold after transitioning to xylose utilization are shown in dark gray boxes. Transcript levels that decreased more than two-fold after transitioning to xylose are shown in light gray boxes. Numbers inside of each box indicate the ratio of transcripts during the xylose-only phase vs. secondary substrate phase. Numbers greater than 1.0 signify up-regulation of the gene when transitioning from secondary substrate to xylose, while numbers less than 1.0 signify downregulation.

To further investigate the response of *Y. lipolytica* during cofermentations with xylose and the overrespiration observed on glycerol-xylose, transcriptional analysis was performed on genes within the TCA cycle. Xylose consumption in *S. cerevisiae* elicits a non-fermentative response and general upregulation of the TCA cycle (Jin et al. 2004; Salusjarvi et al. 2006). This results in lower efficiencies in xylose utilization for ethanol production as downregulation of the TCA cycle is necessary to divert carbon flux towards ethanol fermentation, whether via anaerobic environmental conditions or activity of the Crabtree effect. In our cofermentation system, the response of *Y. lipolytica* when transitioning from the helper substrate to xylose was examined. An initial RNA extraction was performed during the cofermentation while still growing on glucose, glycerol or arabitol, and a second RNA extraction was performed after the helper substrate was depleted and the strain was exhibiting growth on xylose as sole carbon substrate. RT-PCR primers used in this study are listed in Table 2. From this we can identify if a similar respiratory response is observed on xylose. FIG. 5 depicts the fold-change in transcripts for pyruvate dehydrogenase (PDB1, Accession Number: XM_504448), Aconitase (ACO1, Accession Number: XM_502616), isocitrate lyase (ICL1, Accession Number: XM_501923), and isocitrate dehydrogenase (IDH1, Accession Number: XM_503571). These genes represent key enzymatic steps for the utilization of TCA cycle intermediates: PDB1, entrance into the TCA cycle; ACO1, diverting citrate to the TCA cycle instead of the cytosol; ICL1, diverting isocitrate through the glyoxylate shunt; IDH1, committed step into oxidative respiration.

In all three cases, PDB1 is significantly upregulated, suggesting that there is a stronger driving force towards the TCA cycle in xylose than any other substrate. Aconitase overexpression was not observed in the glucose-to-xylose transition, but was dramatically increased 50-fold in the glycerol-to-xylose transition. This was mostly due to very low transcription levels observed of ACO1 on glycerol rather than extraordinarily high expression of ACO1 on xylose. ACO1 was upregulated in the transition from arabitol to xylose as well. For ICL1, significant increase in expression was observed during the glycerol-to-xylose transition and the arabitol-to-xylose transition, but not on glucose. In most organisms, ICL1 is normally not expressed due to strong catabolite repression; however, *Y. lipolytica* seems to exhibit constitutive expression of the pathway (Flores and Gancedo 2005). Indeed, the magnitude of changes in expression of ICL1 suggests significant expression prior to the transition. Finally, IDH1 expression is not significantly changed in glucose and arabitol, but is actually downregulated on glycerol, indicating that respiration is much more strongly upregulated on glycerol than xylose.

The upregulation of PDB1 and ACO1 in the glycerol fermentation demonstrate an elevated respiratory response when transitioning from glycerol to xylose utilization. While IDH1 is downregulated, the upstream regulation may be enough to result in the overrespiration observed in the bioreactor. It is unclear why ACO1 is downregulated so dramatically when growing on glycerol, but any previous regulation on this enzyme must surely be alleviated. On the other hand, glucose-xylose cofermentation resulted in few significant changes in transcription. This may indicate that glucose-xylose cofermentation may yield better results at larger scales despite the stronger preference for glycerol by *Y. lipolytica*.

CONCLUSION

Pentose utilization represents a pressing need in the development of sustainable biofuel production, as the push and advantages for cellulosic feedstocks begin to outweigh the technical challenges. The oleaginous yeast *Y. lipolytica* is an example of a robust platform for the production of yeast oil that can be converted into biodiesel. Through metabolic engineering, the robust lipid production capabilities established in *Y. lipolytica* can be expanded to include xylose utilization, enabling further opportunities for microbial cellulosic biodiesel production. By testing native growth on a variety of substrates we showed that the endogenous XYL3 is functional in minimal media, while the putative XYL12 genes are not. Through heterologous expression of XYL1 and XYL2 genes from *S. stipitis* we enabled xylose utilization in *Y. lipolytica* after an adaptation period. Through cofermentation we are able to eliminate lag phases and increase growth and productivity on xylose, ultimately achieving 42% lipid accumulation in a strain that is metabolically engineered in both xylose utilization and lipid accumulation pathways. By observing that the TCA cycle response, we also observed variation between cofermentation substrates, suggesting a transcriptional regulatory basis for overrespiration. By leveraging the knowledge base developed from the study of xylose utilization in *S. cerevisiae*, these results establish a framework for studying and engineering the oleaginous yeast *Y. lipolytica* for xylose utilization and the production of cellulosic biodiesel.

REFERENCES

Barth G, Gaillardin C. 1997. Physiology and genetics of the dimorphic fungus *Yarrowia lipolytica*. FEMS Microbiol. Rev. 19(4):219-237.

Beopoulos A, Cescut J, Haddouche R, Uribelarrea J L, Molina-Jouve C, Nicaud J M. 2009. *Yarrowia lipolytica* as a model for bio-oil production. Progress in Lipid Research 48(6):375-387.

Blank L M, Lehmbeck F, Sauer U. 2005. Metabolic-flux and network analysis in fourteen hemiascomycetous yeasts. FEMS Yeast Res. 5(6-7):545-558.

De Deken R. 1966. The Crabtree effect and its relation to the petite mutation. Journal of general microbiology 44(2): 157.

Evans C T, Ratledge C. 1984. Induction of xylulose-5-phosphate phosphoketolase in a variety of yeasts grown on d-xylose: the key to efficient xylose metabolism. Arch. Microbiol. 139(1):48-52.

Flores C-L, Gancedo C. 2005. *Yarrowia lipolytica* Mutants Devoid of Pyruvate Carboxylase Activity Show an Unusual Growth Phenotype. Eukaryotic Cell 4(2):356-364.

Griffiths M J, van Hille R P, Harrison S T L. 2010. Selection of direct transesterification as the preferred method for assay of fatty acid content of microalgae. Lipids 45(11): 1053-1060.

Jeffries T W. 2006. Engineering yeasts for xylose metabolism. Curr. Opin. Biotechnol. 17(3):320-326.

Jin Y-S, Laplaza J M, Jeffries T W. 2004. *Saccharomyces cerevisiae* Engineered for Xylose Metabolism Exhibits a Respiratory Response. Appl. Environ. Microbiol. 70(11): 6816-6825.

Kamisaka Y, Tomita N, Kimura K, Kainou K, Uemura H. 2007. DGA1 (diacylglycerol acyltransferase gene) overexpression and leucine biosynthesis significantly increase lipid accumulation in the Δsnf2 disruptant of *Saccharomyces cerevisiae*. Biochemal Journal 408(1):61-68.

Karhumaa K, Hahn-Hagerdal B, Gorwa-Grauslund M F. 2005. Investigation of limiting metabolic steps in the utilization of xylose by recombinant *Saccharomyces cerevisiae* using metabolic engineering. Yeast 22(5):359-368.

Karhumaa K, Sanchez R, Hahn-Hagerdal B, Gorwa-Grauslund M-F. 2007. Comparison of the xylose reductase-xylitol dehydrogenase and the xylose isomerase pathways for xylose fermentation by recombinant *Saccharomyces cerevisiae*. Microbial Cell Factories 6(1):5.

Kuyper M, Winkler A A, van Dijken J P, Pronk J T. 2004. Minimal metabolic engineering of *Saccharomyces cerevisiae* for efficient anaerobic xylose fermentation: a proof of principle. FEMS Yeast Res. 4(6):655-664.

Lee D, Owens V N, Boe A, Jeranyama P. 2007. Composition of herbaceous biomass feedstocks: South Dakota State University.

Matsushika A, Inoue H, Kodaki T, Sawayama S. 2009. Ethanol production from xylose in engineered *Saccharomyces cerevisiae* strains: current state and perspectives. Appl. Microbiol. Biotechnol. 84(1):37-53.

Morgunov I G, Kamzolova S V. 2011. *Yarrowia Lipolytica* Yeast Possesses An Atypical Catabolite Repression. Albany 2011: Conversation 17.

Pan L X, Yang D F, Li S, Wei L, Chen G GLiang Z Q. 2009. Isolation of the Oleaginous Yeasts from the Soil and Studies of Their Lipid-Producing Capacities. Food Technology and Biotechnology 47(2):215-220.

Papanikolaou S, Aggelis G. 2002. Lipid production by *Yarrowia lipolytica* growing on industrial glycerol in a single-stage continuous culture. Bioresour. Technol. 82(1):43-49.

Papanikolaou S, Chevalot I, Komaitis M, Marc I, Aggelis G. 2002. Single cell oil production by *Yarrowia lipolytica* growing on an industrial derivative of animal fat in batch cultures. Appl. Microbiol. Biotechnol. 58(3):308-312.

Papanikolaou S, Muniglia L, Chevalot I, Aggelis G, Marc I. 2003. Accumulation of a cocoa-butter-like lipid by *Yarrowia lipolytica* cultivated on agro-industrial residues. Curr. Microbiol. 46(2):124-130.

Perlack R D. 2005. Biomass as Feedstock for a Bioenergy and Bioproducts Industry: The Technical Feasability of a Billion-Ton Annual Supply. Oak Ridge National Lab.

Ratledge C. Single Cell Oil; 1988. Longman Scientific & Technical. p 33-70.

Ruiz-Herrera Je, Sentandreu R. 2002. Different effectors of dimorphism in *Yarrowia lipolytica*. Arch Microbiol 178 (6):477-483.

Salusjarvi L, Pitkanen J P, Aristidou A, Ruohonen L, Penttila M. 2006. Transcription analysis of recombinant *Saccharomyces cerevisiae* reveals novel responses to xylose. Appl. Biochem. Biotechnol. 128(3):237-261.

Sambrook J, Russell D W. 2001. Molecular cloning: a laboratory manual: CSHL press.

Scioli C, Vollaro L. 1997. The use of *Yarrowia lipolytica* to reduce pollution in olive mill wastewaters. Water Res. 31(10):2520-2524.

Singh A, Mishra P. 1995. Microbial Pentose Utilization: Current Applications in Biotechnology: Elsevier Science.

Taccari M, Canonico L, Comitini F, Mannazzu I, Ciani M. 2012. Screening of yeasts for growth on crude glycerol and optimization of biomass production. Bioresource Technology 1:1.

Tomás-Pejó E, Ballesteros M, Oliva J, Olsson L. 2010. Adaptation of the xylose fermenting yeast *Saccharomyces cerevisiae* F12 for improving ethanol production in different fed-batch SSF processes. Journal of Industrial Microbiology & Biotechnology 37(11):1211-1220.

Tsigie Y A, Wang C-Y, Truong C-T, Ju Y-H. 2011. Lipid production from *Yarrowia lipolytica* Po1g grown in sugarcane bagasse hydrolysate. Bioresour. Technol. 102(19): 9216-9222.

Walfridsson M, Hallborn J, Penttila M, Keränen S, Hahn-Hagerdal B. 1995. Xylose-metabolizing *Saccharomyces cerevisiae* strains overexpressing the TKL1 and TAL1 genes encoding the pentose phosphate pathway enzymes transketolase and transaldolase. Applied and environmental microbiology 61(12):4184-4190.

Young E M, Comer A D, Huang H, Alper H S. 2012. A molecular transporter engineering approach to improving xylose catabolism in *Saccharomyces cerevisiae*. Metab. Eng. 1:1.

Zhao S, Fernald R D. 2005. Comprehensive Algorithm for Quantitative Real-Time Polymerase Chain Reaction. Journal of Computational Biology 12(8):1047-1064.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The invention claimed is:

1. An isolated oleaginous cell comprising a nucleic acid construct that increases expression of:
   a xylose isomerase (XYLA) gene product, a xylose reductase (XYL1) gene product and a xylitol dehydrogenase (XYL2) gene product,
   wherein the nucleic acid construct comprises an intron; and
   a) an expression cassette comprising a nucleic acid sequence encoding the XYLA, XYL1, and XYL2 gene products under the control of a suitable homologous or heterologous promoter; and/or
   b) a nucleic acid sequence that modulates the level of expression of the XYLA, XYL1, and XYL2 gene products when inserted into the genome of the cell.

2. The isolated oleaginous cell of claim 1, further comprising a nucleic acid construct that increases expression of a xylulokinase (XYL3) gene product.

3. The isolated oleaginous cell of claim 1, further comprising a nucleic acid construct that increases expression of a diacylglycerol acyltransferase (DGA) gene product, an acetyl-coA carboxylase (ACC) gene product, a stearoyl-CoA-desaturase (SCD) gene product, and/or an ATP-citrate lyase (ACL) gene product.

4. The isolated oleaginous cell of claim 1, wherein the nucleic acid construct inhibits or disrupts the natural regulation of a native gene encoding the gene product resulting in overexpression of the native gene.

5. The isolated oleaginous cell of claim 1, wherein the increased expression of the gene product confers a beneficial phenotype for the conversion of a carbon source to a fatty acid, fatty acid derivative and/or triacylglycerol (TAG) to the cell.

6. The isolated oleaginous cell of claim 5, wherein the beneficial phenotype is a modified fatty acid profile, a modified TAG profile, an increased fatty acid and/or triacylglycerol synthesis rate, an increase conversion yield, an increased triacylglycerol accumulation in the cell, and/or an increased triacylglycerol accumulation in a lipid body of the cell.

7. The isolated oleaginous cell of claim 6, wherein the synthesis rate, yield or accumulation of a fatty acid or a TAG of the cell is at least 2-fold increased as compared to unmodified cells of the same cell type.

8. The isolated oleaginous cell of claim 5, wherein the cell converts a carbon source to a fatty acid or a TAG at a conversion rate within the range of about 0.025 g/g to about 0.32 g/g (g TAG produced/g Glucose consumed).

9. The isolated oleaginous cell of claim 1, wherein the cell is an oleaginous yeast cell.

10. The isolated oleaginous cell of claim 1, wherein the cell is a *Y. lipolytica* cell.

11. A culture, comprising the isolated oleaginous cell of claim 1.

12. The culture of claim 11, further comprising a carbon source.

13. The culture of claim 12, wherein the carbon source comprises a fermentable sugar.

14. A method, comprising
   contacting a carbon source with an isolated oleaginous cell of claim 1, and
   incubating the carbon source contacted with the cell under conditions suitable for at least partial conversion of the carbon source into a fatty acid or a triacylglycerol by the cell.

15. The method of claim 14, wherein the carbon source is a fermentable sugar.

16. The method of claim 15, wherein the fermentable sugar is a C5 and/or a C6 sugar.

17. A method for increasing productivity of production of fatty acid or triacylglycerol by an isolated oleaginous cell, comprising
   culturing an isolated oleaginous cell of claim 1 with at least two types of carbon sources,
   wherein the first type of carbon source contains or is xylose, and
   wherein the second type of carbon source is a carbon source other than xylose,
   whereby the productivity of production of fatty acid or triacylglycerol by an isolated oleaginous cell is improved relative to culturing the isolated oleaginous cell or the culture without the second type of carbon source.

18. The method of claim 17, wherein the second type of carbon source contains or is a C2 carbon source, a C3 carbon source, a C5 carbon source other than xylose or a C6 carbon source.

* * * * *

SEQUENCE LISTING

```
<160> NUMBER OF SEQ ID NOS: 49

<210> SEQ ID NO 1
<211> LENGTH: 1026
<212> TYPE: DNA
<213> ORGANISM: Scheffersomyces stipitis

<400> SEQUENCE: 1
tacaactata ctacaatgcc ttctattaag ttgaactctg gttacgacat gccagccgtc      60
ggtttcggct gttggaaagt cgacgtcgac acctgttctg aacagatcta ccgtgctatc     120
aagaccggtt acagattgtt cgacggtgcc gaagattacg ccaacgaaaa gttagttggt     180
gccggtgtca agaaggccat tgacgaaggt atcgtcaagc gtgaagactt gttccttacc     240
tccaagttgt ggaacaacta ccaccaccca gacaacgtcg aaaaggcctt gaacagaacc     300
ctttctgact tgcaagttga ctacgttgac ttgttcttga tccacttccc agtcaccttc     360
aagttcgttc cattagaaga aaagtaccca ccaggattct actgtggtaa gggtgacaac     420
ttcgactacg aagatgttcc aattttagag acctggaagg ctcttgaaaa gttggtcaag     480
gccggtaaga tcagatctat cggtgtttct aacttcccag gtgctttgct cttggacttg     540
ttgagaggtg ctaccatcaa gccatctgtc ttgcaagttg aacaccaccc atacttgcaa     600
caaccaagat tgatcgaatt cgctcaatcc cgtggtattg ctgtcaccgc ttactcttcg     660
ttcggtcctc aatctttcgt tgaattgaac caaggtagag ctttgaacac ttctccattg     720
ttcgagaacg aaactatcaa ggctatcgct gctaagcacg gtaagtctcc agctcaagtc     780
ttgttgagat ggtcttccca aagaggcatt gccatcattc caaagtccaa cactgtccca     840
agattgttgg aaaacaagga cgtcaacagc ttcgacttgg acgaacaaga tttcgctgac     900
attgccaagt tggacatcaa cttgagattc aacgacccat gggactggga caagattcct     960
atcttcgtct aagaaggttg ctttatagag aggaaataaa acctaatata cattgattgt    1020
acattt                                                               1026

<210> SEQ ID NO 2
<211> LENGTH: 318
<212> TYPE: PRT
<213> ORGANISM: Scheffersomyces stipitis

<400> SEQUENCE: 2

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30
```

Arg Ala Ile Lys Thr Gly Tyr Arg Leu Phe Asp Gly Ala Glu Asp Tyr
            35                  40                  45

Ala Asn Glu Lys Leu Val Gly Ala Gly Val Lys Lys Ala Ile Asp Glu
 50                  55                  60

Gly Ile Val Lys Arg Glu Asp Leu Phe Leu Thr Ser Lys Leu Trp Asn
 65                  70                  75                  80

Asn Tyr His His Pro Asp Asn Val Glu Lys Ala Leu Asn Arg Thr Leu
                 85                  90                  95

Ser Asp Leu Gln Val Asp Tyr Val Asp Leu Phe Leu Ile His Phe Pro
                100                 105                 110

Val Thr Phe Lys Phe Val Pro Leu Glu Glu Lys Tyr Pro Pro Gly Phe
            115                 120                 125

Tyr Cys Gly Lys Gly Asp Asn Phe Asp Tyr Glu Asp Val Pro Ile Leu
130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
            195                 200                 205

Ala Val Thr Ala Tyr Ser Ser Phe Gly Pro Gln Ser Phe Val Glu Leu
            210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
            275                 280                 285

Asp Glu Gln Asp Phe Ala Asp Ile Ala Lys Leu Asp Ile Asn Leu Arg
290                 295                 300

Phe Asn Asp Pro Trp Asp Trp Asp Lys Ile Pro Ile Phe Val
305                 310                 315

<210> SEQ ID NO 3
<211> LENGTH: 1235
<212> TYPE: DNA
<213> ORGANISM: Scheffersomyces stipitis

<400> SEQUENCE: 3 cctcactta gtttgtttca atcacccta atactcttca cacaattaaa atgactgcta         60
acccttcctt ggtgttgaac aagatcgacg acatttcgtt cgaaacttac gatgccccag        120
aaatctctga acctaccgat gtcctcgtcc aggtcaagaa aaccggtatc tgtggttccg        180
acatccactt ctacgcccat ggtagaatcg gtaacttcgt tttgaccaag ccaatggtct        240
tgggtcacga atccgccggt actgttgtcc aggttggtaa gggtgtcacc tctcttaagg        300
ttggtgacaa cgtcgctatc gaaccaggta ttccatccag attctccgac gaatacaaga        360
gcggtcacta caacttgtgt cctcacatgg ccttcgccgc tactcctaac tccaaggaag        420
gcgaaccaaa cccaccaggt accttatgta agtacttcaa gtcgccagaa gacttcttgg        480
tcaagttgcc agaccacgtc agcttggaac tcggtgctct tgttgagcca ttgtctgttg        540

-continued

```
gtgtccacgc tctaagttg ggttccgttg ctttcggcga ctacgttgcc gtctttggtg    600
ctggtcctgt tggtcttttg gctgctgctg tcgccaagac cttcggtgct aagggtgtca    660
tcgtcgttga cattttcgac aacaagttga agatggccaa ggacattggt gctgctactc    720
acaccttcaa ctccaagacc ggtggttctg aagaattgat caaggctttc ggtggtaacg    780
tgccaaacgt cgttttggaa tgtactggtg ctgaaccttg tatcaagttg ggtgttgacg    840
ccattgcccc aggtggtcgt ttcgttcaag tcggtaacgc tgctggtcca gtcagcttcc    900
caatcaccgt tttcgccatg aaggaattga ctttgttcgg ttctttcaga tacggattca    960
acgactacaa gactgctgtt ggaatctttg acactaacta ccaaaacggt agagaaaatg    1020
ctccaattga ctttgaacaa ttgatcaccc acagatacaa gttcaaggac gctattgaag    1080
cctacgactt ggtcagagcc ggtaagggtg ctgtcaagtg tctcattgac ggccctgagt    1140
aagtcaaccg cttggctggc ccaaagtgaa ccagaaacga aaatgattat caaatagctt    1200
tatagacctt tatccaaatt tatgtaaact aatag                              1235
```

<210> SEQ ID NO 4
<211> LENGTH: 363
<212> TYPE: PRT
<213> ORGANISM: Scheffersomyces stipitis

<400> SEQUENCE: 4

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
```

```
                245                 250                 255
Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 5
<211> LENGTH: 1623
<212> TYPE: DNA
<213> ORGANISM: Yarrowia lipolytica

<400> SEQUENCE: 5

```
atgtatctcg gactggatct ttcgactcaa cagctcaagg gcatcattct ggacacaaaa    60
acgctggaca cggtcacaca gtccatgtg actttgagg acgacttgcc gcagttcaac    120
accgaaaagg gcgtctttca cagctctaca gtggccggag aaatcaatgc tcctgtggca    180
atgtgggggg cagctgtgga cttgctgata gagcgtctgt caaaggaaat agaccttttcc  240
acgatcaagt ttgtgtcggg ctcgtgccag caacacggct ctgtttatct caacagcagc    300
tacaaggagg gcctgggttc tctggacaaa cacaaagact tgtctacagg agtgtcatcc    360
ttactggcgc tcgaagtcag ccccaattgg caggatgcaa gcacggagaa ggagtgtgcg    420
cagtttgagg ctgcagtcgg cggtcccgag cagctggctg atcactgg ctctcgagca    480
catactcgtt tcaccgggcc ccagattctc aaggtcaagg aacgcaaccc caaggtattc    540
aaggccacgt cacgggtcca gctcatatcc aactttctag catctctgtt tgccggcaag    600
gcgtgcccct tgatcttgc tgacgcctgt ggaatgaatc tgtgggacat ccagaatggc    660
cagtggtgca gaaactcac agatctcatc accgatgaca cccactcggt cgagtccctc    720
cttggagacg tggaaacaga ccccaaggct ctactgggca aaatctcgcc ctatttcgtc    780
tccaagggct tctctccctc ttgtcaggtg gcacagttca caggcgacaa cccaggcact    840
atgctggctc tccccttaca ggccaatgac gtgattgtgt ctttgggaac atctacgacc    900
gccctcgtcg taacaaacaa gtacatgccc gaccccggat accatgtgtt caaccacccc    960
atggagggat acatgggcat gctgtgctac tgcaacggag gtctagcacg agagaagatc   1020
cgagacgagc ttggaggctg ggacgagttt aatgaggcgg ccgagaccac caacacagtg   1080
tctgctgacg atgtccatgt tggcatctac tttccactac gagaaatcct tcctcgagca   1140
ggtcccttg aacgacgttt catctacaac agacaaagtg aacagcttac agagatggct   1200
tctccagagg actcactggc aaccgaacac aaaccgcagg ctcaaaatct caaggacacg   1260
tggccgccac aaatggacgc cactgccatc attcaaagcc aggccctcag tatcaaaatg   1320
agactccaac gcatgatgca tggcgatatt ggaaaggtgt attttgtggg aggcgcctcg   1380
gtcaacactg ctatctgcag cgtaatgtct gccatcttaa aaccaacaaa gggcgcttgg   1440
```

```
agatgtggtc tggaaatggc aaacgcttgt gccattggaa gtgcccatca cgcctggctt    1500
tgcgacccca acaagacagg ccaggtacag gttcacgaag aagaggtcaa atacaagaat    1560
gtggacacag acgtgctact caaggcgttc aagctggccg aaaacgcctg cctggagaaa    1620
taa                                                                 1623
```

<210> SEQ ID NO 6
<211> LENGTH: 540
<212> TYPE: PRT
<213> ORGANISM: Yarrowia lipolytica

<400> SEQUENCE: 6

```
Met Tyr Leu Gly Leu Asp Leu Ser Thr Gln Gln Leu Lys Gly Ile Ile
  1               5                  10                  15

Leu Asp Thr Lys Thr Leu Asp Thr Val Thr Gln Val His Val Asp Phe
             20                  25                  30

Glu Asp Asp Leu Pro Gln Phe Asn Thr Glu Lys Gly Val Phe His Ser
         35                  40                  45

Ser Thr Val Ala Gly Glu Ile Asn Ala Pro Val Ala Met Trp Gly Ala
     50                  55                  60

Ala Val Asp Leu Leu Ile Glu Arg Leu Ser Lys Glu Ile Asp Leu Ser
 65                  70                  75                  80

Thr Ile Lys Phe Val Ser Gly Ser Cys Gln Gln His Gly Ser Val Tyr
                 85                  90                  95

Leu Asn Ser Ser Tyr Lys Glu Gly Leu Gly Ser Leu Asp Lys His Lys
            100                 105                 110

Asp Leu Ser Thr Gly Val Ser Ser Leu Leu Ala Leu Glu Val Ser Pro
        115                 120                 125

Asn Trp Gln Asp Ala Ser Thr Glu Lys Glu Cys Ala Gln Phe Glu Ala
    130                 135                 140

Ala Val Gly Gly Pro Glu Gln Leu Ala Glu Ile Thr Gly Ser Arg Ala
145                 150                 155                 160

His Thr Arg Phe Thr Gly Pro Gln Ile Leu Lys Val Lys Glu Arg Asn
                165                 170                 175

Pro Lys Val Phe Lys Ala Thr Ser Arg Val Gln Leu Ile Ser Asn Phe
            180                 185                 190

Leu Ala Ser Leu Phe Ala Gly Lys Ala Cys Pro Phe Asp Leu Ala Asp
        195                 200                 205

Ala Cys Gly Met Asn Leu Trp Asp Ile Gln Asn Gly Gln Trp Cys Lys
    210                 215                 220

Lys Leu Thr Asp Leu Ile Thr Asp Thr His Ser Val Glu Ser Leu
225                 230                 235                 240

Leu Gly Asp Val Glu Thr Asp Pro Lys Ala Leu Leu Gly Lys Ile Ser
                245                 250                 255

Pro Tyr Phe Val Ser Lys Gly Phe Ser Pro Ser Cys Gln Val Ala Gln
            260                 265                 270

Phe Thr Gly Asp Asn Pro Gly Thr Met Leu Ala Leu Pro Leu Gln Ala
        275                 280                 285

Asn Asp Val Ile Val Ser Leu Gly Thr Ser Thr Thr Ala Leu Val Val
    290                 295                 300

Thr Asn Lys Tyr Met Pro Asp Pro Gly Tyr His Val Phe Asn His Pro
305                 310                 315                 320

Met Glu Gly Tyr Met Gly Met Leu Cys Tyr Cys Asn Gly Gly Leu Ala
                325                 330                 335
```

```
Arg Glu Lys Ile Arg Asp Glu Leu Gly Gly Trp Asp Glu Phe Asn Glu
            340                 345                 350

Ala Ala Glu Thr Thr Asn Thr Val Ser Ala Asp Asp Val His Val Gly
        355                 360                 365

Ile Tyr Phe Pro Leu Arg Glu Ile Leu Pro Arg Ala Gly Pro Phe Glu
    370                 375                 380

Arg Arg Phe Ile Tyr Asn Arg Gln Ser Glu Gln Leu Thr Glu Met Ala
385                 390                 395                 400

Ser Pro Glu Asp Ser Leu Ala Thr Glu His Lys Pro Gln Ala Gln Asn
                405                 410                 415

Leu Lys Asp Thr Trp Pro Pro Gln Met Asp Ala Thr Ala Ile Ile Gln
            420                 425                 430

Ser Gln Ala Leu Ser Ile Lys Met Arg Leu Gln Arg Met Met His Gly
        435                 440                 445

Asp Ile Gly Lys Val Tyr Phe Val Gly Gly Ala Ser Val Asn Thr Ala
    450                 455                 460

Ile Cys Ser Val Met Ser Ala Ile Leu Lys Pro Thr Lys Gly Ala Trp
465                 470                 475                 480

Arg Cys Gly Leu Glu Met Ala Asn Ala Cys Ala Ile Gly Ser Ala His
                485                 490                 495

His Ala Trp Leu Cys Asp Pro Asn Lys Thr Gly Gln Val Gln Val His
            500                 505                 510

Glu Glu Val Lys Tyr Lys Asn Val Asp Thr Asp Val Leu Leu Lys
        515                 520                 525

Ala Phe Lys Leu Ala Glu Asn Ala Cys Leu Glu Lys
    530                 535                 540

<210> SEQ ID NO 7
<211> LENGTH: 1314
<212> TYPE: DNA
<213> ORGANISM: Piromyces sp E2

<400> SEQUENCE: 7
atggctaaag agtacttccc acagattcag aagataaagt tcgagggcaa agattctaaa      60 aacccttttgg cttttccacta ctatgatgca gagaaggaag tcatgggaaa gaaaatgaag     120
gattggttga gatttgctat ggcttggtgg catactttgt gtgctgaagg tgcagaccag     180
ttcggcggtg gcactaagtc ttttccttgg aatgagggta ctgatgccat gaaatcgcc      240 aaacaaaagg tagacgctgg ttttgagatc atgcagaagt gggcatccc ttattactgt      300 tttcacgatg tcgatttggt gagtgaaggc aatagtatag aggaatacga gtctaactta     360
aaggcagtcg ttgcctatt gaaggagaag caaaaggaaa ctggtatcaa attgttgtgg     420
agtactgcta acgtcttcgg ccacaaaaga tacatgaacg gtgcttctac taatccagac     480
tttgatgtag tcgctagagc tatagtccag attaagaatg ctatcgacgc cggaattgag     540
ttgggagctg agaactatgt tttttggga ggtagggaag gctatatgtc tttgttgaat      600
actgaccaga agagagagaa agaacacatg gcaacaatgt taactatggc aagagattac     660
gcaaggagta aggctttaa ggcactttt ttgattgaac ctaagcctat ggaaccaact       720
aaacaccaat atgatgttga cactgaaaca gccatcggtt tcttgaaggc ccacaacttg     780
gataaagatt ttaaggtaaa cattgaggtc aatcacgcca ccttggccgg tcacactttc     840
gaacatgaat tggcttgtgc tgttgatgct ggaatgttgg gttctattga tgcaaataga     900
ggcgattatc agaatggttg ggatactgat caatttccaa tcgaccaata cgaattggtt     960
```

-continued

```
caagcctgga tggaaatcat aagaggtggt ggctttgtaa ctggtggaac taacttcgat    1020
gccaaaacaa gaagaaactc cactgacttg gaggatatca ttattgctca cgtttccggt    1080
atggatgcaa tggccagggc cttggagaac gctgctaagt tgttacaaga atcccctac     1140 actaagatga agaaagagag gtacgcatca ttcgattctg gaatcggcaa ggattttgag    1200
gacggaaagt tgactttaga gcaggtttat gagtacggta aaaagaatgg cgagcctaaa    1260
caaacctctg gtaagcagga attgtacgaa gctattgtcg caatgtatca ataa          1314
```

<210> SEQ ID NO 8
<211> LENGTH: 437
<212> TYPE: PRT
<213> ORGANISM: Piromyces sp E2

<400> SEQUENCE: 8

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320
```

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 9
<211> LENGTH: 1545
<212> TYPE: DNA
<213> ORGANISM: Yarrowia lipolytica

<400> SEQUENCE: 9

```
atgactatcg actcacaata ctacaagtcg cgagacaaaa acgacacggc acccaaaatc      60
gcgggaatcc gatatgcccc gctatcgaca ccattactca accgatgtga gaccttctct     120
ctggtctggc acattttcag cattcccact ttcctcacaa tttttcatgct atgctgcgca    180 attccactgc tctggccatt tgtgattgcg tatgtagtgt acgctgttaa agacgactcc     240
ccgtccaacg gaggagtggt caagcgatac tcgcctattt caagaaactt cttcatctgg     300
aagctctttg ccgctacttt ccccataact ctgcacaaga cggtggatct ggagcccacg     360
cacacatact accctctgga cgtccaggag tatcacctga ttgctgagag atactggccg     420
cagaacaagt acctccgagc aatcatctcc accatcgagt actttctgcc cgccttcatg     480
aaacggtctc tttctatcaa cgagcaggag cagcctgccg agcgagatcc tctcctgtct     540
cccgtttctc ccagctctcc gggttctcaa cctgacaagt ggattaacca cgacagcaga     600
tatagccgtg gagaatcatc tggctccaac ggccacgcct cgggctccga acttaacggc     660
aacggcaaca atggcaccac taaccgacga cctttgtcgt ccgcctctgc tggctccact     720
gcatctgatt ccacgcttct taacgggtcc ctcaactcct acgccaacca gatcattggc     780
gaaaacgacc acagctgtc gcccacaaaa ctcaagccca ctggcagaaa atacatcttc     840
ggctaccacc cccacggcat tatcggcatg ggagcctttg tggaattgc caccgaggga     900 gctggatggt ccaagctctt ccgggcatc cctgtttctc ttatgactct caccaacaac     960
ttccgagtgc ctctctacag agagtacctc atgagtctgg gagtcgcttc tgtctccaag    1020
aagtcctgca aggccctcct caagcgaaac cagtctatct gcattgtcgt tggtggagca    1080
caggaaagtc ttctggccag acccggtgtc atggacctgg tgctactcaa gcgaaagggt    1140
tttgttcgac ttggtatgga ggtcggaaat gtcgcccttg ttcccatcat ggcctttggt    1200
gagaacgacc tctatgacca ggttagcaac gacaagtcgt ccaagctgta ccgattccag    1260
cagtttgtca agaacttcct tggattcacc cttcctttga tgcatgcccg aggcgtcttc    1320
aactacgatg tcggtcttgt ccccctacagg cgacccgtca acattgtggt tggttccccc    1380
```

-continued

```
attgacttgc cttatctccc acaccccacc gacgaagaag tgtccgaata ccacgaccga    1440
tacatcgccg agctgcagcg aatctacaac gagcacaagg atgaatattt catcgattgg    1500
accgaggagg gcaaaggagc cccagagttc cgaatgattg agtaa                    1545
```

<210> SEQ ID NO 10
<211> LENGTH: 514
<212> TYPE: PRT
<213> ORGANISM: Yarrowia lipolytica

<400> SEQUENCE: 10

```
Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350
```

```
Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu

<210> SEQ ID NO 11
<211> LENGTH: 7270
<212> TYPE: DNA
<213> ORGANISM: Yarrowia lipolytica

<400> SEQUENCE: 11
atgcgactgc aattgaggac actaacacgt cggttttca ggtgagtaaa cgacggtggc      60
cgtggccacg acagccgagg cgtcacgatg ggccagacga gcacattctc gccgccacaa     120
cctcgccagc acaagaaact aacccagtat ggcttcagga tcttcaacgc cagatgtggc     180
tcccttggtg gaccccaaca ttcacaaagg tctcgcctct catttctttg gactcaattc     240
tgtccacaca gccaagccct caaaagtcaa ggagtttgtg gcttctcacg gaggtcatac     300
agttatcaac aaggtgagta tttgacgttt agactgtata acaggcggcc gcagtgcaac     360
aacgaccaaa aagggtcgaa aagggtcgaa aacggacac  aaaagctgga aaacaagagt     420
gtaatacatt cttacacgtc caattgttag acaaacacgg ctgttcggtc caaaaccac      480 cagtatcacc tattttccac ttgtgtctcg gatctgatca taatctgatc tcaagatgaa     540
atttacgcca ccgacatgat attgtgattt tcggattctc cagaccgagc agattccagc     600
aataccacca cttgcccacc ttcagcggcc tctcggcgcg attcgccact ttccccaacg     660
agtgttacta acccaggtcc tcatcgctaa caacggtatt gccgcagtaa aggagatccg     720
ttcagtacga aaatgggcct acgagacctt ggcgacgag cgagcaatct cgttcaccgt      780
catggccacc cccgaagatc tcgctgccaa cgccgactac attagaatgg ccgatcagta     840
cgtcgaggtg cccggaggaa ccaacaacaa caactacgcc aacgtcgagc tgattgtcga     900
cgtggctgag cgattcggcg tcgatgccgt gtgggccgga tggggccatg ccagtgaaaa     960
tcccctgctc cccgagtcgc tagcggcctc tccccgcaag attgtcttca tcggccctcc    1020
cggagctgcc atgagatctc tgggagacaa aatttcttct accattgtgg cccagcacgc    1080
aaaggtcccg tgtatcccgt ggtctggaac cggagtggac gaggttgtgg ttgacaagag    1140
```

```
caccaacctc gtgtccgtgt ccgaggaggt gtacaccaag ggctgcacca ccggtcccaa    1200
gcagggtctg gagaaggcta agcagattgg attccccgtg atgatcaagg cttccgaggg    1260
aggaggagga aagggtattc gaaaggttga gcgagaggag gacttcgagg ctgcttacca    1320
ccaggtcgag ggagagatcc ccggctcgcc catcttcatt atgcagcttg caggcaatgc    1380
ccggcatttg gaggtgcagc ttctggctga tcagtacggc aacaatattt cactgtttgg    1440
tcgagattgt tcggttcagc gacggcatca aaagattatt gaggaggctc ctgtgactgt    1500
ggctggccag cagaccttca ctgccatgga gaaggctgcc gtgcgactcg gtaagcttgt    1560
cggatatgtc tctgcaggta ccgttgaata tctgtattcc catgaggacg acaagttcta    1620
cttcttggag ctgaatcctc gtcttcaggt cgaacatcct accaccgaga tggtcaccgg    1680
tgtcaacctg cccgctgccc agcttcagat cgccatgggt atcccccctcg atcgaatcaa    1740 ggacattcgt ctcttttacg gtgttaaccc tcacaccacc actccaattg atttcgactt    1800
ctcgggcgag gatgctgata agacacagcg acgtcccgtc ccccgaggtc acaccactgc    1860
ttgccgaatc acatccgagg accctggaga gggtttcaag ccctccggag gtactatgca    1920
cgagctcaac ttccgatcct cgtccaacgt gtggggttac ttctccgttg gtaaccaggg    1980
aggtatccat tcgttctcgg attcgcagtt tggtcacatc ttcgccttcg gtgagaaccg    2040
aagtgcgtct cgaaagcaca tggttgttgc tttgaaggaa ctatctattc gaggtgactt    2100
ccgaaccacc gtcgagtacc tcatcaagct gctggagaca ccggacttcg aggacaacac    2160
catcaccacc ggctggctgg atgagcttat ctccaacaag ctgactgccg agcgacccga    2220
ctcgttcctc gctgttgttt gtggtgctgc taccaaggcc catcgagctt ccgaggactc    2280
tattgccacc tacatggctt cgctagagaa gggccaggtc cctgctcgag acattctcaa    2340
gacccttttc cccgttgact tcatctacga gggccagcgg tacaagttca ccgccacccg    2400
gtcgtctgag gactcttaca cgctgttcat caacggttct cgatgcgaca ttggagttag    2460 acctcttttct gacggtggta ttctgtgtct tgtaggtggg agatcccaca atgtctactg    2520
gaaggaggag gttggagcca cgcgactgtc tgttgactcc aagacctgcc ttctcgaggt    2580
ggagaacgac cccactcagc ttcgatctcc ctctcccggt aagctggtta agttcctggt    2640
cgagaacggc gaccacgtgc gagccaacca gccctatgcc gagattgagg tcatgaagat    2700
gtacatgact ctcactgctc aggaggacgg tattgtccag ctgatgaagc agcccggttc    2760
caccatcgag gctggcgaca tcctcggtat cttggcccctt gatgatcctt ccaaggtcaa    2820
gcatgccaag cccttttgagg gccagcttcc cgagcttgga ccccccactc tcagcggtaa    2880
caagcctcat cagcgatacg agcactgcca gaacgtgctc cataacattc tgcttggttt    2940
cgataaccag gtggtgatga agtccactct tcaggagatg gttggtctgc tccgaaaccc    3000
tgagcttcct tatctccagt gggctcatca ggtgtcttct ctgcacaccc gaatgagcgc    3060
caagctggat gctactcttg ctggtctcat tgacaaggcc aagcagcgag gtggcgagtt    3120
tcctgccaag cagcttctgc gagcccttga gaaggaggcg agctctggcg aggtcgatgc    3180
gctcttccag caaactcttg ctcctctgtt tgaccttgct cgagagtacc aggacggtct    3240
tgctatccac gagcttcagg ttgctgcagg ccttctgcag gcctactacg actctgaggc    3300
ccggttctgc ggacccaacg tacgtgacga ggatgtcatt ctcaagcttc gagaggagaa    3360
ccgagattct cttcgaaagg ttgtgatggc ccagctgtct cattctcgag tcggagccaa    3420
gaacaacctt gtgctggccc ttctcgatga atacaaggtg gccgaccagg ctggcaccga    3480
ctctcctgcc tccaacgtgc acgttgcaaa gtacttgcga cctgtgctgc gaaagattgt    3540
```

```
ggagctggaa tctcgagctt ctgccaaggt atctctgaaa gcccgagaga ttctcatcca    3600
gtgcgctctg ccctctctaa aggagcgaac tgaccagctt gagcacattc tgcgatcttc    3660
tgtcgtcgag tctcgatacg gagaggttgg tctggagcac cgaactcccc gagccgatat    3720
tctcaaggag gttgtcgact ccaagtacat tgtctttgat gtgcttgccc agttctttgc    3780
ccacgatgat ccctggatcg tccttgctgc cctggagctg tacatccgac gagcttgcaa    3840
ggcctactcc atcctggaca tcaactacca ccaggactcg gacctgcctc ccgtcatctc    3900
gtggcgattt agactgccta ccatgtcgtc tgctttgtac aactcagtag tgtcttctgg    3960
ctccaaaacc cccacttccc cctcggtgtc tcgagctgat tccgtctccg acttttcgta    4020
caccgttgag cgagactctg ctcccgctcg aaccggagcg attgttgccg tgcctcatct    4080
ggatgatctg gaggatgctc tgactcgtgt tctggagaac ctgcccaaac ggggcgctgg    4140
tcttgccatc tctgttggtg ctagcaacaa gagtgccgct gcttctgctc gtgacgctgc    4200
tgctgctgcc gcttcatccg ttgacactgg cctgtccaac atttgcaacg ttatgattgg    4260
tcgggttgat gagtctgatg acgacgacac tctgattgcc cgaatctccc aggtcattga    4320
ggactttaag gaggactttg aggcctgttc tctgcgacga atcaccttct ccttcggcaa    4380
ctcccgaggt acttatccca agtatttcac gttccgaggc cccgcatacg aggaggaccc    4440
cactatccga cacattgagc ctgctctggc cttccagctg gagctcgccc gtctgtccaa    4500
cttcgacatc aagcctgtcc acaccgacaa ccgaaacatc cacgtgtacg aggctactgg    4560
caagaacgct gcttccgaca gcggttctt caccgaggt atcgtacgac ctggtcgtct    4620
tcgagagaac atccccacct cggagtatct catttccgag gctgaccggc tcatgagcga    4680
tattttggac gctctagagg tgattggaac caccaactcg gatctcaacc acattttcat    4740
caacttctca gccgtctttg ctctgaagcc cgaggaggtt gaagctgcct ttggcggttt    4800
cctggagcga tttggccgac gtctgtggcg acttcgagtc accggtgccg agatccgaat    4860
gatggtatcc gaccccgaaa ctggctctgc tttccctctg cgagcaatga tcaacaacgt    4920
ctctggttac gttgtgcagt ctgagctgta cgctgaggcc aagaacgaca agggccagtg    4980
gattttcaag tctctgggca agcccggctc catgcacatg cggtctatca acactcccta    5040
ccccaccaag gagtggctgc agcccaagcg gtacaaggcc catctgatgg gtaccaccta    5100
ctgctatgac ttccccgagc tgttccgaca gtccattgag tcggactgga agaagtatga    5160
cggcaaggct cccgacgatc tcatgacttg caacgagctg attctcgatg aggactctgg    5220
cgagctgcag gaggtgaacc gagagcccgg cgccaacaac gtcggtatgg ttgcgtggaa    5280
gtttgaggcc aagaccccg agtaccctcg aggccgatct ttcatcgtgg tggccaacga    5340
tatcaccttc cagattggtt cgtttggccc tgctgaggac cagttcttct tcaaggtgac    5400
ggagctggct cgaaagctcg gtattcctcg aatctatctg tctgccaact ctggtgctcg    5460
aatcggcatt gctgacgagc tcgttggcaa gtacaaggtt gcgtggaacg acgagactga    5520
cccctccaag ggcttcaagt acctttactt caccccctgag tctcttgcca ccctcaagcc    5580
cgacactgtt gtcaccactg agattgagga ggagggtccc aacggcgtgg agaagcgtca    5640
tgtgatcgac tacattgtcg gagagaagga cggtctcgga gtcgagtgtc tgcggggctc    5700
tggtctcatt gcaggcgcca cttctcgagc ctacaaggat atcttcactc tcactcttgt    5760
cacctgtcga tccgttggta tcggtgctta ccttgttcgt cttggtcaac gagccatcca    5820
gattgagggc cagcccatca ttctcactgg tgccccccgcc atcaacaagc tgcttggtcg    5880
```

-continued

| | |
|---|---|
| agaggtctac tcttccaact tgcagcttgg tggtactcag atcatgtaca acaacggtgt | 5940 |
| gtctcatctg actgcccgag atgatctcaa cggtgtccac aagatcatgc agtggctgtc | 6000 |
| atacatccct gcttctcgag gtcttccagt gcctgttctc cctcacaaga ccgatgtgtg | 6060 |
| ggatcgagac gtgacgttcc agcctgtccg aggcgagcag tacgatgtta gatggcttat | 6120 |
| ttctggccga actctcgagg atggtgcttt cgagtctggt ctctttgaca aggactcttt | 6180 |
| ccaggagact ctgtctggct gggccaaggg tgttgttgtt ggtcgagctc gtcttggcgg | 6240 |
| cattcccttc ggtgtcattg gtgtcgagac tgcgaccgtc gacaatacta cccctgccga | 6300 |
| tcccgccaac ccggactcta ttgagatgag cacctctgaa gccggccagg tttggtaccc | 6360 |
| caactcggcc ttcaagacct ctcaggccat caacgacttc aaccatggtg aggcgcttcc | 6420 |
| tctcatgatt cttgctaact ggcgaggctt ttctggtggt cagcgagaca tgtacaatga | 6480 |
| ggttctcaag tacggatctt tcattgttga tgctctggtt gactacaagc agcccatcat | 6540 |
| ggtgtacatc cctcccaccg gtgagctgcg aggtggttct tgggttgtgg ttgaccccac | 6600 |
| catcaactcg gacatgatgg agatgtacgc tgacgtcgag tctcgaggtg gtgtgctgga | 6660 |
| gcccgaggga atggtcggta tcaagtaccg acgagacaag ctactggaca ccatggctcg | 6720 |
| tctggatccc gagtactcct ctctcaagaa gcagcttgag gagtctcccg attctgagga | 6780 |
| gctcaaggtc aagctcagcg tgcgagagaa gtctctcatg cccatctacc agcagatctc | 6840 |
| cgtgcagttt gccgacttgc atgaccgagc tggccgaatg gaggccaagg tgtcattcg | 6900 |
| tgaggctctt gtgtggaagg atgctcgtcg attcttcttc tggcgaatcc gacgacgatt | 6960 |
| agtcgaggag tacctcatta ccaagatcaa tagcattctg ccctcttgca ctcggcttga | 7020 |
| gtgtctggct cgaatcaagt cgtggaagcc tgccactctt gatcagggct ctgaccgggg | 7080 |
| tgttgccgag tggtttgacg agaactctga tgccgtctct gctcgactca gcgagctcaa | 7140 |
| gaaggacgct tctgcccagt cgtttgcttc tcaactgaga aaggaccgac agggtactct | 7200 |
| ccagggcatg aagcaggctc tcgcttctct ttctgaggct gagcgggctg agctgctcaa | 7260 |
| ggggttgtga | 7270 |

<210> SEQ ID NO 12
<211> LENGTH: 2266
<212> TYPE: PRT
<213> ORGANISM: Yarrowia lipolytica

<400> SEQUENCE: 12

Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Phe Gly Leu Asn Ser Val His Thr
        35                  40                  45

Ala Lys Pro Ser Lys Val Lys Glu Phe Val Ala Ser His Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

-continued

Gly Gly Thr Asn Asn Asn Tyr Ala Asn Val Glu Leu Ile Val Asp
130                     135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
            165                 170                 175

Lys Ile Val Phe Ile Gly Pro Pro Gly Ala Ala Met Arg Ser Leu Gly
                180                 185                 190

Asp Lys Ile Ser Ser Thr Ile Ala Gln His Ala Lys Val Pro Cys
        195                 200                 205

Ile Pro Trp Ser Gly Thr Gly Val Asp Glu Val Val Asp Lys Ser
210                 215                 220

Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
            245                 250                 255

Val Met Ile Lys Ala Ser Glu Gly Gly Gly Lys Gly Ile Arg Lys
                260                 265                 270

Val Glu Arg Glu Glu Asp Phe Glu Ala Ala Tyr His Gln Val Glu Gly
        275                 280                 285

Glu Ile Pro Gly Ser Pro Ile Phe Ile Met Gln Leu Ala Gly Asn Ala
290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg Arg His Gln Lys Ile
            325                 330                 335

Ile Glu Glu Ala Pro Val Thr Val Ala Gly Gln Gln Thr Phe Thr Ala
                340                 345                 350

Met Glu Lys Ala Ala Val Arg Leu Gly Lys Leu Val Gly Tyr Val Ser
        355                 360                 365

Ala Gly Thr Val Glu Tyr Leu Tyr Ser His Glu Asp Asp Lys Phe Tyr
370                 375                 380

Phe Leu Glu Leu Asn Pro Arg Leu Gln Val Glu His Pro Thr Thr Glu
385                 390                 395                 400

Met Val Thr Gly Val Asn Leu Pro Ala Ala Gln Leu Gln Ile Ala Met
            405                 410                 415

Gly Ile Pro Leu Asp Arg Ile Lys Asp Ile Arg Leu Phe Tyr Gly Val
                420                 425                 430

Asn Pro His Thr Thr Thr Pro Ile Asp Phe Asp Phe Ser Gly Glu Asp
        435                 440                 445

Ala Asp Lys Thr Gln Arg Arg Pro Val Pro Arg Gly His Thr Thr Ala
450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Asn Val Trp Gly
            485                 490                 495

Tyr Phe Ser Val Gly Asn Gln Gly Gly Ile His Ser Phe Ser Asp Ser
                500                 505                 510

Gln Phe Gly His Ile Phe Ala Phe Gly Glu Asn Arg Ser Ala Ser Arg
        515                 520                 525

Lys His Met Val Val Ala Leu Lys Glu Leu Ser Ile Arg Gly Asp Phe
530                 535                 540

-continued

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
            580                 585                 590

Ala Ala Thr Lys Ala His Arg Ala Ser Glu Asp Ser Ile Ala Thr Tyr
        595                 600                 605

Met Ala Ser Leu Glu Lys Gly Gln Val Pro Ala Arg Asp Ile Leu Lys
    610                 615                 620

Thr Leu Phe Pro Val Asp Phe Ile Tyr Glu Gly Gln Arg Tyr Lys Phe
625                 630                 635                 640

Thr Ala Thr Arg Ser Ser Glu Asp Ser Tyr Thr Leu Phe Ile Asn Gly
                645                 650                 655

Ser Arg Cys Asp Ile Gly Val Arg Pro Leu Ser Asp Gly Gly Ile Leu
            660                 665                 670

Cys Leu Val Gly Gly Arg Ser His Asn Val Tyr Trp Lys Glu Val
        675                 680                 685

Gly Ala Thr Arg Leu Ser Val Asp Ser Lys Thr Cys Leu Leu Glu Val
    690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                725                 730                 735

Ala Glu Ile Glu Val Met Lys Met Tyr Met Thr Leu Thr Ala Gln Glu
            740                 745                 750

Asp Gly Ile Val Gln Leu Met Lys Gln Pro Gly Ser Thr Ile Glu Ala
        755                 760                 765

Gly Asp Ile Leu Gly Ile Leu Ala Leu Asp Asp Pro Ser Lys Val Lys
    770                 775                 780

His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
            820                 825                 830

Thr Leu Gln Glu Met Val Gly Leu Leu Arg Asn Pro Glu Leu Pro Tyr
        835                 840                 845

Leu Gln Trp Ala His Gln Val Ser Ser Leu His Thr Arg Met Ser Ala
    850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Thr Leu Ala Pro
            900                 905                 910

Leu Phe Asp Leu Ala Arg Glu Tyr Gln Asp Gly Leu Ala Ile His Glu
        915                 920                 925

Leu Gln Val Ala Ala Gly Leu Leu Ala Tyr Tyr Asp Ser Glu Ala
    930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu

-continued

```
                965                 970                 975
Ser His Ser Arg Val Gly Ala Lys Asn Asn Leu Val Leu Ala Leu Leu
                    980                 985                 990
Asp Glu Tyr Lys Val Ala Asp Gln Ala Gly Thr Asp Ser Pro Ala Ser
                    995                1000                1005
Asn Val His Val Ala Lys Tyr Leu Arg Pro Val Leu Arg Lys Ile
1010                1015                1020
Val Glu Leu Glu Ser Arg Ala Ser Ala Lys Val Ser Leu Lys Ala
1025                1030                1035
Arg Glu Ile Leu Ile Gln Cys Ala Leu Pro Ser Leu Lys Glu Arg
1040                1045                1050
Thr Asp Gln Leu Glu His Ile Leu Arg Ser Ser Val Val Glu Ser
1055                1060                1065
Arg Tyr Gly Glu Val Gly Leu Glu His Arg Thr Pro Arg Ala Asp
1070                1075                1080
Ile Leu Lys Glu Val Val Asp Ser Lys Tyr Ile Val Phe Asp Val
1085                1090                1095
Leu Ala Gln Phe Phe Ala His Asp Asp Pro Trp Ile Val Leu Ala
1100                1105                1110
Ala Leu Glu Leu Tyr Ile Arg Arg Ala Cys Lys Ala Tyr Ser Ile
1115                1120                1125
Leu Asp Ile Asn Tyr His Gln Asp Ser Asp Leu Pro Pro Val Ile
1130                1135                1140
Ser Trp Arg Phe Arg Leu Pro Thr Met Ser Ser Ala Leu Tyr Asn
1145                1150                1155
Ser Val Val Ser Ser Gly Ser Lys Thr Pro Thr Ser Pro Ser Val
1160                1165                1170
Ser Arg Ala Asp Ser Val Ser Asp Phe Ser Tyr Thr Val Glu Arg
1175                1180                1185
Asp Ser Ala Pro Ala Arg Thr Gly Ala Ile Val Ala Val Pro His
1190                1195                1200
Leu Asp Asp Leu Glu Asp Ala Leu Thr Arg Val Leu Glu Asn Leu
1205                1210                1215
Pro Lys Arg Gly Ala Gly Leu Ala Ile Ser Val Gly Ala Ser Asn
1220                1225                1230
Lys Ser Ala Ala Ala Ser Ala Arg Asp Ala Ala Ala Ala Ala Ala
1235                1240                1245
Ser Ser Val Asp Thr Gly Leu Ser Asn Ile Cys Asn Val Met Ile
1250                1255                1260
Gly Arg Val Asp Glu Ser Asp Asp Asp Thr Leu Ile Ala Arg
1265                1270                1275
Ile Ser Gln Val Ile Glu Asp Phe Lys Glu Asp Phe Glu Ala Cys
1280                1285                1290
Ser Leu Arg Arg Ile Thr Phe Ser Phe Gly Asn Ser Arg Gly Thr
1295                1300                1305
Tyr Pro Lys Tyr Phe Thr Phe Arg Gly Pro Ala Tyr Glu Glu Asp
1310                1315                1320
Pro Thr Ile Arg His Ile Glu Pro Ala Leu Ala Phe Gln Leu Glu
1325                1330                1335
Leu Ala Arg Leu Ser Asn Phe Asp Ile Lys Pro Val His Thr Asp
1340                1345                1350
Asn Arg Asn Ile His Val Tyr Glu Ala Thr Gly Lys Asn Ala Ala
1355                1360                1365
```

-continued

```
Ser Asp Lys Arg Phe Phe Thr Arg Gly Ile Val Arg Pro Gly Arg
    1370                1375                1380

Leu Arg Glu Asn Ile Pro Thr Ser Glu Tyr Leu Ile Ser Glu Ala
    1385                1390                1395

Asp Arg Leu Met Ser Asp Ile Leu Asp Ala Leu Glu Val Ile Gly
    1400                1405                1410

Thr Thr Asn Ser Asp Leu Asn His Ile Phe Ile Asn Phe Ser Ala
    1415                1420                1425

Val Phe Ala Leu Lys Pro Glu Glu Val Glu Ala Ala Phe Gly Gly
    1430                1435                1440

Phe Leu Glu Arg Phe Gly Arg Arg Leu Trp Arg Leu Arg Val Thr
    1445                1450                1455

Gly Ala Glu Ile Arg Met Met Val Ser Asp Pro Glu Thr Gly Ser
    1460                1465                1470

Ala Phe Pro Leu Arg Ala Met Ile Asn Asn Val Ser Gly Tyr Val
    1475                1480                1485

Val Gln Ser Glu Leu Tyr Ala Glu Ala Lys Asn Asp Lys Gly Gln
    1490                1495                1500

Trp Ile Phe Lys Ser Leu Gly Lys Pro Gly Ser Met His Met Arg
    1505                1510                1515

Ser Ile Asn Thr Pro Tyr Pro Thr Lys Glu Trp Leu Gln Pro Lys
    1520                1525                1530

Arg Tyr Lys Ala His Leu Met Gly Thr Thr Tyr Cys Tyr Asp Phe
    1535                1540                1545

Pro Glu Leu Phe Arg Gln Ser Ile Glu Ser Asp Trp Lys Lys Tyr
    1550                1555                1560

Asp Gly Lys Ala Pro Asp Asp Leu Met Thr Cys Asn Glu Leu Ile
    1565                1570                1575

Leu Asp Glu Asp Ser Gly Glu Leu Gln Glu Val Asn Arg Glu Pro
    1580                1585                1590

Gly Ala Asn Asn Val Gly Met Val Ala Trp Lys Phe Glu Ala Lys
    1595                1600                1605

Thr Pro Glu Tyr Pro Arg Gly Arg Ser Phe Ile Val Val Ala Asn
    1610                1615                1620

Asp Ile Thr Phe Gln Ile Gly Ser Phe Gly Pro Ala Glu Asp Gln
    1625                1630                1635

Phe Phe Phe Lys Val Thr Glu Leu Ala Arg Lys Leu Gly Ile Pro
    1640                1645                1650

Arg Ile Tyr Leu Ser Ala Asn Ser Gly Ala Arg Ile Gly Ile Ala
    1655                1660                1665

Asp Glu Leu Val Gly Lys Tyr Lys Val Ala Trp Asn Asp Glu Thr
    1670                1675                1680

Asp Pro Ser Lys Gly Phe Lys Tyr Leu Tyr Phe Thr Pro Glu Ser
    1685                1690                1695

Leu Ala Thr Leu Lys Pro Asp Thr Val Val Thr Thr Glu Ile Glu
    1700                1705                1710

Glu Glu Gly Pro Asn Gly Val Glu Lys Arg His Val Ile Asp Tyr
    1715                1720                1725

Ile Val Gly Glu Lys Asp Gly Leu Gly Val Glu Cys Leu Arg Gly
    1730                1735                1740

Ser Gly Leu Ile Ala Gly Ala Thr Ser Arg Ala Tyr Lys Asp Ile
    1745                1750                1755
```

```
Phe Thr Leu Thr Leu Val Thr Cys Arg Ser Val Gly Ile Gly Ala
1760                    1765                1770

Tyr Leu Val Arg Leu Gly Gln Arg Ala Ile Gln Ile Glu Gly Gln
    1775                1780                1785

Pro Ile Ile Leu Thr Gly Ala Pro Ala Ile Asn Lys Leu Leu Gly
    1790                1795                1800

Arg Glu Val Tyr Ser Ser Asn Leu Gln Leu Gly Gly Thr Gln Ile
    1805                1810                1815

Met Tyr Asn Asn Gly Val Ser His Leu Thr Ala Arg Asp Asp Leu
    1820                1825                1830

Asn Gly Val His Lys Ile Met Gln Trp Leu Ser Tyr Ile Pro Ala
    1835                1840                1845

Ser Arg Gly Leu Pro Val Pro Val Leu Pro His Lys Thr Asp Val
    1850                1855                1860

Trp Asp Arg Asp Val Thr Phe Gln Pro Val Arg Gly Glu Gln Tyr
    1865                1870                1875

Asp Val Arg Trp Leu Ile Ser Gly Arg Thr Leu Glu Asp Gly Ala
    1880                1885                1890

Phe Glu Ser Gly Leu Phe Asp Lys Asp Ser Phe Gln Glu Thr Leu
    1895                1900                1905

Ser Gly Trp Ala Lys Gly Val Val Gly Arg Ala Arg Leu Gly
    1910                1915                1920

Gly Ile Pro Phe Gly Val Ile Gly Val Glu Thr Ala Thr Val Asp
    1925                1930                1935

Asn Thr Thr Pro Ala Asp Pro Ala Asn Pro Asp Ser Ile Glu Met
    1940                1945                1950

Ser Thr Ser Glu Ala Gly Gln Val Trp Tyr Pro Asn Ser Ala Phe
    1955                1960                1965

Lys Thr Ser Gln Ala Ile Asn Asp Phe Asn His Gly Glu Ala Leu
    1970                1975                1980

Pro Leu Met Ile Leu Ala Asn Trp Arg Gly Phe Ser Gly Gly Gln
    1985                1990                1995

Arg Asp Met Tyr Asn Glu Val Leu Lys Tyr Gly Ser Phe Ile Val
    2000                2005                2010

Asp Ala Leu Val Asp Tyr Lys Gln Pro Ile Met Val Tyr Ile Pro
    2015                2020                2025

Pro Thr Gly Glu Leu Arg Gly Gly Ser Trp Val Val Val Asp Pro
    2030                2035                2040

Thr Ile Asn Ser Asp Met Met Glu Met Tyr Ala Asp Val Glu Ser
    2045                2050                2055

Arg Gly Gly Val Leu Glu Pro Glu Gly Met Val Gly Ile Lys Tyr
    2060                2065                2070

Arg Arg Asp Lys Leu Leu Asp Thr Met Ala Arg Leu Asp Pro Glu
    2075                2080                2085

Tyr Ser Ser Leu Lys Lys Gln Leu Glu Glu Ser Pro Asp Ser Glu
    2090                2095                2100

Glu Leu Lys Val Lys Leu Ser Val Arg Glu Lys Ser Leu Met Pro
    2105                2110                2115

Ile Tyr Gln Gln Ile Ser Val Gln Phe Ala Asp Leu His Asp Arg
    2120                2125                2130

Ala Gly Arg Met Glu Ala Lys Gly Val Ile Arg Glu Ala Leu Val
    2135                2140                2145

Trp Lys Asp Ala Arg Arg Phe Phe Phe Trp Arg Ile Arg Arg Arg
```

```
                        2150                2155                2160
Leu Val Glu Glu Tyr Leu Ile Thr Lys Ile Asn Ser Ile Leu Pro
    2165                2170                    2175

Ser Cys Thr Arg Leu Glu Cys Leu Ala Arg Ile Lys Ser Trp Lys
    2180                2185                    2190

Pro Ala Thr Leu Asp Gln Gly Ser Asp Arg Gly Val Ala Glu Trp
    2195                2200                    2205

Phe Asp Glu Asn Ser Asp Ala Val Ser Ala Arg Leu Ser Glu Leu
    2210                2215                    2220

Lys Lys Asp Ala Ser Ala Gln Ser Phe Ala Ser Gln Leu Arg Lys
    2225                2230                    2235

Asp Arg Gln Gly Thr Leu Gln Gly Met Lys Gln Ala Leu Ala Ser
    2240                2245                    2250

Leu Ser Glu Ala Glu Arg Ala Glu Leu Leu Lys Gly Leu
    2255                2260                    2265

<210> SEQ ID NO 13
<211> LENGTH: 1449
<212> TYPE: DNA
<213> ORGANISM: Yarrowia lipolytica

<400> SEQUENCE: 13
atggtgaaaa acgtggacca agtggatctc tcgcaggtcg acaccattgc ctccggccga      60
gatgtcaact acaaggtcaa gtacacctcc ggcgttaaga tgagccaggg cgcctacgac     120
gacaagggcc gccacatttc cgagcagccc ttcacctggg ccaactggca ccagcacatc     180
aactggctca acttcattct ggtgattgcg ctgcctctgt cgtcctttgc tgccgctccc     240
ttcgtctcct tcaactggaa gaccgccgcg tttgctgtcg ctattacat gtgcaccggt     300
ctcggtatca ccgccggcta ccaccgaatg tgggcccatc gagcctacaa ggccgctctg     360
cccgttcgaa tcatccttgc tctgtttgga ggaggagctg tcgagggctc catccgatgg     420
tgggcctcgt ctcaccgagt ccaccaccga tggaccgact ccaacaagga cccttacgac     480
gcccgaaagg gattctggtt ctcccacttt ggctggatgc tgcttgtgcc caaccccaag     540
aacaagggcc gaactgacat ttctgacctc aacaacgact gggttgtccg actccagcac     600
aagtactacg tttacgttct cgtcttcatg gccattgttc tgcccaccct cgtctgtggc     660
tttggctggg gcgactggaa gggaggtctt gtctacgccg gtatcatgcg atacaccttt     720
gtgcagcagg tgactttctg tgtcaactcc cttgcccact ggattggaga gcagcccttc     780
gacgaccgac gaactccccg agaccacgct cttaccgccc tggtcacctt ggagagggc     840
taccacaact ccaccacga gttcccctcg gactaccgaa cgccctcat ctggtaccag     900
tacgacccca ccagtggct catctggacc ctcaagcagg ttggtctcgc ctgggacctc     960
cagaccttct cccagaacgc catcgagcag ggtctcgtgc agcagcgaca agaagctg    1020
gacaagtggc gaaacaacct caactggggt atccccattg agcagctgcc tgtcattgag    1080
tttgaggagt tccaagagca ggccaagacc cgagatctgg ttctcatttc tggcattgtc    1140
cacgacgtgt ctgcctttgt cgagcaccac cctggtggaa aggccctcat tatgagcgcc    1200
gtcggcaagg acggtaccgc tgtcttcaac ggaggtgtct accgacactc caacgctggc    1260
cacaacctgc ttgccaccat gcgagtttcg gtcattcgag gcggcatgga ggttgaggtg    1320
tggaagactg cccagaacga aaagaaggac cagaacattg tctccgatga gagtggaaac    1380
cgaatccacc gagctggtct ccaggccacc cgggtcgaga accccggtat gtctggcatg    1440
``` gctgcttag                                                                    1449

<210> SEQ ID NO 14
<211> LENGTH: 482
<212> TYPE: PRT
<213> ORGANISM: Yarrowia lipolytica

<400> SEQUENCE: 14

```
Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320

Gln Thr Phe Ser Gln Asn Ala Ile Glu Gln Gly Leu Val Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Phe Gln Glu Gln Ala
        355                 360                 365
```

```
                Lys Thr Arg Asp Leu Val Leu Ile Ser Gly Ile Val His Asp Val Ser
                    370                 375                 380

Ala Phe Val Glu His His Pro Gly Gly Lys Ala Leu Ile Met Ser Ala
                385                 390                 395                 400

Val Gly Lys Asp Gly Thr Ala Val Phe Asn Gly Val Tyr Arg His
                                    405                 410                 415

Ser Asn Ala Gly His Asn Leu Leu Ala Thr Met Arg Val Ser Val Ile
                                420                 425                 430

Arg Gly Gly Met Glu Val Glu Val Trp Lys Thr Ala Gln Asn Glu Lys
                                435                 440                 445

Lys Asp Gln Asn Ile Val Ser Asp Glu Ser Gly Asn Arg Ile His Arg
                450                 455                 460

Ala Gly Leu Gln Ala Thr Arg Val Glu Asn Pro Gly Met Ser Gly Met
                465                 470                 475                 480

Ala Ala

<210> SEQ ID NO 15
<211> LENGTH: 1953
<212> TYPE: DNA
<213> ORGANISM: Yarrowia lipolytica

<400> SEQUENCE: 15
atgtctgcca acgagaacat ctcccgattc gacgccctg tgggcaagga gcaccccgcc      60
tacgagctct ccataacca cacacgatct ttcgtctatg gtctccagcc tcgagcctgc     120
cagggtatgc tggacttcga cttcatctgt aagcgagaga accctccgt ggccggtgtc     180 atctatccct tcggcggcca gttcgtcacc aagatgtact ggggcaccaa ggagactctt     240
ctccctgtct accagcaggt cgagaaggcc gctgccaagc accccgaggt cgatgtcgtg     300
gtcaactttg cctcctctcg atccgtctac tcctctacca tggagctgct cgagtacccc     360
cagttccgaa ccatcgccat tattgccgag ggtgtccccg agcgacgagc ccagagatc     420 ctccacaagg cccagaagaa gggtgtgacc atcattggtc ccgctaccgt cggaggtatc     480
aagcccggtt gcttcaaggt tggaaacacc ggaggtatga tggacaacat tgtcgcctcc     540
aagctctacc gacccggctc cgttgcctac gtctccaagt ccggaggaat gtccaacgag     600
ctgaacaaca ttatctctca caccaccgac ggtgtctacg agggtattgc tattggtggt     660
gaccgatacc ctggtactac cttcattgac catatcctgc gatacgaggc cgaccccaag     720
tgtaagatca tcgtcctcct tggtgaggtt ggtggtgttg aggagtaccg agtcatcgag     780
gctgttaaga acggccagat caagaagccc atcgtcgctt gggccattgg tacttgtgcc     840
tccatgttca agactgaggt tcagttcggc cacgccggct ccatggccaa ctccgacctg     900
gagactgcca aggctaagaa cgccgccatg aagtctgctg gcttctacgt ccccgatacc     960
ttcgaggaca tgcccgaggt ccttgccgag ctctacgaga gatggtcgc caagggcgag    1020 ctgtctcgaa tctctgagcc tgaggtcccc aagatcccca ttgactactc ttgggcccag    1080
gagcttggtc ttatccgaaa gccgctgct ttcatctcca ctatttccga tgaccgaggc    1140
caggagcttc tgtacgctgg catgcccatt tccgaggttt tcaaggagga cattggtatc    1200
ggcggtgtca tgtctctgct gtggttccga cgacgactcc ccgactacgc ctccaagttt    1260
cttgagatgg ttctcatgct tactgctgac cacggtcccg ccgtatccgg tgccatgaac    1320
accattatca ccaccgagc tggtaaggat ctcattttctt ccctggttgc tggtctcctg    1380
accattggta cccgattcgg aggtgctctt gacggtgctg ccaccgagtt caccactgcc    1440
```

| | |
|---|---:|
| tacgacaagg gtctgtcccc ccgacagttc gttgatacca tgcgaaagca gaacaagctg | 1500 |
| attcctggta ttggccatcg agtcaagtct cgaaacaacc ccgatttccg agtcgagctt | 1560 |
| gtcaaggact ttgttaagaa gaacttcccc tccacccagc tgctcgacta cgcccttgct | 1620 |
| gtcgaggagg tcaccacctc caagaaggac aacctgattc tgaacgttga cggtgctatt | 1680 |
| gctgtttctt ttgtcgatct catgcgatct tgcggtgcct ttactgtgga ggagactgag | 1740 |
| gactacctca agaacggtgt tctcaacggt ctgttcgttc tcggtcgatc cattggtctc | 1800 |
| attgcccacc atctcgatca gaagcgactc aagaccggtc tgtaccgaca tccttgggac | 1860 |
| gatatcacct acctggttgg ccaggaggct atccagaaga agcgagtcga gatcagcgcc | 1920 |
| ggcgacgttt ccaaggccaa gactcgatca tag | 1953 |

<210> SEQ ID NO 16
<211> LENGTH: 650
<212> TYPE: PRT
<213> ORGANISM: Yarrowia lipolytica

<400> SEQUENCE: 16

```
Met Ser Ala Asn Glu Asn Ile Ser Arg Phe Asp Ala Pro Val Gly Lys
1               5                   10                  15

Glu His Pro Ala Tyr Glu Leu Phe His Asn His Thr Arg Ser Phe Val
                20                  25                  30

Tyr Gly Leu Gln Pro Arg Ala Cys Gln Gly Met Leu Asp Phe Asp Phe
            35                  40                  45

Ile Cys Lys Arg Glu Asn Pro Ser Val Ala Gly Val Ile Tyr Pro Phe
        50                  55                  60

Gly Gly Gln Phe Val Thr Lys Met Tyr Trp Gly Thr Lys Glu Thr Leu
65                  70                  75                  80

Leu Pro Val Tyr Gln Gln Val Glu Lys Ala Ala Lys His Pro Glu
                85                  90                  95

Val Asp Val Val Asn Phe Ala Ser Ser Arg Ser Val Tyr Ser Ser
            100                 105                 110

Thr Met Glu Leu Leu Glu Tyr Pro Gln Phe Arg Thr Ile Ala Ile Ile
            115                 120                 125

Ala Glu Gly Val Pro Glu Arg Arg Ala Arg Glu Ile Leu His Lys Ala
        130                 135                 140

Gln Lys Lys Gly Val Thr Ile Ile Gly Pro Ala Thr Val Gly Gly Ile
145                 150                 155                 160

Lys Pro Gly Cys Phe Lys Val Gly Asn Thr Gly Gly Met Met Asp Asn
                165                 170                 175

Ile Val Ala Ser Lys Leu Tyr Arg Pro Gly Ser Val Ala Tyr Val Ser
            180                 185                 190

Lys Ser Gly Gly Met Ser Asn Glu Leu Asn Asn Ile Ile Ser His Thr
        195                 200                 205

Thr Asp Gly Val Tyr Glu Gly Ile Ala Ile Gly Gly Asp Arg Tyr Pro
    210                 215                 220

Gly Thr Thr Phe Ile Asp His Ile Leu Arg Tyr Glu Ala Asp Pro Lys
225                 230                 235                 240

Cys Lys Ile Ile Val Leu Leu Gly Glu Val Gly Gly Val Glu Glu Tyr
                245                 250                 255

Arg Val Ile Glu Ala Val Lys Asn Gly Gln Ile Lys Lys Pro Ile Val
            260                 265                 270

Ala Trp Ala Ile Gly Thr Cys Ala Ser Met Phe Lys Thr Glu Val Gln
        275                 280                 285
```

```
Phe Gly His Ala Gly Ser Met Ala Asn Ser Asp Leu Glu Thr Ala Lys
            290                 295                 300

Ala Lys Asn Ala Ala Met Lys Ser Ala Gly Phe Tyr Val Pro Asp Thr
305                 310                 315                 320

Phe Glu Asp Met Pro Glu Val Leu Ala Glu Leu Tyr Glu Lys Met Val
                325                 330                 335

Ala Lys Gly Glu Leu Ser Arg Ile Ser Glu Pro Glu Val Pro Lys Ile
            340                 345                 350

Pro Ile Asp Tyr Ser Trp Ala Gln Glu Leu Gly Leu Ile Arg Lys Pro
        355                 360                 365

Ala Ala Phe Ile Ser Thr Ile Ser Asp Asp Arg Gly Gln Glu Leu Leu
    370                 375                 380

Tyr Ala Gly Met Pro Ile Ser Glu Val Phe Lys Glu Asp Ile Gly Ile
385                 390                 395                 400

Gly Gly Val Met Ser Leu Leu Trp Phe Arg Arg Leu Pro Asp Tyr
                405                 410                 415

Ala Ser Lys Phe Leu Glu Met Val Leu Met Leu Thr Ala Asp His Gly
            420                 425                 430

Pro Ala Val Ser Gly Ala Met Asn Thr Ile Ile Thr Thr Arg Ala Gly
        435                 440                 445

Lys Asp Leu Ile Ser Ser Leu Val Ala Gly Leu Leu Thr Ile Gly Thr
450                 455                 460

Arg Phe Gly Gly Ala Leu Asp Gly Ala Ala Thr Glu Phe Thr Thr Ala
465                 470                 475                 480

Tyr Asp Lys Gly Leu Ser Pro Arg Gln Phe Val Asp Thr Met Arg Lys
                485                 490                 495

Gln Asn Lys Leu Ile Pro Gly Ile Gly His Arg Val Lys Ser Arg Asn
            500                 505                 510

Asn Pro Asp Phe Arg Val Glu Leu Val Lys Asp Phe Val Lys Lys Asn
        515                 520                 525

Phe Pro Ser Thr Gln Leu Leu Asp Tyr Ala Leu Ala Val Glu Glu Val
    530                 535                 540

Thr Thr Ser Lys Lys Asp Asn Leu Ile Leu Asn Val Asp Gly Ala Ile
545                 550                 555                 560

Ala Val Ser Phe Val Asp Leu Met Arg Ser Cys Gly Ala Phe Thr Val
                565                 570                 575

Glu Glu Thr Glu Asp Tyr Leu Lys Asn Gly Val Leu Asn Gly Leu Phe
            580                 585                 590

Val Leu Gly Arg Ser Ile Gly Leu Ile Ala His His Leu Asp Gln Lys
        595                 600                 605

Arg Leu Lys Thr Gly Leu Tyr Arg His Pro Trp Asp Asp Ile Thr Tyr
    610                 615                 620

Leu Val Gly Gln Glu Ala Ile Gln Lys Lys Arg Val Glu Ile Ser Ala
625                 630                 635                 640

Gly Asp Val Ser Lys Ala Lys Thr Arg Ser
                645                 650

<210> SEQ ID NO 17
<211> LENGTH: 1494
<212> TYPE: DNA
<213> ORGANISM: Yarrowia lipolytica

<400> SEQUENCE: 17
atgtcagcga aatccattca cgaggccgac ggcaaggccc tgctcgcaca ctttctgtcc    60
```

```
aaggcgcccg tgtgggccga gcagcagccc atcaacacgt ttgaaatggg cacacccaag      120
ctggcgtctc tgacgttcga ggacggcgtg gcccccgagc agatcttcgc cgccgctgaa      180
aagacctacc cctggctgct ggagtccggc gccaagtttg tggccaagcc cgaccagctc      240
atcaagcgac gaggcaaggc cggcctgctg gtactcaaca agtcgtggga ggagtgcaag      300
ccctggatcg ccgagcgggc cgccaagccc atcaacgtgg agggcattga cggagtgctg      360
cgaacgttcc tggtcgagcc ctttgtgccc acgaccaga agcacgagta ctacatcaac       420
atccactccg tgcgagaggg cgactggatc ctcttctacc acgagggagg agtcgacgtc      480
ggcgacgtgg acgccaaggc cgccaagatc ctcatccccg ttgacattga aacgagtac       540 ccctccaacg ccacgctcac caaggagctg ctggcacacg tgcccgagga ccagcaccag      600
accctgctcg acttcatcaa ccggctctac gccgtctacg tcgatctgca gtttacgtat      660
ctggagatca ccccctggt cgtgatcccc accgcccagg gcgtcgaggt ccactacctg       720
gatcttgccg gcaagctcga ccagaccgca gagtttgagt gcggcccaa gtgggctgct       780 gcgcggtccc cgccgctct gggccaggtc gtcaccattg acgccggctc caccaaggtg       840
tccatcgacg ccgcccgc catggtcttc cccgctcctt tcggtcgaga gctgtccaag        900
gaggaggcgt acattgcgga gctcgattcc aagaccggag cttctctgaa gctgactgtt      960
ctcaatgcca agggccgaat ctggaccctt gtggctggtg gaggagcctc cgtcgtctac     1020
gccgacgcca ttgcgtctgc cggctttgct gacgagctcg ccaactacgg cgagtactct     1080
ggcgctccca cgagaccca gacctacgag tacgccaaaa ccgtactgga tctcatgacc      1140
cggggcgacg ctcaccccga gggcaaggta ctgttcattg gcggaggaat cgccaacttc     1200
acccaggttg gatccacctt caagggcatc atccgggcct ccgggacta ccagtcttct      1260 ctgcacaacc acaaggtgaa gatttacgtg cgacgaggcg gtcccaactg gcaggagggt     1320
ctgcggttga tcaagtcggc tggcgacgag ctgaatctgc ccatggagat ttacggcccc     1380
gacatgcacg tgtcgggtat tgttcctttg gctctgcttg gaaagcggcc caagaatgtc     1440
aagccttttg gcaccggacc ttctactgag gcttccactc ctctcggagt ttaa           1494
```

<210> SEQ ID NO 18
<211> LENGTH: 497
<212> TYPE: PRT
<213> ORGANISM: Yarrowia lipolytica

<400> SEQUENCE: 18

Met Ser Ala Lys Ser Ile His Glu Ala Asp Gly Lys Ala Leu Leu Ala
1               5                   10                  15

His Phe Leu Ser Lys Ala Pro Val Trp Ala Glu Gln Gln Pro Ile Asn
            20                  25                  30

Thr Phe Glu Met Gly Thr Pro Lys Leu Ala Ser Leu Thr Phe Glu Asp
        35                  40                  45

Gly Val Ala Pro Glu Gln Ile Phe Ala Ala Glu Lys Thr Tyr Pro
    50                  55                  60

Trp Leu Leu Glu Ser Gly Ala Lys Phe Val Ala Lys Pro Asp Gln Leu
65                  70                  75                  80

Ile Lys Arg Arg Gly Lys Ala Gly Leu Leu Val Leu Asn Lys Ser Trp
                85                  90                  95

Glu Glu Cys Lys Pro Trp Ile Ala Glu Arg Ala Ala Lys Pro Ile Asn
            100                 105                 110

Val Glu Gly Ile Asp Gly Val Leu Arg Thr Phe Leu Val Glu Pro Phe

```
            115                 120                 125
Val Pro His Asp Gln Lys His Glu Tyr Tyr Ile Asn Ile His Ser Val
        130                 135                 140
Arg Glu Gly Asp Trp Ile Leu Phe Tyr His Glu Gly Gly Val Asp Val
145                 150                 155                 160
Gly Asp Val Asp Ala Lys Ala Lys Ile Leu Ile Pro Val Asp Ile
                165                 170                 175
Glu Asn Glu Tyr Pro Ser Asn Ala Thr Leu Thr Lys Glu Leu Leu Ala
                180                 185                 190
His Val Pro Glu Asp Gln His Gln Thr Leu Leu Asp Phe Ile Asn Arg
                195                 200                 205
Leu Tyr Ala Val Tyr Val Asp Leu Gln Phe Thr Tyr Leu Glu Ile Asn
        210                 215                 220
Pro Leu Val Val Ile Pro Thr Ala Gln Gly Val Glu Val His Tyr Leu
225                 230                 235                 240
Asp Leu Ala Gly Lys Leu Asp Gln Thr Ala Glu Phe Glu Cys Gly Pro
                245                 250                 255
Lys Trp Ala Ala Ala Arg Ser Pro Ala Ala Leu Gly Gln Val Val Thr
                260                 265                 270
Ile Asp Ala Gly Ser Thr Lys Val Ser Ile Asp Ala Gly Pro Ala Met
                275                 280                 285
Val Phe Pro Ala Pro Phe Gly Arg Glu Leu Ser Lys Glu Glu Ala Tyr
        290                 295                 300
Ile Ala Glu Leu Asp Ser Lys Thr Gly Ala Ser Leu Lys Leu Thr Val
305                 310                 315                 320
Leu Asn Ala Lys Gly Arg Ile Trp Thr Leu Val Ala Gly Gly Ala
                325                 330                 335
Ser Val Val Tyr Ala Asp Ala Ile Ala Ser Ala Gly Phe Ala Asp Glu
                340                 345                 350
Leu Ala Asn Tyr Gly Glu Tyr Ser Gly Ala Pro Asn Glu Thr Gln Thr
                355                 360                 365
Tyr Glu Tyr Ala Lys Thr Val Leu Asp Leu Met Thr Arg Gly Asp Ala
        370                 375                 380
His Pro Glu Gly Lys Val Leu Phe Ile Gly Gly Ile Ala Asn Phe
385                 390                 395                 400
Thr Gln Val Gly Ser Thr Phe Lys Gly Ile Ile Arg Ala Phe Arg Asp
                405                 410                 415
Tyr Gln Ser Ser Leu His Asn His Lys Val Lys Ile Tyr Val Arg Arg
                420                 425                 430
Gly Gly Pro Asn Trp Gln Glu Gly Leu Arg Leu Ile Lys Ser Ala Gly
                435                 440                 445
Asp Glu Leu Asn Leu Pro Met Glu Ile Tyr Gly Pro Asp Met His Val
                450                 455                 460
Ser Gly Ile Val Pro Leu Ala Leu Leu Gly Lys Arg Pro Lys Asn Val
465                 470                 475                 480
Lys Pro Phe Gly Thr Gly Pro Ser Thr Glu Ala Ser Thr Pro Leu Gly
                485                 490                 495
Val
```

<210> SEQ ID NO 19
<211> LENGTH: 406
<212> TYPE: DNA
<213> ORGANISM: Yarrowia lipolytica

```
<400> SEQUENCE: 19
agagaccggg ttggcggcgc atttgtgtcc caaaaaacag ccccaattgc cccaattgac      60
cccaaattga cccagtagcg ggcccaaccc cggcgagagc ccccttctcc ccacatatca     120
aacctccccc ggttcccaca cttgccgtta agggcgtagg gtactgcagt ctggaatcta    180
cgcttgttca gactttgtac tagtttcttt gtctggccat ccgggtaacc catgccggac    240
gcaaaataga ctactgaaaa ttttttttgct ttgtggttgg gactttagcc aagggtataa    300
aagaccaccg tccccgaatt acctttcctc ttcttttctc tctctccttg tcaactcaca    360
cccgaaatcg ttaagcattt ccttctgagt ataagaatca ttcaaa                   406

<210> SEQ ID NO 20
<211> LENGTH: 122
<212> TYPE: DNA
<213> ORGANISM: Yarrowia lipolytica

<400> SEQUENCE: 20
gtgagtttca gaggcagcag caattgccac gggctttgag cacacggccg ggtgtggtcc     60
cattcccatc gacacaagac gccacgtcat ccgaccagca cttttgcag tactaaccgc    120 ag                                                                    122

<210> SEQ ID NO 21
<211> LENGTH: 531
<212> TYPE: DNA
<213> ORGANISM: Yarrowia lipolytica

<400> SEQUENCE: 21
agagaccggg ttggcggcgc atttgtgtcc caaaaaacag ccccaattgc cccaattgac      60
cccaaattga cccagtagcg ggcccaaccc cggcgagagc ccccttctcc ccacatatca     120
aacctccccc ggttcccaca cttgccgtta agggcgtagg gtactgcagt ctggaatcta    180
cgcttgttca gactttgtac tagtttcttt gtctggccat ccgggtaacc catgccggac    240
gcaaaataga ctactgaaaa ttttttttgct ttgtggttgg gactttagcc aagggtataa    300
aagaccaccg tccccgaatt acctttcctc ttcttttctc tctctccttg tcaactcaca    360
cccgaaatcg ttaagcattt ccttctgagt ataagaatca ttcaaaatgg tgagtttcag    420
aggcagcagc aattgccacg ggctttgagc acacggccgg gtgtggtccc attcccatcg    480
acacaagacg ccacgtcatc cgaccagcac ttttgcagt actaaccgca g             531

<210> SEQ ID NO 22
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 22
aatgactgct aacccttcct tggtgt                                           26

<210> SEQ ID NO 23
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 23
ctggtctagg tggatcctta ctcagggccg tcaatgagac                            40
```

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 24
aatgccttct attaagttga actctggtta c                          31

<210> SEQ ID NO 25
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 25
ctaggtctta ctggatcctt agacgaagat aggaatcttg tccca           45

<210> SEQ ID NO 26
<211> LENGTH: 57
<212> TYPE: DNA
<213> ORGANISM: Artificial Sequence
<220> FEATURE:
<223> OTHER INFORMATION: Oligonucleotide primer

<400> SEQUENCE: 26
taaccgcagc atcatcacca tcaccaccct tctattaagt tgaactctgg ttacgac   57

<210> SEQ ID NO 27
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 27
cttacaggta ccttagacga agataggaat cttgtcccag                 40

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 28
tccaggccgt cctctccc                                         18

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 29
ggccagccat atcgagtcgc a                                     21

<210> SEQ ID NO 30
<211> LENGTH: 19
<212> TYPE: DNA
<213> ORGANISM: Artificial Sequence
<220> FEATURE:

```
<223> OTHER INFORMATION: Oligonucleotide primer

<400> SEQUENCE: 30
aaggagtggg ctggatgga                                              19

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 31
ggtctctcgg gtagggatct tg                                          22

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 32
atggaggaat cggcgactt                                              19

<210> SEQ ID NO 33
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 33
accacctctc cggcacttt                                              19

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 34
aacggaggag tggtcaagcg a                                           21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 35
ttatggggaa gtagcggcca a                                           21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 36
ctccaagttg ggttccgttg c                                           21
```

```
<210> SEQ ID NO 37
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 37
gcgacagcag cagccaaaag a                                              21

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 38
aggctatcgc tgctaagcac gg                                             22

<210> SEQ ID NO 39
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 39
tttggaatga tggcaatgcc tc                                             22

<210> SEQ ID NO 40
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 40
cagctcaagg gcatcattct gg                                             22

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 41
tgcggcaagt cgtcctcaaa                                                20

<210> SEQ ID NO 42
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 42
cttcgaaccg cctacctggc ta                                             22

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 43
tgggctggaa catggttcga                                              20

<210> SEQ ID NO 44
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 44
caccgctttc gccattgct                                               19

<210> SEQ ID NO 45
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 45
gggctccttg agcttgaact cc                                           22

<210> SEQ ID NO 46
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 46
ctgtggtgtc gtcaacgact cc                                           22

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 47
gctcaatggc gtaaggagtg g                                            21

<210> SEQ ID NO 48
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 48
tactctcccg aggacattgc c                                            21

<210> SEQ ID NO 49
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 49
cagcttgaag agcttgtcag cc                                           22
```